(12) United States Patent
Cocklin

(10) Patent No.: US 9,920,073 B2
(45) Date of Patent: Mar. 20, 2018

(54) COMPOSITIONS USEFUL FOR INHIBITING HIV-1 INFECTION AND METHODS USING SAME

(71) Applicant: Drexel University, Philadelphia, PA (US)

(72) Inventor: Simon Cocklin, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/025,429

(22) PCT Filed: Oct. 3, 2014

(86) PCT No.: PCT/US2014/058998
§ 371 (c)(1),
(2) Date: Mar. 28, 2016

(87) PCT Pub. No.: WO2015/051230
PCT Pub. Date: Apr. 9, 2015

(65) Prior Publication Data
US 2016/0214998 A1    Jul. 28, 2016

Related U.S. Application Data

(60) Provisional application No. 61/886,881, filed on Oct. 4, 2013, provisional application No. 61/887,549, filed on Oct. 7, 2013, provisional application No. 62/004,391, filed on May 29, 2014.

(51) Int. Cl.

| | | |
|---|---|---|
| C07D 403/06 | (2006.01) | |
| C07D 403/12 | (2006.01) | |
| C07D 403/14 | (2006.01) | |
| C07D 471/04 | (2006.01) | |
| A61K 31/404 | (2006.01) | |
| A61K 31/4196 | (2006.01) | |
| A61K 31/437 | (2006.01) | |
| C07D 495/04 | (2006.01) | |
| C07D 239/38 | (2006.01) | |
| C07D 487/04 | (2006.01) | |
| C07D 519/00 | (2006.01) | |
| A61K 31/496 | (2006.01) | |
| A61K 31/506 | (2006.01) | |
| A61K 31/519 | (2006.01) | |
| A61K 45/06 | (2006.01) | |
| A61K 31/444 | (2006.01) | |
| A61K 31/4545 | (2006.01) | |
| A61K 31/495 | (2006.01) | |
| A61K 31/541 | (2006.01) | |
| A61K 31/407 | (2006.01) | |
| C07D 295/16 | (2006.01) | |
| C07D 307/58 | (2006.01) | |
| C07D 295/192 | (2006.01) | |

(52) U.S. Cl.
CPC .......... *C07D 519/00* (2013.01); *A61K 31/407* (2013.01); *A61K 31/437* (2013.01); *A61K 31/444* (2013.01); *A61K 31/4545* (2013.01); *A61K 31/495* (2013.01); *A61K 31/496* (2013.01); *A61K 31/506* (2013.01); *A61K 31/519* (2013.01); *A61K 31/541* (2013.01); *A61K 45/06* (2013.01); *C07D 239/38* (2013.01); *C07D 295/16* (2013.01); *C07D 471/04* (2013.01); *C07D 487/04* (2013.01); *C07D 495/04* (2013.01)

(58) Field of Classification Search
None
See application file for complete search history.

(56) References Cited

U.S. PATENT DOCUMENTS

| | | |
|---|---|---|
| 2012/0238583 A1 | 9/2012 | Wang et al. |
| 2013/0225635 A1 | 8/2013 | Wang et al. |

FOREIGN PATENT DOCUMENTS

| | | |
|---|---|---|
| EP | 1465631 B1 | 2/2010 |
| WO | 2005079519 A2 | 9/2005 |

OTHER PUBLICATIONS

PCT International Search Report and Written Opinion for PCT International Application No. PCT/US2014/058998 dated Dec. 19, 2014.
Courter, et al., "Structure-based design, synthesis and validation of CD4-mimetic small molecule inhibitors of HIV-1 ?entry: conversion of a viral entry agonist to an antagonist", Acc Chem Res. 47(4), Apr. 15, 2014, 1228-1237.
Curreli, et al., "Design, synthesis, and antiviral activity of entry inhibitors that target the CD4-binding site of HIV-1", J Med Chem. 55(10), May 24, 2012, 4764-4765.

(Continued)

*Primary Examiner* — Emily Bernhardt
(74) *Attorney, Agent, or Firm* — Saul Ewing Arnstein & Lehr LLP; Kathryn Doyle; Domingos J. Silva

(57) ABSTRACT

The present invention includes novel compositions useful for preventing or treating an HIV-1 infection in a subject in need thereof. The present invention further includes a novel method of preventing or treating an HIV-1 infection in a subject in need thereof, the method comprising administering to the subject an effective amount of a compound of the invention. In certain embodiments, the subject is further administered at least one additional therapeutic agent.

(I)

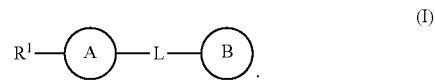

15 Claims, 9 Drawing Sheets

(56) References Cited

OTHER PUBLICATIONS

Kwon, et al., "Crystal structures of HIV-1 gp120 envelope glycoprotein in complex with NBD analogues that target the CD4-binding site", PLoS One. 9(1):e85940, Jan. 28, 2014.

Kwon, et al., "Unliganded HIV-1 gp120 core structures assume the CD4-bound conformation with regulation by quaternary interactions and variable loops", Proc Natl Acad Sci U S A. 109(15), Apr. 10, 2012, 5663-5668.

Lalonde, et al., "Structure-Based Design and Synthesis of an HIV-1 Entry Inhibitor Exploiting X-Ray and Thermodynamic Characterization", ACS Med Chem Lett. 4(3), Mar. 14, 2013, 338-343.

Li, et al., "Activity of the HIV-1 attachment inhibitor BMS-626529, the active component of the prodrug BMS-663068, against CD4-independent viruses and HIV-1 envelopes resistant to other entry inhibitors", Antimicrob Agents Chemother. 57(9), Sep. 2013, 4172-4180.

Lin, et al., "A small molecule HIV-1 inhibitor that targets the HIV-1 envelope and inhibits CD4 receptor binding", Proc Natl Acad Sci U S A. 100(19), Sep. 16, 2003, 11013-11018.

Lyumkis, et al., "Cryo-EM structure of a fully glycosylated soluble cleaved HIV-1 envelope trimer", Science 342 (6165), Dec. 20, 2013, 1484-1490.

Nettles, et al., "Pharmacodynamics, safety, and pharmacokinetics of BMS-663068, an oral HIV-1 attachment inhibitor in HIV-1-infected subjects", J Infect Dis. 206(7), Oct. 1, 2012, 1002-1011.

Nowicka-Sans, et al., "In vitro antiviral characteristics of HIV-1 attachment inhibitor BMS-626529, the active component of the prodrug BMS-663068", Antimicrob Agents Chemother. 56(7), Jul. 2012, 3498-3507.

Si, et al., "Small-molecule inhibitors of HIV-1 entry block receptor-induced conformational changes in the viral envelope glycoproteins", Proc Natl Acad Sci U S A. 101(14), Apr. 6, 2004, 5036-5041.

Wang, et al., "Discovery of 4-benzoyl-1-[(4-methoxy-1H-pyrrolo[2,3-b]pyridin-3-yl)oxoacetyl]-2-(R)-methylpiperazine (BMS-378806): a novel HIV-1 attachment inhibitor that interferes with CD4-gp120 interactions", J Med Chem. 46(20), Sep. 25, 2003, 4236-4239 (Abstract Only).

Williams, et al., "Discovery of a small molecule inhibitor through interference with the gp120-CD4 interaction", Bioorg Med Chem Lett. 19(17), Sep. 1, 2009, 5246-5249 (Abstract Only).

Yang, et al., "Utilization of in vitro Caco-2 permeability and liver microsomal half-life screens in discovering BMS-488043, a novel HIV-1 attachment inhibitor with improved pharmacokinetic properties", J Pharm Sci. 99(4), Apr. 2010, 2135-2152.

Zhao, et al. "Identification of N-phenyl-N'-(2,2,6,6-tetramethyl-piperidin-4-yl)-oxalamides as a new class of HIV-1 entry inhibitors that prevent gp120 binding to CD4", Virology. 339(2), Sep. 1, 2005, 213-225.

R = H: BMS-626529

R = CH₂OP(O)(OH)₂: BMS-663068

BMS-488043     BMS-378806 raltegravir

NBD-556 binding

BMS-378806 binding

COMPOSITIONS USEFUL FOR INHIBITING HIV-1 INFECTION AND METHODS USING SAME

CROSS-REFERENCE TO RELATED APPLICATIONS

The present application claims priority under 35 U.S.C. § 119(e) to U.S. Provisional Patent Application No. 62/004,391, filed May 29, 2014; No. 61/887,549, filed Oct. 7, 2013; and No. 61/886,881, filed Oct. 4, 2013, all of which applications are incorporated herein by reference in their entireties.

STATEMENT REGARDING FEDERALLY SPONSORED RESEARCH OR DEVELOPMENT

This invention was made with government support under 1R21AI104354-01A1 awarded by National Institute of Allergy and Infectious Diseases (NIH). The government has certain rights in the invention.

BACKGROUND OF THE INVENTION

The entry of HIV-1 into permissible cells involves a complex series of events, orchestrated by the viral envelope glycoprotein complex, the only viral components exposed on the virion surface. As the only viral products accessible to the host cell immune system, the Env glycoproteins (gp120 and gp41) have evolved several strategies to mask functionally important regions from the neutralizing antibody response. These include the presence of surface-exposed variable loops on gp120, a high degree of glycosylation, the lability and defectiveness of many envelope glycoprotein spikes (possible immunologic decoys), and conformational flexibility.

The Env complex is organized on the virion surface as trimeric spikes, composed of three gp120 molecules noncovalently linked to three gp41 molecules. The heavily glycosylated surface gp120 contains a core composed of conserved regions (C1 to C5) and hypervariable regions that are mostly disulfide-constrained, surface-exposed loop structures (V1 to V5) that retain a large degree of flexibility. The transmembrane glycoprotein gp41 contains the fusion peptide, which is inserted into the membrane of the target cell as well as two heptad repeat (HR) domains (aminoterminal or HR1 and carboxyterminal or HR2) that are implicated in the formation of a six-helix-bundle fusion intermediate through a conformational change following receptor interaction.

HIV-1, unlike pH dependent viruses, uses receptor engagement to elicit the conformational changes in the viral envelope glycoproteins required for fusion. The receptor used by HIV-1 is CD4. Many studies have demonstrated that CD4 engagement induces significant changes in gp120. These changes in gp120 allow chemokine receptor binding and also result in the formation and/or exposure of the HR1 coiled coil on gp41. The effects of gp120 binding to CD4, in conjunction with binding to the chemokine receptor, initiate the conformational transitions required for membrane fusion. Therefore, both intra- and intermolecular interactions coordinate to facilitate the transduction of receptor-binding signals between the components of the Env complex and ultimately result in fusion.

HIV-1 infection usually occurs only after two sequential and specific binding steps: first, to the CD4 antigen present in CD4$^+$ T cells, monocyte/macrophages, and other immune/nonimmune cells; second, to a member of the chemokine receptor subfamily, within the large G protein-coupled family of receptors, mainly CCR5 and/or CXCR4. Binding of CD4 or other ligands to the Phe43 cavity of gp120 is often accompanied by a conformational rearrangement that exposes coreceptor binding surfaces. Further, ligands binding to gp120 at sites other than the Phe43 cavity can elicit positive or negative conformational changes, enhancing or limiting the accessibility of the co-receptor binding site.

Because of the emergence of drug-resistant strains and the cumulative toxicities associated with current therapies, demand remains for new inhibitors of HIV-1 replication. An attractive intervention point for such new inhibitors is viral entry into permissible cells. However, this strategy remains almost completely unexploited. In the HIV-1 entry field, only two main inhibitor chemotypes predominate: the NBD-556 analogues (Zhao et al., 2005, Virology, 339:215-225) and the BMS-377806 analogues (Wang et al., 2003, J. Med. Chem. 46:4236-4239). The NBD-556 analogues suffer from the propensity to elicit the same conformational rearragements as CD4, limiting their current use, as they could promote infection of cells not usually permissible to HIV-1 infection. Similarly, the BMS-377806 analogues, although very potent and with no promotion of infection of CD4 negative cells, have poor solubility and oral bioavailability. Therefore, given the enormous potential of small molecule entry inhibitors, new chemotypes with high potency and improved drug-like qualities are highly desirable.

Compounds with distinct chemical structures can bind at the same biological site and elicit the same agonist/antagonist effect. As such, binding sites must recognize specific attributes of the compound/molecule that lead to its biological activity and not specific structural detail, i.e., the regions of positive and negative charge, lipophilicity, and the spatial arrangement of these regions. A new variation of this pharmacophore approach is the use of FieldPoints, which are the local extrema of these potential and shape surfaces. FieldPoints can be used to describe and compare biologically active molecules and to scaffold-hop. To date, the piperazine-based entry inhibitors as first described by Bristol-Myers Squibb (Wang et al., 2003, J. Med. Chem. 46:4236-4239) are the most broadly acting and potent HIV-1 entry inhibitors. This indicates that the binding site for these compounds, although currently not well described, is broadly conserved and available for targeting on the virion.

There is a need in the art for novel compositions that are useful for the treatment of HIV-1 infection in a mammal. The present invention addresses this unmet need.

BRIEF SUMMARY OF THE INVENTION

The present invention relates to the unexpected discovery of novel compounds that treat or prevent HIV-1 infection in a mammal. In one aspect, the invention relates to a compound of formula (I), or a salt or solvate thereof. In another aspect, the invention relates to a pharmaceutical composition comprising at least one compound of the invention and at least one pharmaceutically acceptable carrier. In yet another aspect, the invention relates to a method of preventing or treating an HIV-1 infection in a subject in need thereof, the method comprising administering to the subject a therapeutically effective amount of at least one compound of formula (I).

In certain embodiments, the compound of formula (I), or a salt, N-oxide or solvate thereof, is:

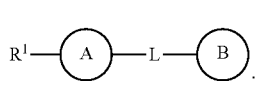
wherein in (I):
R¹ is selected from the group consisting of
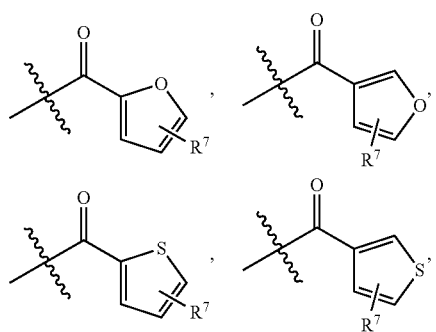
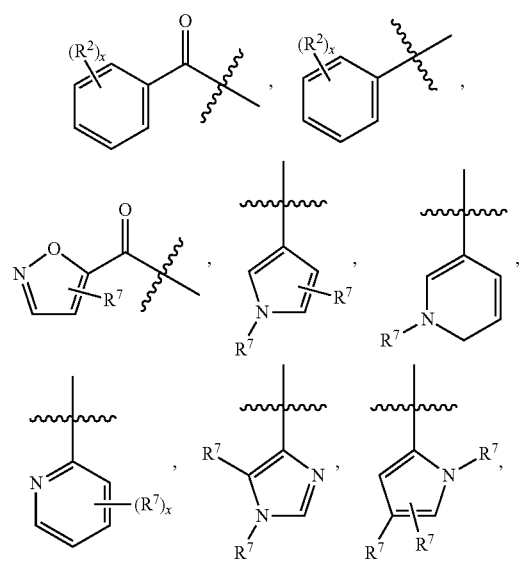
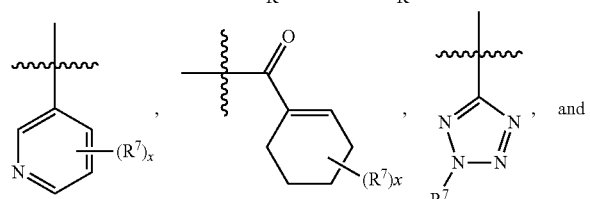
and
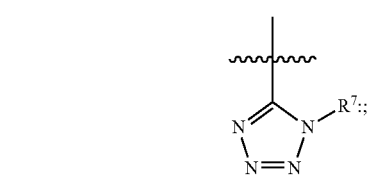
ring A is selected from the group consisting of:
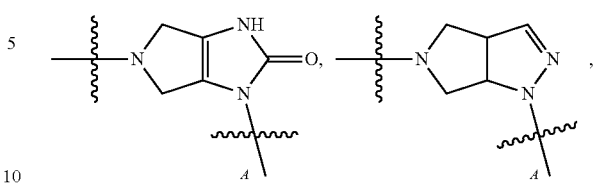
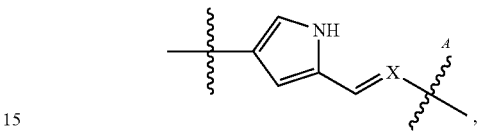
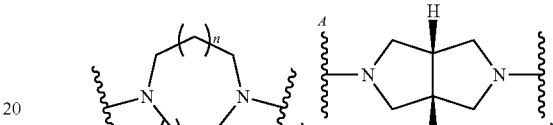
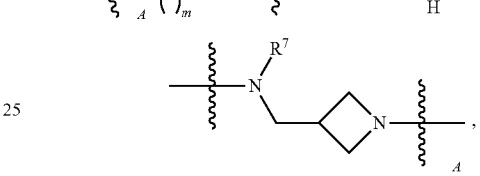
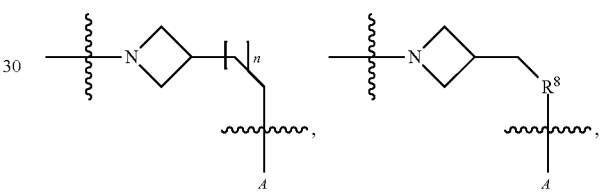
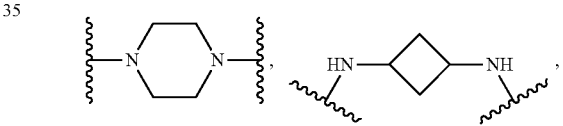
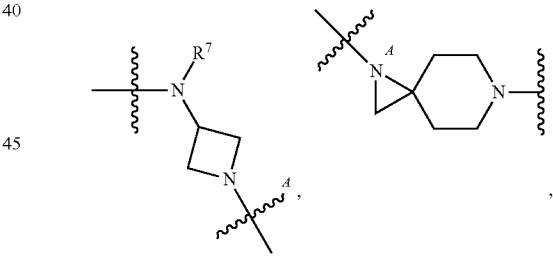
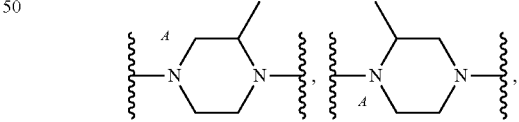
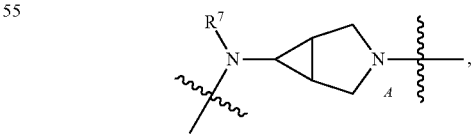
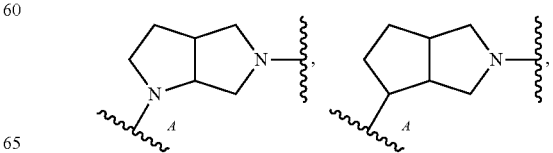

-continued

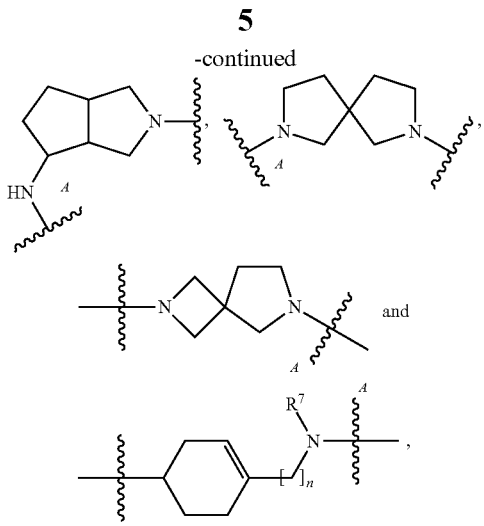

wherein the atom labeled with A is linked to ring $R^1$;
linker L is selected from the group consisting of:

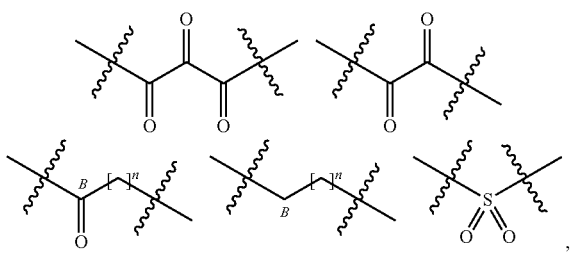

wherein the atom labeled with B is linked to ring B;
ring B is selected from the group consisting of:

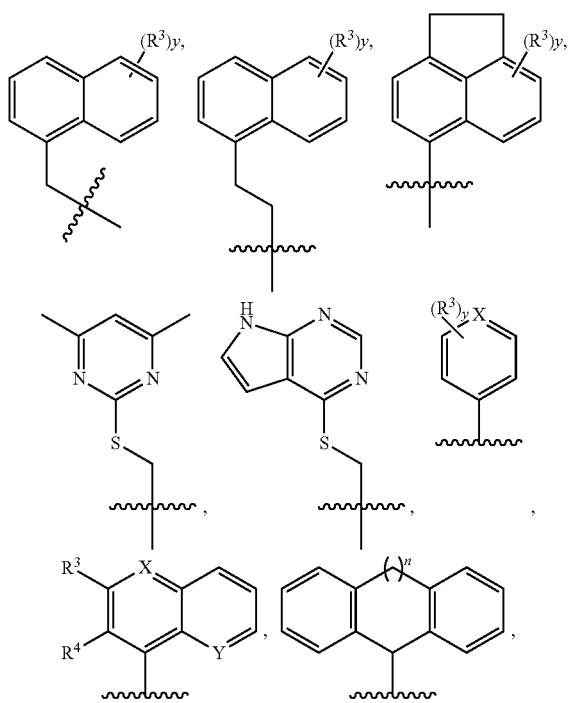

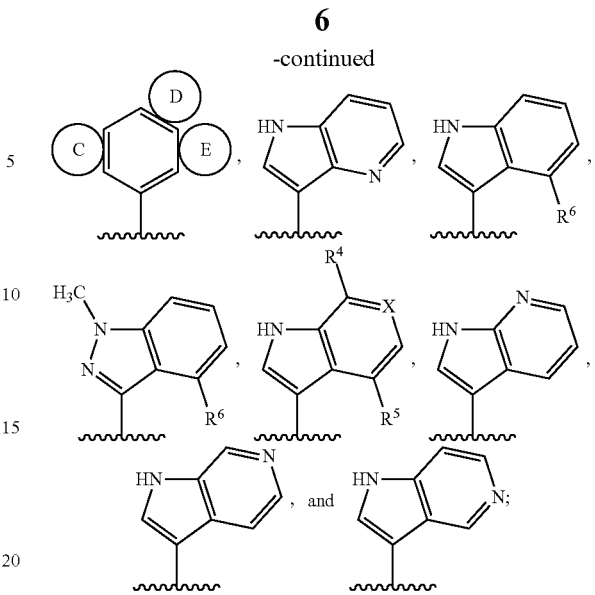

wherein rings C, D, and E are each independently absent or a monocyclic aryl or monocyclic heteroaryl ring optionally substituted;

each occurrence of $R^2$ and $R^3$ is independently selected from the group consisting of —$(C_1-C_6)$alkyl, —$(C_1-C_6)$fluoroalkyl, —$(C_1-C_6)$heteroalkyl, —F, —Cl, —Br, —I, —CN, —$NO_2$, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$;

$R^4$ and $R^5$ are each selected from the group consisting of —$(C_1-C_6)$alkyl, —$(C_1-C_6)$fluoroalkyl, —$(C_1-C_6)$heteroalkyl, —F, —Cl, —Br, —I, —CN, —$NO_2$, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, heterocycloalkyl, aryl, and heteroaryl, wherein the heterocycloalkyl, aryl or heteroaryl may be optionally substituted;

$R^6$ is H or F;

each occurrence of $R^7$ is independently selected from the group consisting of H, —$(C_1-C_6)$alkyl, —$(C_1-C_6)$heteroalkyl, —$(C_1-C_3)$alkyl-$(C_3-C_6)$cycloalkyl, —$(C_4-C_{10})$heterocyclyl, —$(C_1-C_3)$alkyl-$(C_4-C_{10})$heterocyclyl, —$(C_6-C_{10})$aryl, —$(C_1-C_3)$alkyl-$(C_6-C_{10})$aryl, —$(C_5-C_{10})$heteroaryl, and —$(C_1-C_3)$alkyl-$(C_5-C_{10})$heteroaryl, wherein the alkyl, heteroalkyl, cycloalkyl, heterocycle, aryl, or heteroaryl group is optionally substituted;

$R^8$ is O or S;

X and Y are independently CH or N;

x is an integer from 0-5;

y is an integer from 0-4; and each occurrence of n is independently 0 or 1.

In certain embodiments, the compound is not (4-benzoylpiperazin-1-yl)(1,2-dihydroacenaphthylen-5-yl)methanone (SC03).

In certain embodiments, the compound is not 1-(5-benzoylhexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC11).

In certain embodiments, R¹ is selected from the group consisting of:

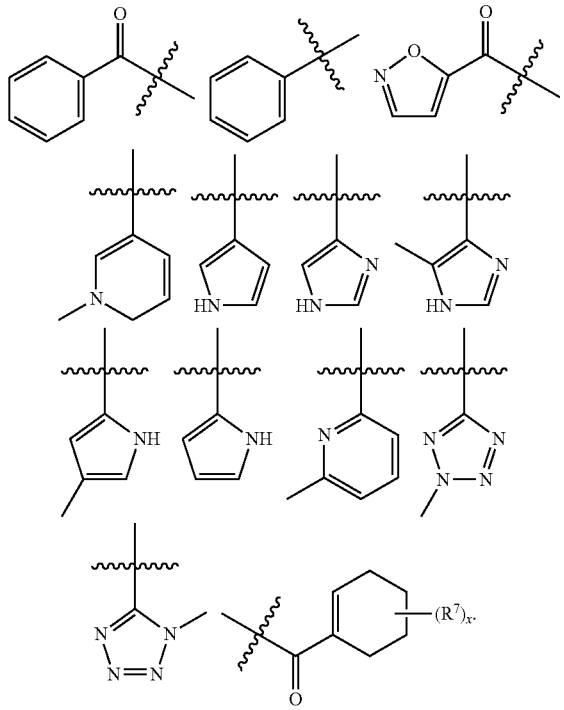

In certain embodiments, ring A is

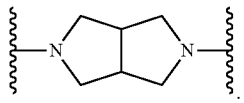

In other embodiments, ring A is

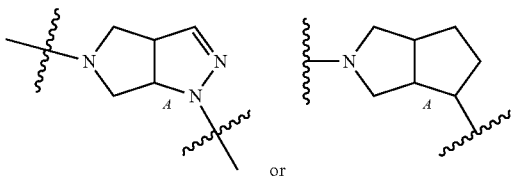

wherein the atom labeled with A is linked to ring A. In yet other embodiments, R¹ is

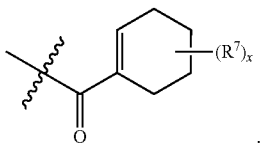

In certain embodiments, the compound of formula (I) is selected from a group consisting of: 2-(thieno[2,3-d]pyrimidin-4-ylthio)-1-(4-(thiophene-2-carbonyl)piperazin-1-yl)ethan-1-one (DC04); 1-(4-(furan-2-carbonyl)piperazin-1-yl)-2-(naphthalen-1-yl)ethan-1-one (DC08); 1-(4-benzoylpiperazin-1-yl)-2-((4,6-dimethylpyrimidin-2-yl)thio)ethan-1-one (DC10); 1-(4-benzoylpiperazin-1-yl)-2-(naphthalen-1-yloxy)ethan-1-one (DC18); (4-benzoylpiperazin-1-yl)(1,2-dihydroacenaphthylen-5-yl)methanone (SC03); (5-benzoyl hexahydropyrrolo[3,4-c]pyrrol-2(1H)-yl)(1,2-dihydroacenaphthylen-5-yl)methanone (SC04); 4-benzoyl-1-(1,2-dihydroacenaphthylene-5-carbonyl)-2-methylpiperazine (SC06); 1-(5-benzoylhexahydropyrrolo[3,4-c]pyrrol-2(1H)-yl)-2-(7-chloro-4-methoxy-1H-pyrrolo[2,3-c]pyridin-3-yl)ethane-1,2-dione (SC07); 1-(5-benzoylhexahydropyrrolo[3,4-c]pyrrol-2(1H)-yl)-2-(4,7-dimethoxy-1H-pyrrolo[2,3-c]pyridin-3-yl)ethane-1,2-dione (SC08); 1-(4,7-dimethoxy-1H-pyrrolo[2,3-c]pyridin-3-yl)-2-(4-phenyl hexahydrocyclopenta[c]pyrrol-2(1H)-yl)ethane-1,2-dione (SC10); 1-(5-benzoylhexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC11); 1-(4-methoxy-7-(3-methyl-1H-1,2,4-triazol-1-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione (SC12); N-((1-benzoylazetidin-3-yl)methyl)-2-(4-methoxy-7-(3-methyl-1H-1,2,4-triazol-1-yl)-1H-pyrrolo[2,3-c]pyridin-3-yl)-2-oxoacetamide (SC14); 1-(4-methoxy-7-(3-methyl-1H-1,2,4-triazol-1-yl)-1H-pyrrolo[2,3-c]pyridin-3-yl)-2-(3-(3-oxo-3-phenylpropyl)azetidin-1-yl)ethane-1,2-dione (SC15); S-((1-(2-(4-methoxy-7-(3-methyl-1H-1,2,4-triazol-1-yl)-1H-pyrrolo[2,3-c]pyridin-3-yl)-2-oxoacetyl)azetidin-3-yl)methyl) benzothioate (SC16); N-(1-benzoylazetidin-3-yl)-2-(4-methoxy-7-(3-methyl-1H-1,2,4-triazol-1-yl)-1H-pyrrolo[2,3-c]pyridin-3-yl)-N-methyl-2-oxoacetamide (SC18); 1-(4-methoxy-7-(3-methyl-1H-1,2,4-triazol-1-yl)-1H-pyrrolo[2,3-c]pyridin-3-yl)-2-(1-(1-methyl-1,6-dihydropyridin-3-yl)-3a,4,6,6a-tetrahydropyrrolo[3,4-c]pyrazol-5(1H)-yl)ethane-1,2-dione (SC19); 1-(1-(1H-pyrrol-3-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione (SC20); 1-(1-(1H-imidazol-4-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione (SC21); 1-(4-methoxy-7-(3-methyl-1H-1,2,4-triazol-1-yl)-1H-pyrrolo[2,3-c]pyridin-3-yl)-2-(1-(4-methyl-1H-pyrrol-2-yl)-3a,4,6,6a-tetrahydropyrrolo[3,4-c]pyrazol-5(1H)-yl)ethane-1,2-dione (SC22); 1-(4-methoxy-7-(3-methyl-1H-1,2,4-triazol-1-yl)-1H-pyrrolo[2,3-c]pyridin-3-yl)-2-(1-(5-methyl-1H-imidazol-4-yl)-3a,4,6,6a-tetrahydropyrrolo[3,4-c]pyrazol-5(1H)-yl)ethane-1,2-dione (SC23); 1-(4-methoxy-7-(3-methyl-1H-1,2,4-triazol-1-yl)-1H-pyrrolo[2,3-c]pyridin-3-yl)-2-(1-(6-methylpyridin-2-yl)-3a,4,6,6a-tetrahydropyrrolo[3,4-c]pyrazol-5(1H)-yl)ethane-1,2-dione (SC24); 1-(1-(1H-pyrrol-2-yl)-3a,4,6,6a-tetrahydropyrrolo[3,4-c]pyrazol-5(1H)-yl)-2-(4-methoxy-7-(3-methyl-H-1,2,4-triazol-1-yl)-1H-pyrrolo[2,3-c]pyridin-3-yl)ethane-1,2-dione (SC25); 1-(5-(cyclohex-1-ene-1-carbonyl)hexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC26); 1-(8-benzoyl-2,8-diazaspiro[4.5]decan-2-yl)-2-(4-methoxy-7-(3-methyl-1H-1,2,4-triazol-1-yl)-1H-pyrrolo[2,3-c]pyridin-3-yl)ethane-1,2-dione (SC27); N-(3-benzoyl-3-azabicyclo[3.1.0]hexan-6-yl)-3-(4-methoxy-7-(3-methyl-1H-1,2,4-triazol-1-yl)-1H-pyrrolo[2,3-c]pyridin-3-yl)-2,3-dioxopropanamide (SC28); 1-(6-(cyclohex-1-ene-1-carbonyl)-2,6-diazaspiro[3.4]octan-2-yl)-2-(4-methoxy-7-(3-methyl-1H-1,2,4-triazol-1-yl)-1H-pyrrolo[2,3-c]pyridin-3-yl)ethane-1,2-dione (SC29); 1-(4-fluoro-7-(1H-1,2,3-triazol-1-yl)-1H-pyrrolo[2,3-c]pyridin-3-yl)-2-(1-phenyl- 3a,4,6,6a-tetrahydropyrrolo[3,4-c]pyrazol-5(1H)-yl)ethane-1,2-dione (SC38); 1-(4-fluoro-7-(3-methyl-1H-1,2,4-triazol-1-yl)-1H-pyrrolo[2,3-c]pyridin-3-yl)-2-(1-(1-phenyl-1H-tetrazol-5-yl)-3a,4,6,6a-tetrahydropyrrolo[3,4-c]pyrazol-5(1H)-yl)ethane-1,2-dione (SC39); 1-(1-benzoyl-1,6-diazaspiro[2.5]octan-6-yl)-2-(4-methoxy-7-(3-methyl-1H-1,2,4-triazol-1-yl)-1H-pyrrolo[2,3-c]pyridin-3-yl) ethane-1,2-dione (SC41); 1-(4-methoxy-7-(3-methyl-1H-1,2,4-triazol-1-yl)-1H-pyrrolo[2,3-c]pyridin-3-yl)-2-(1-(1-phenyl-1H-tetrazol-5-yl)-1,6-diazaspiro[2.5]octan-6-yl) ethane-1,2-dione (SC42); 1-(5-benzoylhexahydropyrrolo[3,4-c]pyrrol-2(1H)-yl)-2-(4-fluoro-7-(2H-1,2,3-triazol-2-yl)-1H-pyrrolo[2,3-c]pyridin-3-yl)ethane-1,2-dione (SC43); 1-(4-fluoro-7-(2H-1,2,3-triazol-2-yl)-1H-pyrrolo[2,3-c]pyridin-3-yl)-2-(1-phenyl-3a,4,6,6a-tetrahydropyrrolo[3,4-c]pyrazol-5 (1H)-yl)ethane-1,2-dione (SC44); and N-((1-(2-(4-methoxy-7-(3-methyl-1H-1,2,4-triazol-1-yl)-1H-pyrrolo[2,3-c]pyridin-3-yl)-2-oxoacetyl)-1,2,3,6-tetrahydropyridin-4-yl)methyl)benzamide (SC45).

In certain embodiments, the composition further comprises one additional therapeutic agent. In other embodiments, the at least one additional therapeutic agent comprises at least one selected from the group consisting of a HIV drug combination, entry and fusion inhibitor, integrase inhibitor, non-nucleoside reverse transcriptase inhibitor, nucleoside reverse transcriptase inhibitor, and protease inhibitor.

In certain embodiments, the method further comprises administering to the subject at least one additional therapeutic agent. In other embodiments, the compound and the at least one additional therapeutic agent are co-administered to the subject. In yet other embodiments, the compound and the at least one additional therapeutic agent are coformulated. In yet other embodiments, the subject is a mammal. In yet other embodiments, the mammal is a human.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 6, comprising FIG. 6A: Field point template A contains a single conformation of compounds BMS-378806 (pink), BMS488043 (lime green), and BMS-626529 (seafoam green) aligned based on their field point patterns. Negatively charged field points are shown in blue; positively charged field points are red; van der Waals/shape field points are displayed in yellow; centers of hydrophobicity are shown in orange. FIG. 6B: Conformation 69 of BMS-626529 with associated field points. This conformation was common to the top three templates identified and was used as the pharmacophore seed for the Blaze virtual screen.

DETAILED DESCRIPTION OF THE INVENTION

Figure 1:
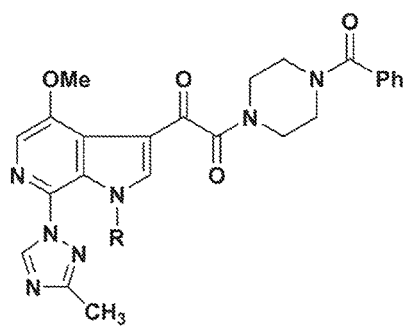
FIG. 1 illustrates structures of reference compounds.
Figure 1:
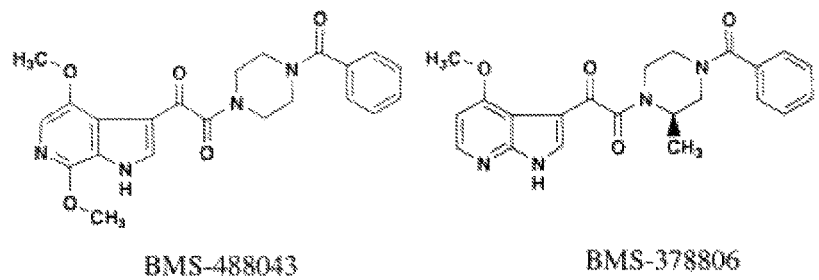
Figure 1:
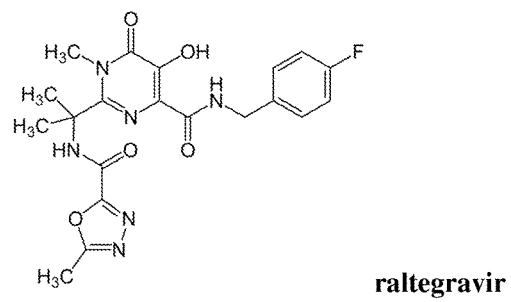

The present invention relates to the unexpected discovery of novel compounds that treat or prevent HIV-1 infection in a mammal. In certain embodiments, the compounds of the invention inhibit the entry of HIV-1 into a mammalian cell. In other embodiments, the mammal is human.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, non-limiting specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.10% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "CNS" refers to central nervous system.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "efficacy" refers to the maximal effect ($E_{max}$) achieved within an assay.

As used herein, the term "NBD-556" refers to N1-(4-chlorophenyl)-N2-(2,2,6,6-tetramethyl-4-piperidinyl)-ethanediamide, or a salt or solvate thereof:

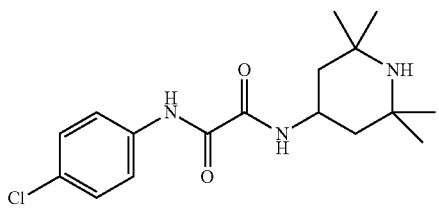

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the terms "pharmaceutically effective amount" and "effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

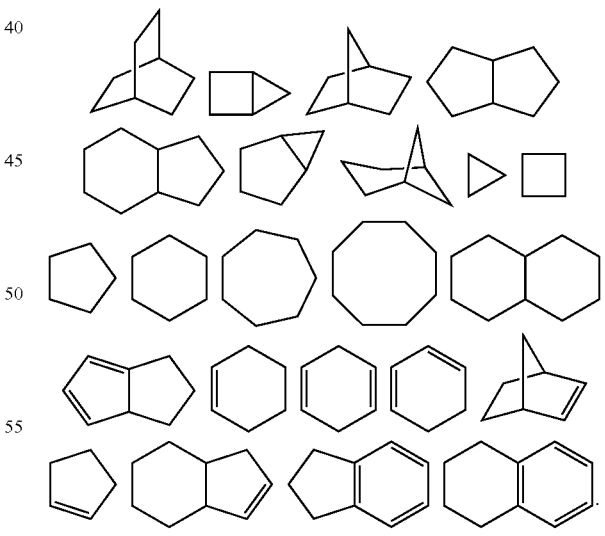

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

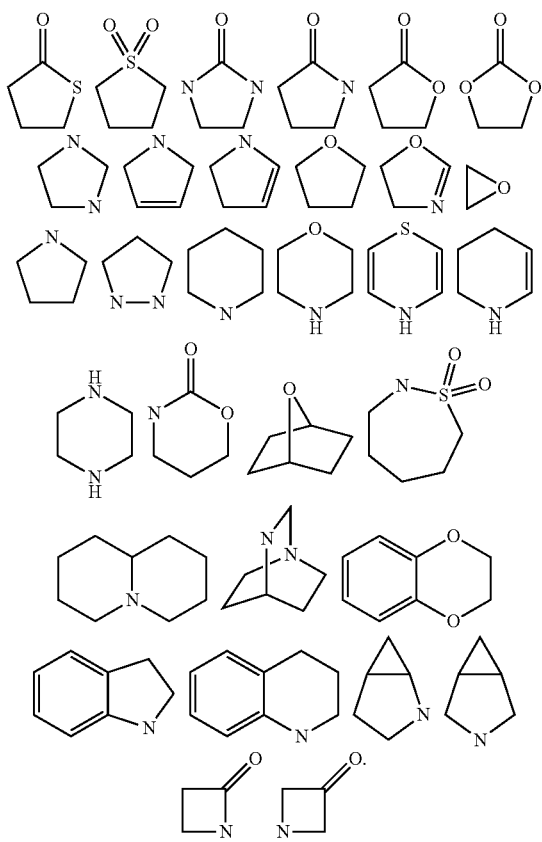

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —CH$_2$CH$_2$-phenyl. Preferred is aryl-CH$_2$— and aryl-CH(CH$_3$)—. The term "substituted aryl-($C_1$-$C_3$)alkyl" means an aryl-($C_1$-$C_3$)alkyl functional group in which the aryl group is substituted. Preferred is substituted aryl(CH$_2$)—. Similarly, the term "heteroaryl-($C_1$-$C_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-(CH$_2$)—.

As used herein, the term "heteroaryl" or "heteroaromatic" refers to a heterocycle having aromatic character. A polycyclic heteroaryl may include one or more rings that are partially saturated. Examples include the following moieties:

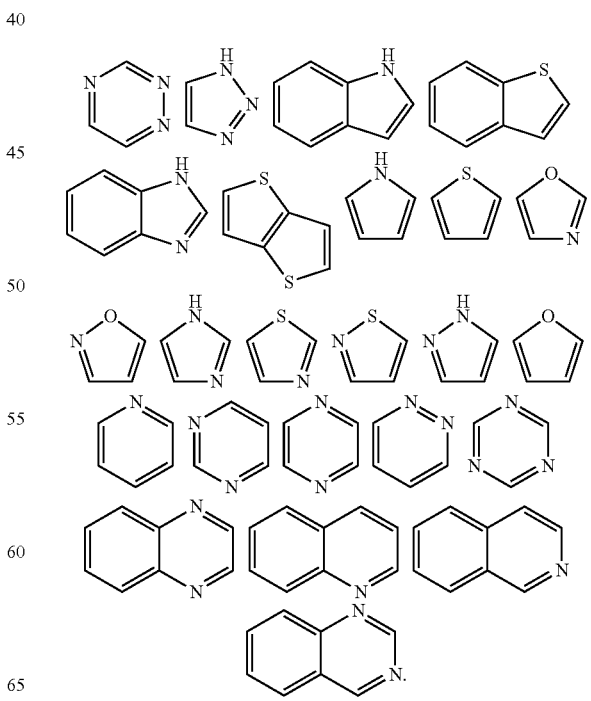

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In other embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet other embodiments, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to the unexpected discovery of novel compounds that are useful in treating an HIV-1 infection in a mammal. In certain embodiments, the compounds of the invention inhibit the entry of HIV-1 into a mammalian cell. In other embodiments, the compounds of the invention have improved drug-like properties over compounds known in the art to treat an HIV-1 infection.

Compounds & Compositions

The compounds of the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), a salt, solvate, or N-oxide thereof:

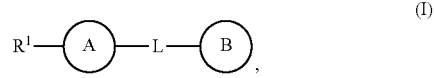

wherein in (I):
R$^1$ is selected from the group consisting of

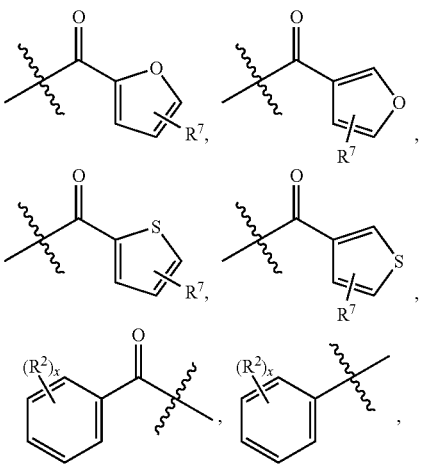

-continued
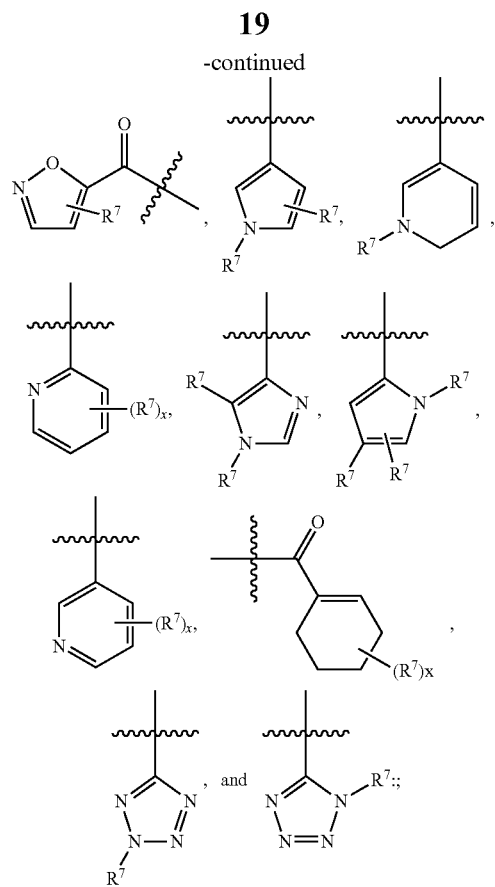
ring A is selected from the group consisting of:
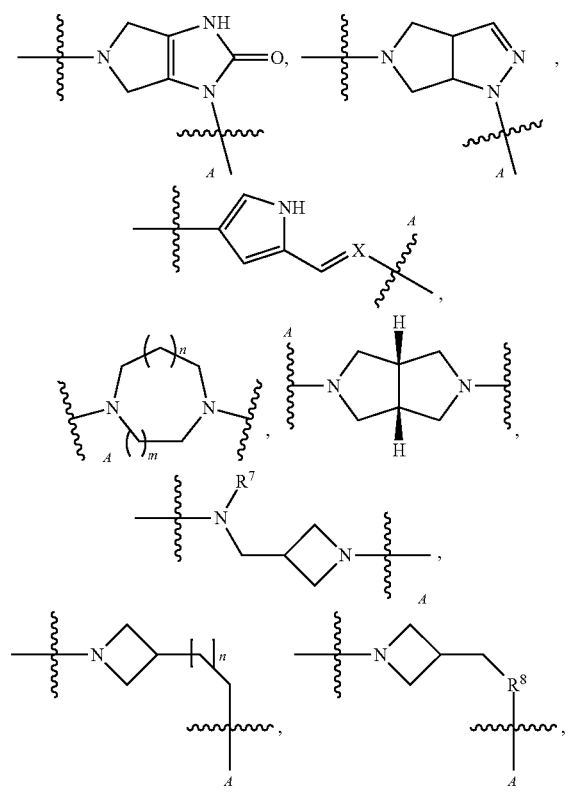
-continued
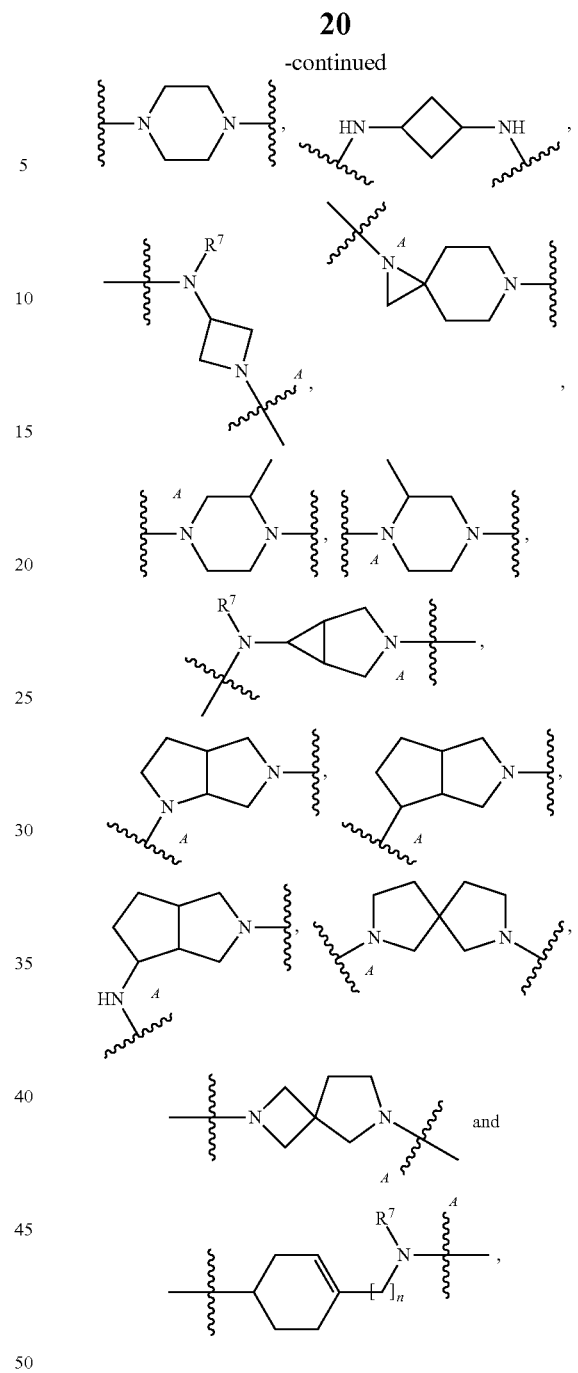
wherein the atom labeled with A is linked to ring $R^1$;
linker L is selected from the group consisting of:
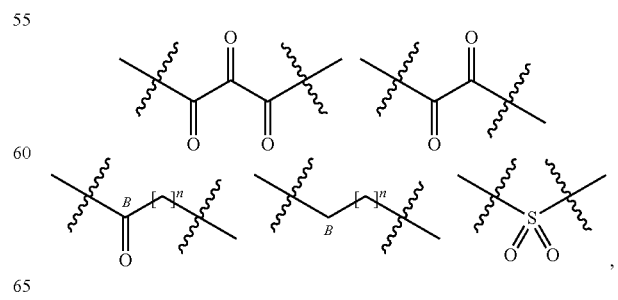
wherein the atom labeled with B is linked to ring B;

ring B is selected from the group consisting of:

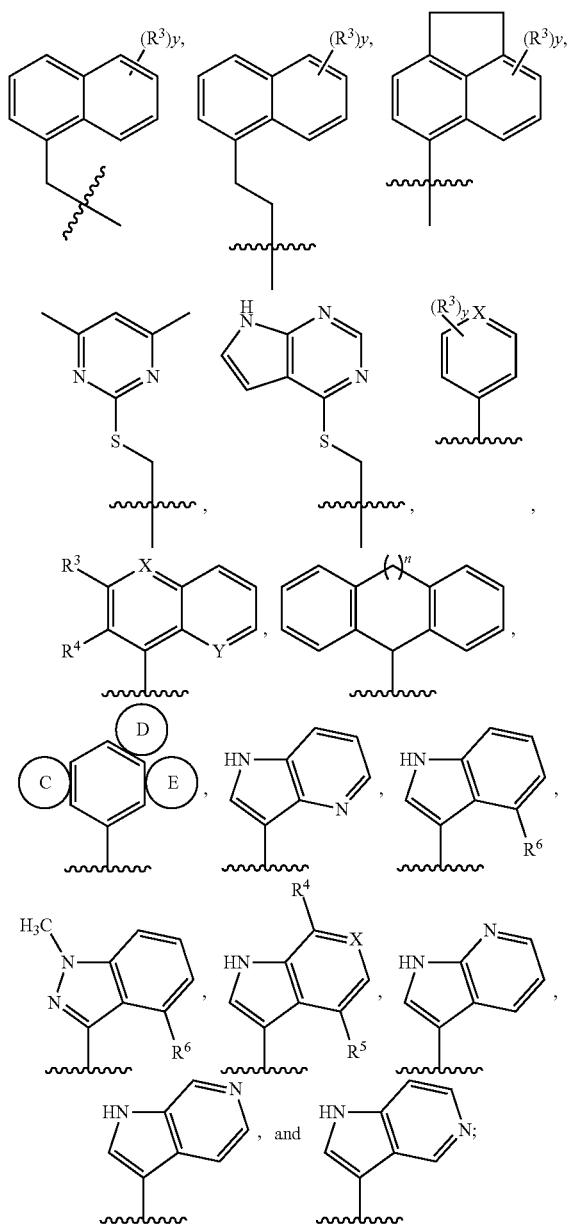

wherein rings C, D, and E are each independently absent or a monocyclic aryl or monocyclic heteroaryl ring optionally substituted;

each occurrence of $R^2$ and $R^3$ is independently selected from the group consisting of —$(C_1$-$C_6)$alkyl, —$(C_1$-$C_6)$fluoroalkyl, —$(C_1$-$C_6)$heteroalkyl, —F, —Cl, —Br, —I, —CN, —$NO_2$, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R)$, —$NHC(=O)R^7$, —$NHC(=O)OR^7$, —$C(OH)(R^7)_2$, and —$C(NH_2)(R^7)_2$;

$R^4$ and $R^5$ are each independently selected from the group consisting of —$(C_1$-$C_6)$alkyl, —$(C_1$-$C_6)$fluoroalkyl, —$(C_1$-$C_6)$heteroalkyl, —F, —Cl, —Br, —I, —CN, —$NO_2$, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, aryl, and heteroaryl, wherein the aryl or heteroaryl may be optionally substituted;

$R^6$ is H or F;

each occurrence of $R^7$ is independently selected from the group consisting of H, —$(C_1$-$C_6)$alkyl, —$(C_1$-$C_6)$heteroalkyl, —$(C_1$-$C_3)$alkyl-$(C_3$-$C_6)$cycloalkyl, —$(C_4$-$C_{10})$heterocyclyl, —$(C_1$-$C_3)$alkyl-$(C_4$-$C_{10})$heterocyclyl, —$(C_6$-$C_{10})$aryl, —$(C_1$-$C_3)$alkyl-$(C_6$-$C_{10})$aryl, —$(C_5$-$C_{10})$heteroaryl, and —$(C_1$-$C_3)$alkyl-$(C_5$-$C_{10})$heteroaryl, wherein the alkyl, heteroalkyl, cycloalkyl, heterocycle, aryl, or heteroaryl group is optionally substituted;

$R^8$ is O or S; X and Y are independently CH or N; x is an integer from 0-5; y is an integer from 0-4; and each occurrence of n is independently 0 or 1.

In certain embodiments, the compound is not (4-benzoylpiperazin-1-yl)(1,2-dihydroacenaphthylen-5-yl)methanone (SC03).

In certain embodiments, the compound is not 1-(5-benzoylhexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC11).

In certain embodiments, ring A is

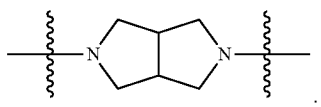 [SMILES: *N1CC2CN(*)CC2C1]

In other embodiments, ring A is

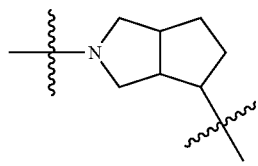

In yet other embodiments, ring A is

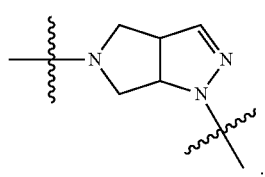 [SMILES: *N1CC2C=NN(*)C2C1]

In yet other embodiments, ring A is

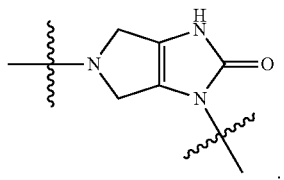 [SMILES: *N1Cc2[nH]c(=O)n(*)c2C1]

In yet other embodiments, ring A is

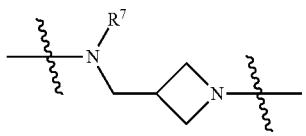

In yet other embodiments, ring A is

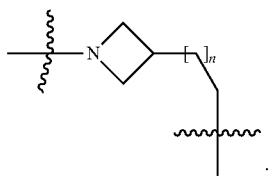

In yet other embodiments, ring A is

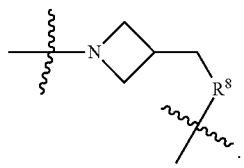

In yet other embodiments, ring A is

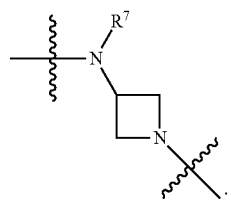

In yet other embodiments, ring A is

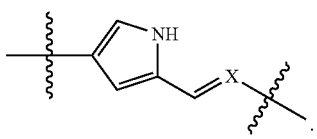

In certain embodiments, linker L is

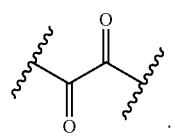 [SMILES: *C(=O)C(*)=O]

In yet other embodiments, linker L is

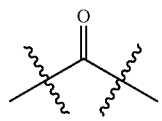

In certain embodiments, ring $R^2$ is substituted phenyl.
In certain embodiments, ring B is

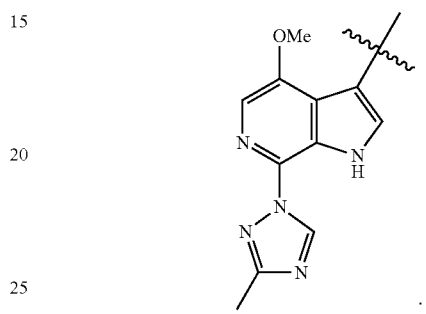

In other embodiments, ring B is

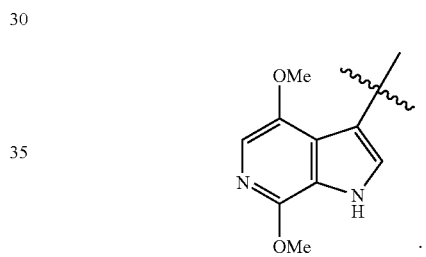

In certain embodiments, ring $R^1$ is selected from the group consisting of:

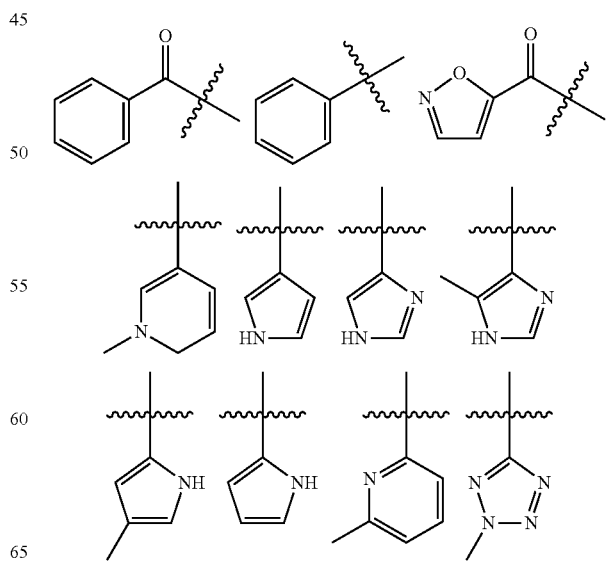

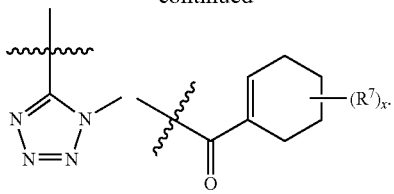

In certain embodiments, the compound of the invention is selected from the group consisting of: 2-(thieno[2,3-d]pyrimidin-4-ylthio)-1-(4-(thiophene-2-carbonyl) piperazin-1-yl)ethan-1-one (DC04); 1-(4-(furan-2-carbonyl)piperazin-1-yl)-2-(naphthalen-1-yl)ethan-1-one (DC08); 1-(4-benzoylpiperazin-1-yl)-2-((4,6-dimethylpyrimidin-2-yl)thio) ethan-1-one (DC10); 1-(4-benzoylpiperazin-1-yl)-2-(naphthalen-1-yloxy)ethan-1-one (DC18); (4-benzoylpiperazin-1-yl)(1,2-dihydroacenaphthylen-5-yl)methanone (SC03); (5-benzoylhexahydropyrrolo[3,4-c]pyrrol-2(1H)-yl)(1,2-dihydroacenaphthylen-5-yl)methanone (SC04); 4-benzoyl-1-(1,2-dihydroacenaphthylene-5-carbonyl)-2-methylpiperazine (SC06); 1-(5-benzoylhexahydropyrrolo[3,4-c]pyrrol-2(1H)-yl)-2-(7-chloro-4-methoxy-1H-pyrrolo[2,3-c]pyridin-3-yl)ethane-1,2-dione (SC07); 1-(5-benzoylhexahydropyrrolo[3,4-c]pyrrol-2(1H)-yl)-2-(4,7-dimethoxy-1H-pyrrolo[2,3-c]pyridin-3-yl)ethane-1,2-dione (SC08); 1-(4,7-dimethoxy-1H-pyrrolo[2,3-c]pyridin-3-yl)-2-(4-phenyl hexahydrocyclopenta[c]pyrrol-2(1H)-yl)ethane-1,2-dione (SC10); 1-(5-benzoylhexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC11); 1-(4-methoxy-7-(3-methyl-1H-1,2,4-triazol-1-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione (SC12); N-((1-benzoylazetidin-3-yl)methyl)-2-(4-methoxy-7-(3-methyl-1H-1,2,4-triazol-1-yl)-1H-pyrrolo[2,3-c]pyridin-3-yl)-2-oxoacetamide (SC14); 1-(4-methoxy-7-(3-methyl-1H-1,2,4-triazol-1-yl)-1H-pyrrolo[2,3-c]pyridin-3-yl)-2-(3-(3-oxo-3-phenylpropyl)azetidin-1-yl)ethane-1,2-dione (SC15); S-((1-(2-(4-methoxy-7-(3-methyl-1H-1,2,4-triazol-1-yl)-1H-pyrrolo[2,3-c]pyridin-3-yl)-2-oxoacetyl) azetidin-3-yl)methyl) benzothioate (SC16); N-(1-benzoylazetidin-3-yl)-2-(4-methoxy-7-(3-methyl-1H-1,2,4-triazol-1-yl)-1H-pyrrolo[2,3-c]pyridin-3-yl)-N-methyl-2-oxoacetamide (SC18); 1-(4-methoxy-7-(3-methyl-1H-1,2,4-triazol-1-yl)-1H-pyrrolo[2,3-c]pyridin-3-yl)-2-(1-(1-methyl-1,6-dihydropyridin-3-yl)-3a,4,6,6a-tetrahydropyrrolo[3,4-c]pyrazol-5(1H)-yl)ethane-1,2-dione (SC19); 1-(1-(1H-pyrrol-3-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione (SC20); 1-(1-(1H-imidazol-4-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione (SC21); 1-(4-methoxy-7-(3-methyl-1H-1,2,4-triazol-1-yl)-1H-pyrrolo[2,3-c]pyridin-3-yl)-2-(1-(4-methyl-1H-pyrrol-2-yl)-3a,4,6,6a-tetrahydropyrrolo[3,4-c]pyrazol-5(1H)-yl)ethane-1,2-dione (SC22); 1-(4-methoxy-7-(3-methyl-1H-1,2,4-triazol-1-yl)-1H-pyrrolo[2,3-c]pyridin-3-yl)-2-(1-(5-methyl-1H-imidazol-4-yl)-3a,4,6,6a-tetrahydropyrrolo[3,4-c]pyrazol-5(1H)-yl)ethane-1,2-dione (SC23); 1-(4-methoxy-7-(3-methyl-1H-1,2,4-triazol-1-yl)-1H-pyrrolo[2,3-c]pyridin-3-yl)-2-(1-(6-methylpyridin-2-yl)-3a,4,6,6a-tetrahydropyrrolo[3,4-c]pyrazol-5(1H)-yl)ethane-1,2-dione (SC24); 1-(1-(1H-pyrrol-2-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione (SC25); 1-(5-(cyclohex-1-ene-1-carbonyl)hexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione (SC26); 1-(8-benzoyl-2,8-diazaspiro[4.5]decan-2-yl)-2-(4-methoxy-7-(3-methyl-1H-1,2,4-triazol-1-yl)-1H-pyrrolo[2,3-c]pyridin-3-yl)ethane-1,2-dione (SC27); N-(3-benzoyl-3-azabicyclo[3.1.0]hexan-6-yl)-3-(4-methoxy-7-(3-methyl-H-1,2,4-triazol-1-yl)-1H-pyrrolo[2,3-c]pyridin-3-yl)-2,3-dioxopropanamide (SC28); 1-(6-(cyclohex-1-ene-1-carbonyl)-2,6-diazaspiro[3.4]octan-2-yl)-2-(4-methoxy-7-(3-methyl-1H-1,2,4-triazol-1-yl)-1H-pyrrolo[2,3-c]pyridin-3-yl)ethane-1,2-dione (SC29); 1-(4-fluoro-7-(1H-1,2,3-triazol-1-yl)-1H-pyrrolo[2,3-c]pyridin-3-yl)-2-(1-phenyl-3a,4,6,6a-tetrahydropyrrolo [3,4-c]pyrazol-5(1H)-yl) ethane-1,2-dione (SC38); 1-(4-fluoro-7-(3-methyl-1H-1,2,4-triazol-1-yl)-1H-pyrrolo[2,3-c]pyridin-3-yl)-2-(1-(1-phenyl-1H-tetrazol-5-yl)-3a,4,6,6a-tetrahydro pyrrolo[3,4-c]pyrazol-5(1H)-yl)ethane-1,2-dione (SC39); 1-(1-benzoyl-1,6-diazaspiro [2.5]octan-6-yl)-2-(4-methoxy-7-(3-methyl-1H-1,2,4-triazol-1-yl)-1H-pyrrolo[2,3-c]pyridin-3-yl) ethane-1,2-dione (SC41); 1-(4-methoxy-7-(3-methyl-1H-1,2,4-triazol-1-yl)-1H-pyrrolo [2,3-c]pyridin-3-yl)-2-(1-(1-phenyl-1H-tetrazol-5-yl)-1,6-diazaspiro[2.5]octan-6-yl) ethane-1,2-dione (SC42); 1-(5-benzoylhexahydropyrrolo[3,4-c]pyrrol-2(1H)-yl)-2-(4-fluoro-7-(2H-1,2,3-triazol-2-yl)-1H-pyrrolo[2,3-c]pyridin-3-yl)ethane-1,2-dione (SC43); 1-(4-fluoro-7-(2H-1,2,3-triazol-2-yl)-1H-pyrrolo[2,3-c]pyridin-3-yl)-2-(1-phenyl-3a,4,6,6a-tetrahydro pyrrolo[3,4-c]pyrazol-5(1H)-yl)ethane-1,2-dione (SC44); N-((1-(2-(4-methoxy-7-(3-methyl-1H-1,2,4-triazol-1-yl)-1H-pyrrolo[2,3-c]pyridin-3-yl)-2-oxoacetyl)-1,2,3,6-tetrahydropyridin-4-yl)methyl)benzamide (SC45); a salt or solvate thereof and any mixtures thereof.

In another aspect, the present invention contemplates a pharmaceutical composition comprising at least one compound of the invention and at least one pharmaceutically acceptable carrier.

The structures and corresponding names of selected compounds of the invention are illustrated in Table 1.

TABLE 1

| Structure | Name | Cpd ID |
|---|---|---|
| 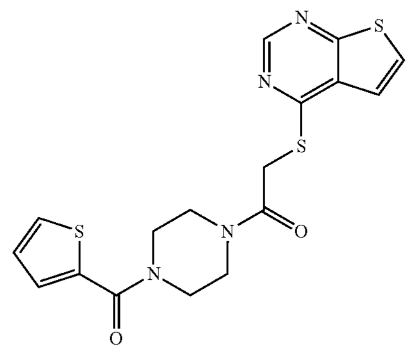 [SMILES: O=C(CSc1ncnc2sccc12)N1CCN(C(=O)c2cccs2)CC1] | 2-(thieno[2,3-d]pyrimidin-4-ylthio)-1-(4-(thiophene-2-carbonyl)piperazin-1-yl)ethan-1-one | DC04 |
| 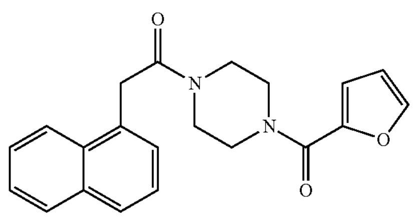 [SMILES: O=C(Cc1cccc2ccccc12)N1CCN(C(=O)c2ccco2)CC1] | 1-(4-(furan-2-carbonyl)piperazin-1-yl)-2-(naphthalen-1-yl)ethan-1-one | DC08 |
| 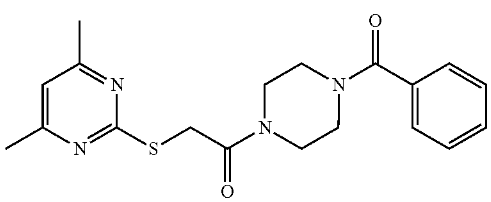 [SMILES: Cc1cc(C)nc(SCC(=O)N2CCN(C(=O)c3ccccc3)CC2)n1] | 1-(4-benzoylpiperazin-1-yl)-2-((4,6-dimethylpyrimidin-2-yl)thio)ethan-1-one | DC10 |
| 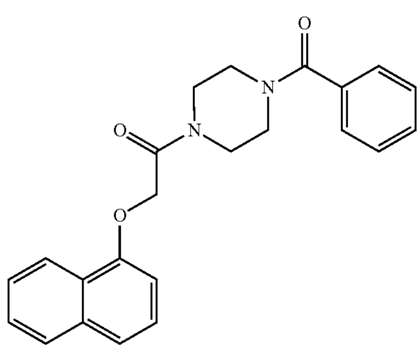 [SMILES: O=C(COc1cccc2ccccc12)N1CCN(C(=O)c2ccccc2)CC1] | 1-(4-benzoylpiperazin-1-yl)-2-(naphthalen-1-yloxy)ethan-1-one | DC18 |
| 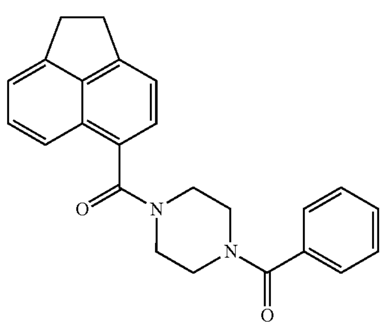 [SMILES: O=C(c1ccccc1)N1CCN(C(=O)c2ccc3c4c(cccc24)CC3)CC1] | (4-benzoylpiperazin-1-yl)(1,2-dihydroacenaphthylen-5-yl)methanone | SC03 |

TABLE 1-continued

| Structure | Name | Cpd ID |
|---|---|---|
| 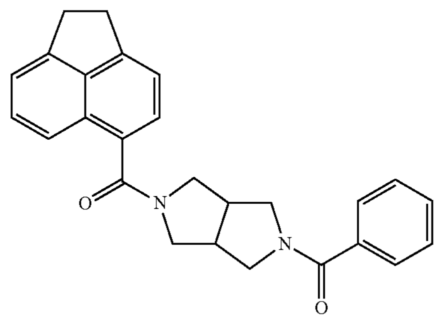 [SMILES: O=C(c1ccccc1)N1CC2CN(C(=O)c3ccc4c5c(cccc35)CC4)CC2C1] | (5-benzoylhexahydropyrrolo[3,4-c]pyrrol-2(1H)-yl)(1,2-dihydroacenaphthylen-5-yl)methanone | SC04 |
| 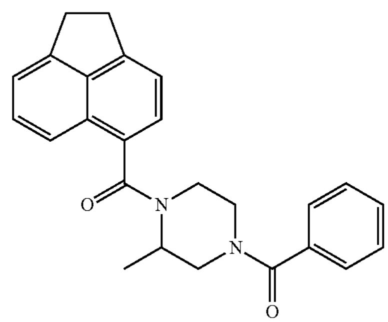 [SMILES: CC1CN(C(=O)c2ccccc2)CCN1C(=O)c1ccc2c3c(cccc13)CC2] | 4-benzoyl-1-(1,2-dihydroacenaphthylene-5-carbonyl)-2-methylpiperazine | SC06 |
| 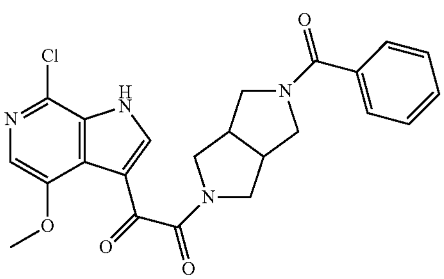 [SMILES: COc1cnc(Cl)c2[nH]cc(C(=O)C(=O)N3CC4CN(C(=O)c5ccccc5)CC4C3)c12] | 1-(5-benzoylhexahydropyrrolo[3,4-c]pyrrol-2(1H)-yl)-2-(7-chloro-4-methoxy-1H-pyrrolo[2,3-c]pyridin-3-yl)ethane-1,2-dione | SC07 |
| 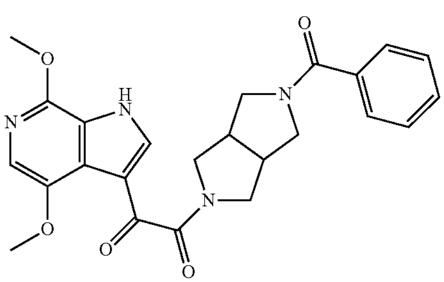 [SMILES: COc1ncc(OC)c2c(C(=O)C(=O)N3CC4CN(C(=O)c5ccccc5)CC4C3)c[nH]c12] | 1-(5-benzoylhexahydropyrrolo[3,4-c]pyrrol-2(1H)-yl)-2-(4,7-dimethoxy-1H-pyrrolo[2,3-c]pyridin-3-yl)ethane-1,2-dione | SC08 |
| 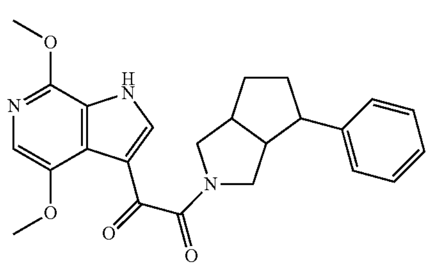 [SMILES: COc1ncc(OC)c2c(C(=O)C(=O)N3CC4CCC(c5ccccc5)C4C3)c[nH]c12] | 1-(4,7-dimethoxy-1H-pyrrolo[2,3-c]pyridin-3-yl)-2-(4-phenylhexahydrocyclopenta[c]pyrrol-2(1H)-yl)ethane-1,2-dione | SC10 |

TABLE 1-continued

| Structure | Name | Cpd ID |
|---|---|---|
| 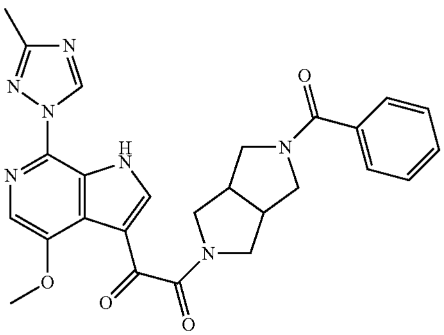 [SMILES: COc1cnc(-n2cnc(C)n2)c2[nH]cc(C(=O)C(=O)N3CC4CN(C(=O)c5ccccc5)CC4C3)c12] | 1-(5-benzoylhexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione | SC11 |
| 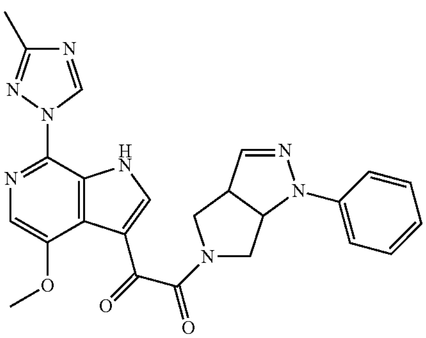 [SMILES: COc1cnc(-n2cnc(C)n2)c2[nH]cc(C(=O)C(=O)N3CC4C=NN(c5ccccc5)C4C3)c12] | 1-(4-methoxy-7-(3-methyl-1H-1,2,4-triazol-1-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione | SC12 |
| 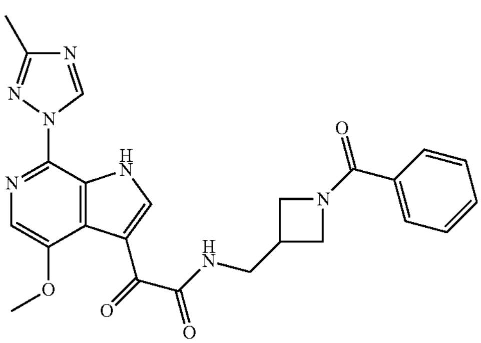 [SMILES: COc1cnc(-n2cnc(C)n2)c2[nH]cc(C(=O)C(=O)NCC3CN(C(=O)c4ccccc4)C3)c12] | N-((1-benzoylazetidin-3-yl)methyl)-2-(4-methoxy-7-(3-methyl-1H-1,2,4-triazol-1-yl)-1H-pyrrolo[2,3-c]pyridin-3-yl)-2-oxoacetamide | SC14 |
| 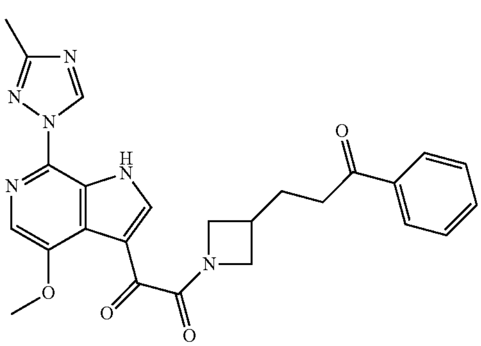 [SMILES: COc1cnc(-n2cnc(C)n2)c2[nH]cc(C(=O)C(=O)N3CC(CCC(=O)c4ccccc4)C3)c12] | 1-(4-methoxy-7-(3-methyl-1H-1,2,4-triazol-1-yl)-1H-pyrrolo[2,3-c]pyridin-3-yl)-2-(3-(3-oxo-3-phenylpropyl)azetidin-1-yl)ethane-1,2-dione | SC15 |

TABLE 1-continued

| Structure | Name | Cpd ID |
|---|---|---|
| 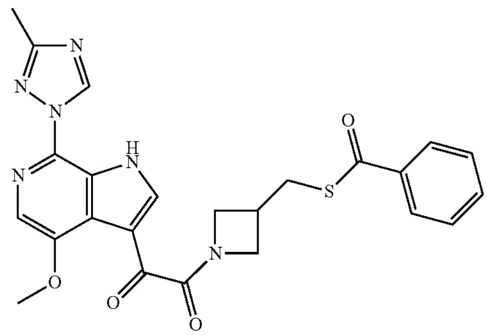 | S-((1-(2-(4-methoxy-7-(3-methyl-1H-1,2,4-triazol-1-yl)-1H-pyrrolo[2,3-c]pyridin-3-yl)-2-oxoacetyl)azetidin-3-yl)methyl)benzothioate | SC16 |
| 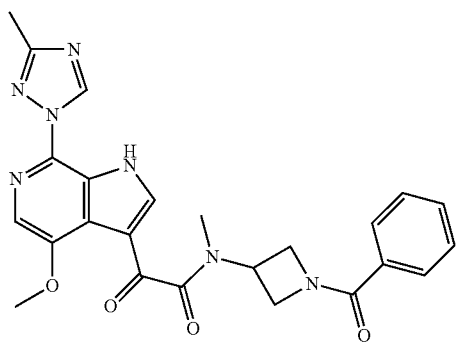 [SMILES: COc1cnc(-n2cnc(C)n2)c2[nH]cc(C(=O)C(=O)N(C)C3CN(C(=O)c4ccccc4)C3)c12] | N-(1-benzoylazetidin-3-yl)-2-(4-methoxy-7-(3-methyl-1H-1,2,4-triazol-1-yl)-1H-pyrrolo[2,3-c]pyridin-3-yl)-N-methyl-2-oxoacetamide | SC18 |
| 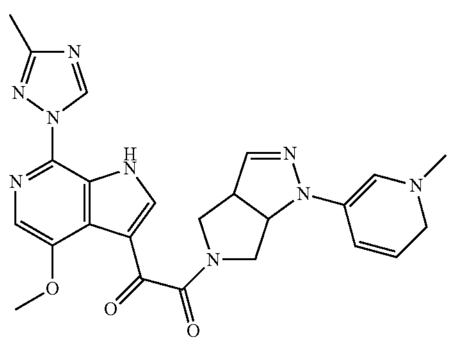 | 1-(4-methoxy-7-(3-methyl-1H-1,2,4-triazol-1-yl)-1H-pyrrolo[2,3-c]pyridin-3-yl)-2-(1-(1-methyl-1,6-dihydropyridin-3-yl)-3a,4,6,6a-tetrahydropyrrolo[3,4-c]pyrazol-5(1H)-yl)ethane-1,2-dione | SC19 |
| 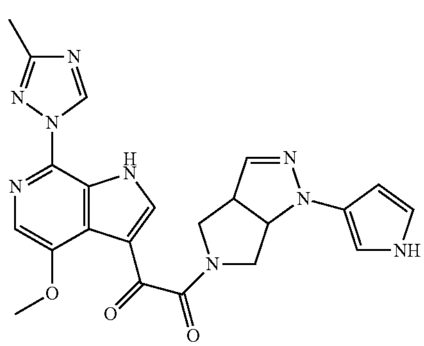 [SMILES: COc1cnc(-n2cnc(C)n2)c2[nH]cc(C(=O)C(=O)N3CC4C=NN(c5cc[nH]c5)C4C3)c12] | 1-(1-(1H-pyrrol-3-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione | SC20 |

TABLE 1-continued

| Structure | Name | Cpd ID |
|---|---|---|
| 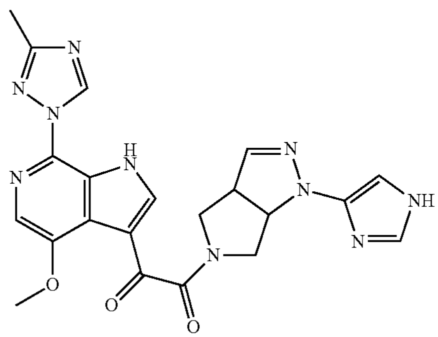 [SMILES: COc1cnc(-n2cnc(C)n2)c2[nH]cc(C(=O)C(=O)N3CC4C=NN(c5c[nH]cn5)C4C3)c12] | 1-(1-(1H-imidazol-4-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione | SC21 |
| 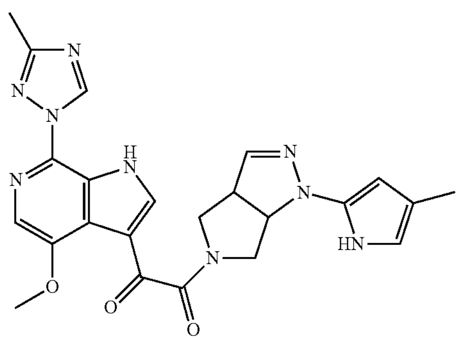 | 1-(4-methoxy-7-(3-methyl-1H-1,2,4-triazol-1-yl)-1H-pyrrolo[2,3-c]pyridin-3-yl)-2-(1-(4-methyl-1H-pyrrol-2-yl)-3a,4,6,6a-tetrahydropyrrolo[3,4-c]pyrazol-5(1H)-yl)ethane-1,2-dione | SC22 |
| 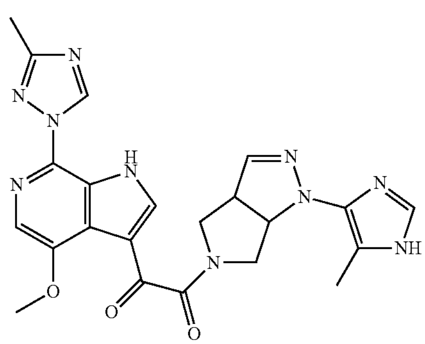 [SMILES: COc1cnc(-n2cnc(C)n2)c2[nH]cc(C(=O)C(=O)N3CC4C=NN(c5nc[nH]c5C)C4C3)c12] | 1-(4-methoxy-7-(3-methyl-1H-1,2,4-triazol-1-yl)-1H-pyrrolo[2,3-c]pyridin-3-yl)-2-(1-(5-methyl-1H-imidazol-4-yl)-3a,4,6,6a-tetrahydropyrrolo[3,4-c]pyrazol-5(1H)-yl)ethane-1,2-dione | SC23 |
| 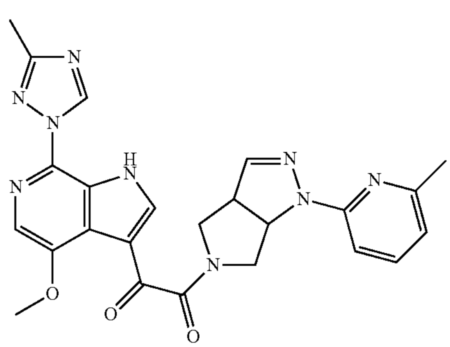 | 1-(4-methoxy-7-(3-methyl-1H-1,2,4-triazol-1-yl)-1H-pyrrolo[2,3-c]pyridin-3-yl)-2-(1-(6-methylpyridin-2-yl)-3a,4,6,6a-tetrahydropyrrolo[3,4-c]pyrazol-5(1H)-yl)ethane-1,2-dione | SC24 |

TABLE 1-continued

| Structure | Name | Cpd ID |
|---|---|---|
| 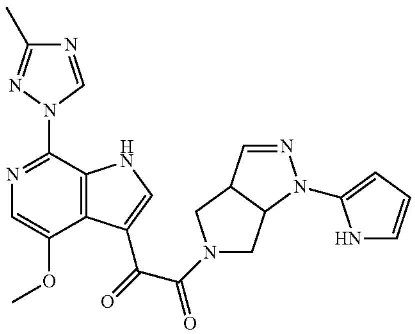 [SMILES: COc1cnc(-n2cnc(C)n2)c2[nH]cc(C(=O)C(=O)N3CC4C=NN(c5ccc[nH]5)C4C3)c12] | 1-(1-(1H-pyrrol-2-yl)-3a,4,6,6a-tetrahydropyrrolo[3,4-c]pyrazol-5(1H)-yl)-2-(4-methoxy-7-(3-methyl-1H-1,2,4-triazol-1-yl)-1H-pyrrolo[2,3-c]pyridin-3-yl)ethane-1,2-dione | SC25 |
| 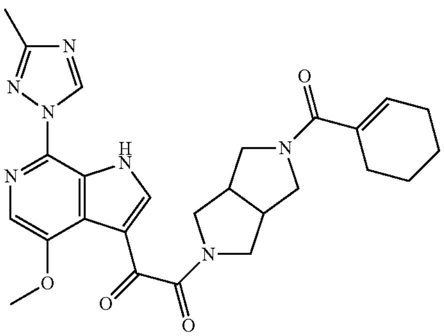 [SMILES: COc1cnc(-n2cnc(C)n2)c2[nH]cc(C(=O)C(=O)N3CC4CN(C(=O)C5=CCCCC5)CC4C3)c12] | 1-(5-(cyclohex-1-ene-1-carbonyl)hexahydropyrrolo[3,4-c]pyrrol-2(1H)-yl)-2-(4-methoxy-7-(3-methyl-1H-1,2,4-triazol-1-yl)-1H-pyrrolo[2,3-c]pyridin-3-yl)ethane-1,2-dione | SC26 |
| 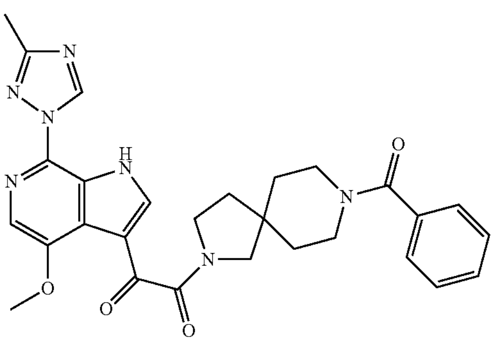 [SMILES: COc1cnc(-n2cnc(C)n2)c2[nH]cc(C(=O)C(=O)N3CCC4(CCN(C(=O)c5ccccc5)CC4)C3)c12] | 1-(8-benzoyl-2,8-diazaspiro[4.5]decan-2-yl)-2-(4-methoxy-7-(3-methyl-1H-1,2,4-triazol-1-yl)-1H-pyrrolo[2,3-c]pyridin-3-yl)ethane-1,2-dione | SC27 |
| 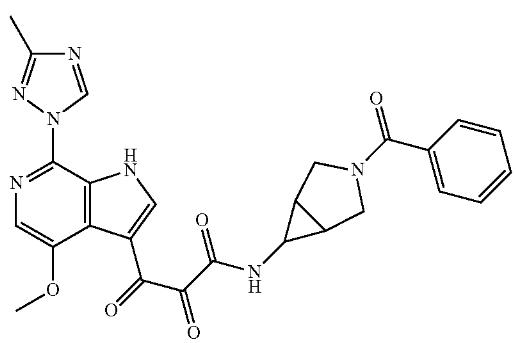 [SMILES: COc1cnc(-n2cnc(C)n2)c2[nH]cc(C(=O)C(=O)C(=O)NC3C4CN(C(=O)c5ccccc5)CC43)c12] | N-(3-benzoyl-3-azabicyclo[3.1.0]hexan-6-yl)-3-(4-methoxy-7-(3-methyl-1H-1,2,4-triazol-1-yl)-1H-pyrrolo[2,3-c]pyridin-3-yl)-2,3-dioxopropanamide | SC28 |

TABLE 1-continued

| Structure | Name | Cpd ID |
|---|---|---|
| 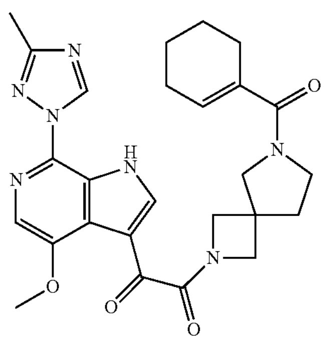 [SMILES: COc1cnc(-n2cnc(C)n2)c2[nH]cc(C(=O)C(=O)N3CC4(CCN(C(=O)C5=CCCCC5)C4)C3)c12] | 1-(6-(cyclohex-1-ene-1-carbonyl)-2,6-diazaspiro[3.4]octan-2-yl)-2-(4-methoxy-7-(3-methyl-1H-1,2,4-triazol-1-yl)-1H-pyrrolo[2,3-c]pyridin-3-yl)ethane-1,2-dione | SC29 |
| 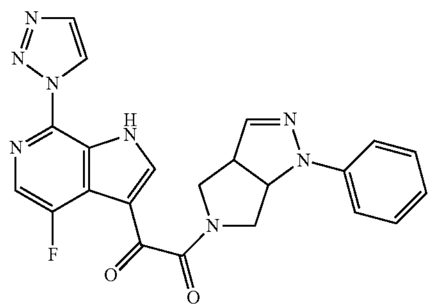 [SMILES: O=C(C(=O)N1CC2C=NN(c3ccccc3)C2C1)c1c[nH]c2c(-n3ccnn3)ncc(F)c12] | 1-(4-fluoro-7-(1H-1,2,3-triazol-1-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione | SC38 |
| 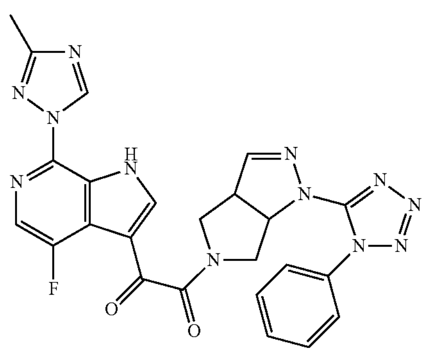 [SMILES: Cc1ncn(-c2ncc(F)c3c(C(=O)C(=O)N4CC5C=NN(c6nnnn6-c6ccccc6)C5C4)c[nH]c23)n1] | 1-(4-fluoro-7-(3-methyl-1H-1,2,4-triazol-1-yl)-1H-pyrrolo[2,3-c]pyridin-3-yl)-2-(1-(1-phenyl-1H-tetrazol-5-yl)-3a,4,6,6a-tetrahydropyrrolo[3,4-c]pyrazol-5(1H)-yl)ethane-1,2-dione | SC39 |
| 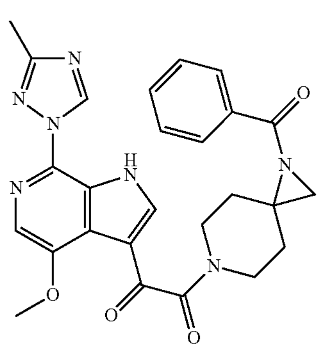 [SMILES: COc1cnc(-n2cnc(C)n2)c2[nH]cc(C(=O)C(=O)N3CCC4(CC3)CN4C(=O)c3ccccc3)c12] | 1-(1-benzoyl-1,6-diazaspiro[2.5]octan-6-yl)-2-(4-methoxy-7-(3-methyl-1H-1,2,4-triazol-1-yl)-1H-pyrrolo[2,3-c]pyridin-3-yl)ethane-1,2-dione | SC41 |

TABLE 1-continued

| Structure | Name | Cpd ID |
|---|---|---|
| 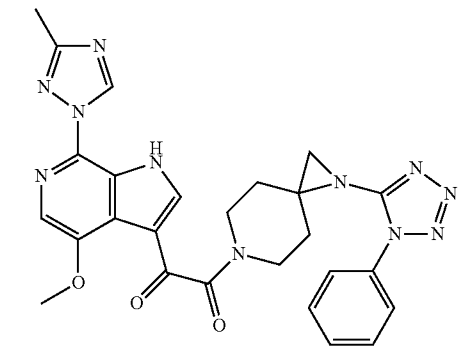 [SMILES: COc1cnc(-n2cnc(C)n2)c2[nH]cc(C(=O)C(=O)N3CCC4(CC3)CN4c3nnnn3-c3ccccc3)c12] | 1-(4-methoxy-7-(3-methyl-1H-1,2,4-triazol-1-yl)-1H-pyrrolo[2,3-c]pyridin-3-yl)-2-(1-(1-phenyl-1H-tetrazol-5-yl)-1,6-diazaspiro[2.5]octan-6-yl)ethane-1,2-dione | SC42 |
| 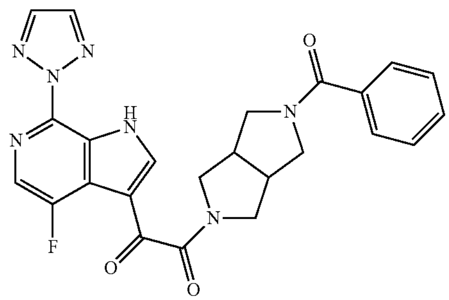 [SMILES: O=C(C(=O)N1CC2CN(C(=O)c3ccccc3)CC2C1)c1c[nH]c2c(-n3nccn3)ncc(F)c12] | 1-(5-benzoylhexahydropyrrolo[3,4-c]pyrrol-2(1H)-yl)-2-(4-fluoro-7-(2H-1,2,3-triazol-2-yl)-1H-pyrrolo[2,3-c]pyridin-3-yl)ethane-1,2-dione | SC43 |
| 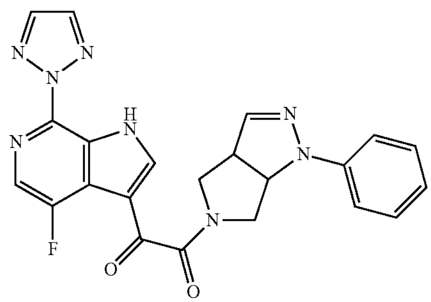 [SMILES: O=C(C(=O)N1CC2C=NN(c3ccccc3)C2C1)c1c[nH]c2c(-n3nccn3)ncc(F)c12] | 1-(4-fluoro-7-(2H-1,2,3-triazol-2-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione | SC44 |
| 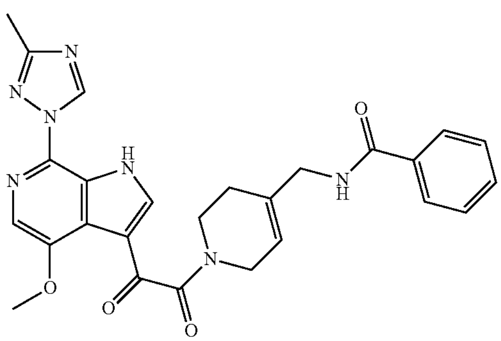 [SMILES: COc1cnc(-n2cnc(C)n2)c2[nH]cc(C(=O)C(=O)N3CC=C(CNC(=O)c4ccccc4)CC3)c12] | N-((1-(2-(4-methoxy-7-(3-methyl-1H-1,2,4-triazol-2-yl)-1H-pyrrolo[2,3-c]pyridin-3-yl)-2-oxoacetyl)-1,2,3,6-tetrahydropyridin-4-yl)methyl)benzamide | SC45 |

Preparation of Compounds of the Invention

Compounds of formula (I) may be prepared by the general schemes described elsewhere herein, using the synthetic method known by those skilled in the art. The examples provided herein illustrate non-limiting embodiments of the invention.

The compounds of the invention may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates. Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react. Typically blocking/protecting groups may be selected from:

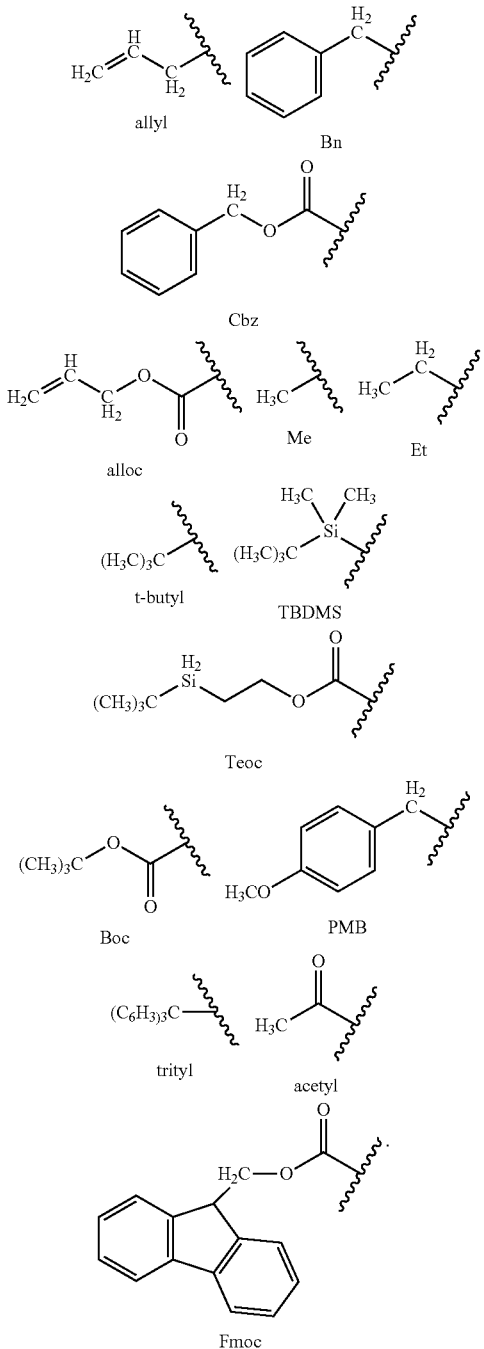

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods

The invention includes a method of treating or preventing an HIV-1 infection in a subject in need thereof. The method comprises administering to the subject a therapeutically effective amount of a compound of the invention. In one embodiments, the method further comprises administering to the subject an additional therapeutic agent.

In certain embodiments, administering the compound of the invention to the subject allows for administering a lower dose of the therapeutic agent compared to the dose of the therapeutic agent alone that is required to achieve similar results in treating or preventing an HIV-1 infection in the subject. For example, in certain embodiments, the compound of the invention enhances the anti-HIV-1 activity of the additional therapeutic compound, thereby allowing for a lower dose of the therapeutic compound to provide the same effect.

In certain embodiments, the compound of the invention and the therapeutic agent are co-administered to the subject. In other embodiments, the compound of the invention and the therapeutic agent are coformulated and co-administered to the subject.

In certain embodiments, the methods described herein further comprise inhibiting the binding of gp120 to a G-protein coupled receptor, a chemokine co-receptor, or a co-receptor surrogate antibody. In other embodiments, the compound described herein is used as a research tool to evaluate the binding of gp120 to a G-protein coupled receptor, a chemokine co-receptor, or a co-receptor surrogate antibody.

In certain embodiments, the subject is a mammal. In other embodiments, the mammal is a human.

Combination Therapies

The compounds useful within the methods of the invention may be used in combination with one or more additional compounds useful for treating an HIV infection. These additional compounds may comprise compounds that are commercially available or synthetically accessible to those skilled in the art. These additional compounds are known to treat, prevent, or reduce the symptoms of an HIV infection.

In non-limiting examples, the compounds useful within the invention may be used in combination with one or more of the following anti-HIV drugs:

HIV Combination Drugs: efavirenz, emtricitabine or tenofovir disoproxil fumarate (Atripla®/BMS, Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

Entry and Fusion Inhibitors: maraviroc (Celsentri®, Selzentry®/Pfizer); pentafuside or enfuvirtide (Fuzeon®/Roche, Trimeris).

Integrase Inhibitors: raltegravir or MK-0518 (Isentress®/Merck).

Non-Nucleoside Reverse Transcriptase Inhibitors: delavirdine mesylate or delavirdine (Rescriptor®/Pfizer); nevirapine (Viramune®/Boehringer Ingelheim); stocrin or efavirenz (Sustiva®/BMS); etravirine (Intelence®/Tibotec).

Nucleoside Reverse Transcriptase Inhibitors: lamivudine or 3TC (Epivir®/GSK); FTC, emtricitabina or coviracil (Emtriva®/Gilead); abacavir (Ziagen®/GSK); zidovudina, ZDV, azidothymidine or AZT (Retrovir®/GSK); ddI, dideoxyinosine or didanosine (Videx®/BMS); abacavir sulfate plus lamivudine (Epzicom®/GSK); stavudine, d4T, or estavudina (Zerit®/BMS); tenofovir, PMPA prodrug, or tenofovir disoproxil fumarate (Viread®/Gilead).

Protease Inhibitors: amprenavir (Agenerase®/GSK, Vertex); atazanavir (Reyataz®/BMS); tipranavir (Aptivus®/Boehringer Ingelheim); darunavir (Prezist®/Tibotec); fosamprenavir (Telzir®, Lexiva®/GSK, Vertex); indinavir sulfate (Crixivan®/Merck); saquinavir mesylate (Invirase®/Roche); lopinavir or ritonavir (Kaletra®/Abbott); nelfinavir mesylate (Viracept®/Pfizer); ritonavir (Norvir®/Abbott).

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of an HIV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the invention to a patient, preferably a mammal, more preferably a human, may be carried out using known procedures, at dosages and for periods of time effective to treat an HIV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat an HIV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of an HIV infection in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of an HIV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the invention depends on the age, sex and weight of the patient, the current medical condition of the patient and the progression of an HIV infection in the patient being treated. The skilled artisan is able to determine appropriate dosages depending on these and other factors.

A suitable dose of a compound of the invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the invention. Moreover, all values that fall within these ranges, as well as the upper or lower limits of a range of values, are also contemplated by the present application.

The following examples further illustrate aspects of the invention. However, they are in no way a limitation of the teachings or disclosure of the invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods and Materials
Cells

Human embryonic kidney 293T cells were cultured in Dulbecco modified Eagle medium supplemented with 10% heat-inactivated fetal bovine serum, L-glutamine, and antibiotics. Human astroglioma U87 cells stably transfected for the expression of CD4 and CXCR4 (Bjorndal, et al., 1997, J Virol 71:7478) were cultured in Dulbecco modified Eagle medium supplemented as above plus puromycin and G418 (Geneticin, Gibco BRL Life Technologies, Grand Island, N.Y.).

Production of Pseudotypes

Single-round infectious envelope-pseudotyped luciferase-reporter viruses were produced in 293T cells co-transfected by calcium phosphate precipitation (Profection Mammalian Transfection System) with the envelope-deficient HIV-1 NL4-3 vector (pNL4-3-LucR$^+$E$^-$; Connor, et al., 1995, Virology 206:935), which carries the luciferase-reporter gene; and either the HIV-1 YU-2, JR-CSF, HxBc2-envelope expressing vector (obtained from Kathleen Page and Dan Littman through the AIDS Research and Reference Reagent Program, Division of AIDS, NIAID, NIH). After 6 h of incubation at 37° C., the DNA-containing medium was removed, cells were washed, and fresh medium was added. Supernatants containing the envelope-pseudotyped viruses were collected 2 days later, clarified by centrifugation, aliquoted, and stored at −80° C. until use. Pseudotype stocks were quantified by p24$^{gag}$ content (Advanced Bioscience Laboratories, Kensington, Md.).

Determination of Potency, Therapeutic Spectrum, and Specificity of Compounds

Among the several in vitro assays that test disruption of the interactions that Env participates in to accomplish fusion, the activity of the entry inhibitor compounds may be assessed by demonstrating their antiviral effect. Without wishing to be limited by any theory, the functional oligomeric HIV-1 Env be unambiguously assessed in this context.

A 3-tiered approach is used to test the potency of novel entry inhibitor compounds developed within this study. First, potency is assessed using the single-round infection assay (Cocklin, et al., 2007, J. Virol. 81:3645-3648; Connor, et al., 1995, Virol. 206:935-944; He, et al., 1995, J. Virol. 69:6705-6711). In one aspect, the assay is relatively rapid, taking only the amount of time needed to complete one round of replication. As the envelope glycoproteins in these assays are molecularly cloned, precise sequence information is available on all of the viral components in the assay. Moreover, since there are no subsequent rounds of infection, there is no alteration of the Env sequences during the course of the assay, and sensitivities/insensitivities can be directly correlated with specific sequence elements. The assay is amenable to inclusion of various HIV-1 envelope glycoproteins to assess the therapeutic spectrum of the antiviral activity of a given compound. Furthermore, the recombinant viruses used can be pseudotyped with irrelevant envelope glycoproteins (from heterologous viruses) to assist in the assessment of specificity.

Second, high potency compounds are assessed in a fully infectious HIV-1 replication assay using primary human PBMCs (Kortagere, et al., 2012, J. Virol. 86:8472-8481; Zentner, et al., 2013, Chem Med Chem 8:426-432; Zentner, et al., 2013, Bioorg. & Med. Chem. Lett. 23:1132-1135). This is used to further assess therapeutic spectrum and to evaluate toxicity to primary human cells.

Third, the compounds are assayed for their ability to stop cell-cell fusion and cell-cell transmission.

Figure 9:
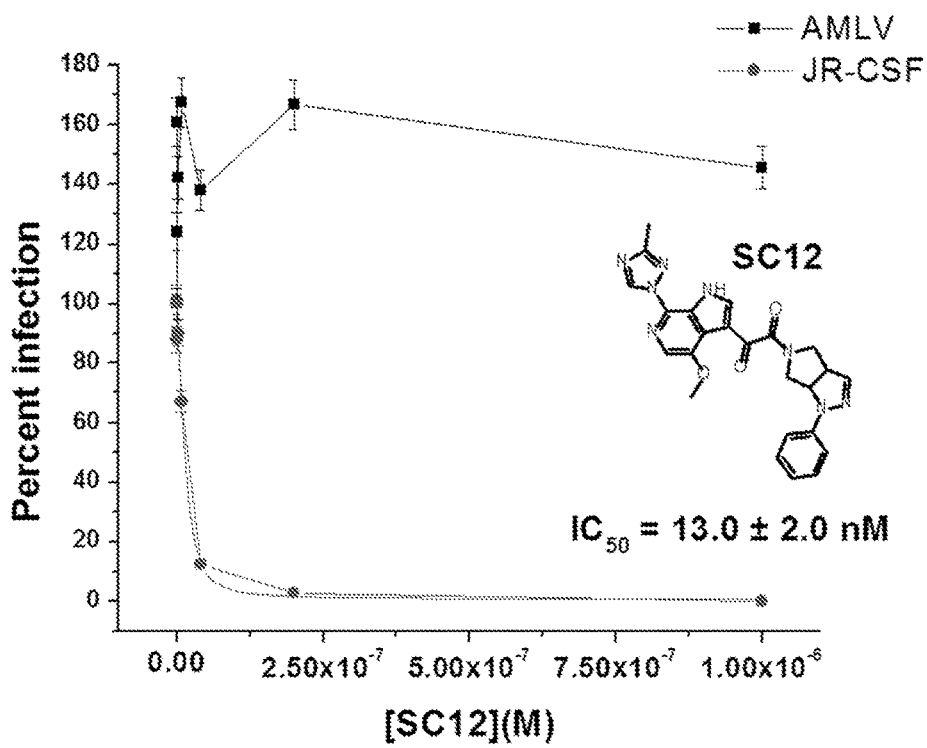
FIG. 9 is a graph illustrating the effects of compound SC12 on the infection of U87-CD4-CCR5 cells by recombinant luciferase-expressing HIV-1 bearing the envelope glycoproteins of the HIV-1$_{JR\text{-}CSF}$ strain and amphotropic murine leukemia virus (AMLV). Virus infection is expressed as the percentage of infection (measured by luciferase activity in the target cells) observed in the presence of compound relative to the level of infection observed in the absence of the compound. The data from three replicates are shown. The chemical structure of compound SC12 is shown inset.

Single-Round Infection Assays:

Single-round infections of target cells using recombinant HIV-1 viruses expressing easily assayed and quantifiable markers can be used to study the inhibition of HIV-1 infection. In every instance in which standard antiviral assays using replication-competent viruses were employed in addition to these single-round assays, the results obtained were comparable, and therefore the use of single-round assays as an initial screen allows detection of any activity of the test compounds in inhibiting (or enhancing) the early phase of HIV-1 infection. The details of the single-round HIV-1 infection assay have been published (Cocklin, S., et al., 2007, J. Virol. 81:3645-3648; Connor, et al., 1995, Virol. 206:935-944; He, et al., 1995, J. Virol. 69:6705-6711). Briefly, the system relies upon the generation of recombinant viruses from a two plasmid system. The first plasmid contains the NL4-3 genome in which the env gene has been rendered non-functional, and the firefly luciferase gene has been inserted in the coding sequence of nef. The second plasmid codes for the Env protein, either from HIV-1 or from a heterologous virus. Recombinant HIV-1 viruses are produced by transfection of 293T cells with the two plasmids, with Env plasmids complementing in trans the defective env gene in the backbone NL4-3 plasmid creating infectious particles capable of only sustaining one round of infection. Recombinant virions containing different HIV-1 envelope glycoproteins from the JR-FL, JR-CSF, YU-2, 89.6, and HXBc2 isolates are produced. These envelope glycoproteins were derived from macrophage-tropic primary HIV-1 isolates (JR-FL, JR-CSF, and YU-2) that use CCR5 as coreceptor, from a laboratory-adapted HIV-1 isolate (HxBc2) that utilizes CXCR4 as coreceptor, and from the dual-tropic HIV-1 isolates (89.6) that can use either CXCR4 or CCR5 (Doranz, et al., 1996, Cell 85:1149-1158). In addition, because the HIV-2 and SIVmac envelope glycoproteins can be functionally incorporated into HIV-1 particles (Marcon, et al., 1997, J. Virol. 71:2522:2527), these envelope glycoproteins can also be tested. Additional specificity controls include HIV-1 recombinant viruses pseudotyped with the amphotropic murine leukemia virus (AMLV) or vesicular stomatitis virus (VSV) envelope glycoproteins (Hofmann, et al., 1999, J. Virol. 73:10020-10028). FIG. 9 shows potency/specificity assessment of compound SC12 using the single-round infection assay.

U87-CD4/CCR5 or U87-CD4/CXCR4 cells were seeded at a density of $1.2 \times 10^4$ cells per well in 96 well luminometer-compatible tissue culture plates. The following day, cells were infected with 20 ng of p24 of pseudotyped virus per well with compounds or DMSO. Prior to addition of virus, compounds were diluted between six and nine times (1:10 or 1:5 dilution, respectively). Each dilution of compound was applied on a plate in triplicate. Forty eight hours later, cells were lysed with 50 µl of reporter lysis buffer (Promega) and luciferase activity was measured in GloMax 96 Microplate Luminometer (Promega). Percent infection was determined by the ratio of luciferase activity in compound treated wells versus DMSO treated wells.

Figure 10:
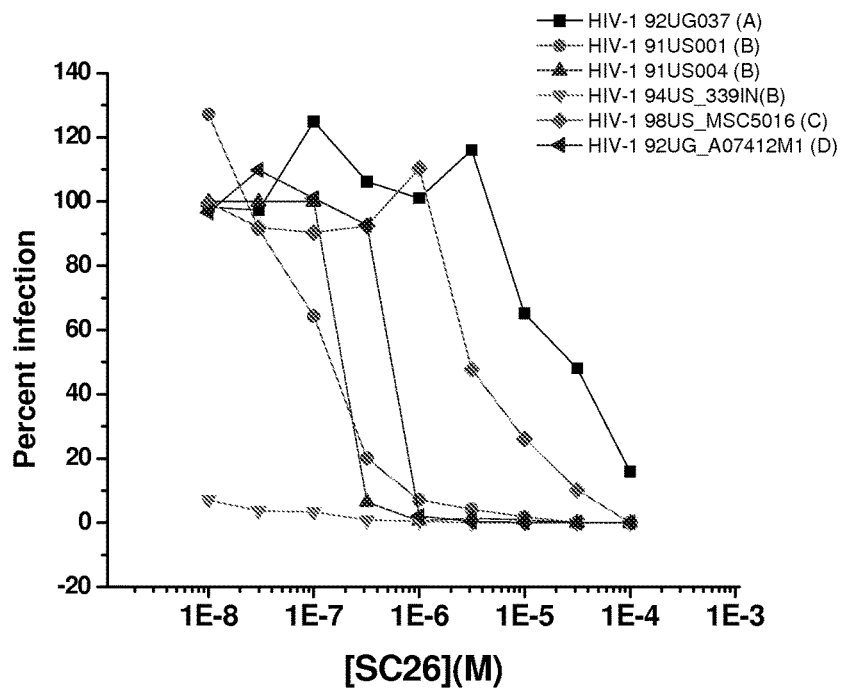
FIG. 10 is a graph illustrating the effect of compound SC26 on the infection of primary human PBMCs by HIV-1 isolates from clades A, B, C, and D.
Figure 11:
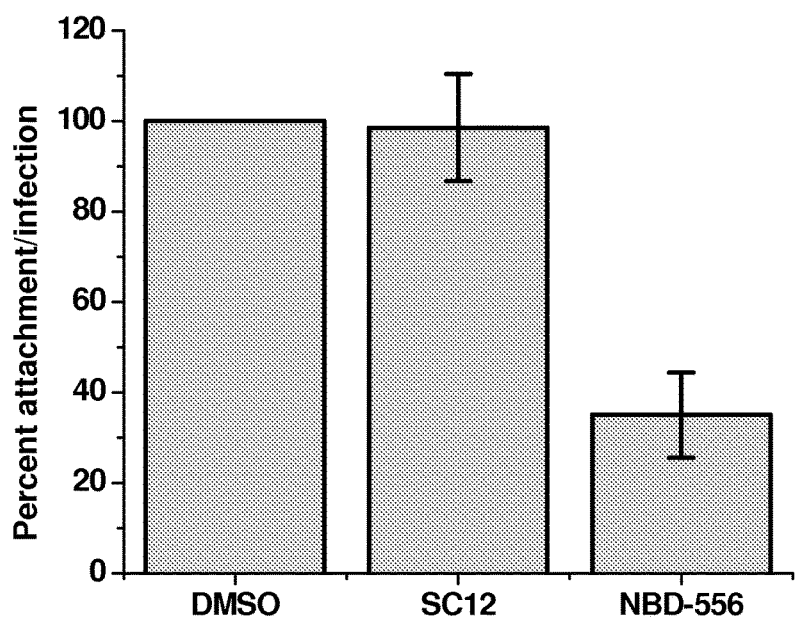
FIG. 11 is a chart illustrating % attachment of HIV-1$_{HxBc2}$ to U87-CD4+-CXCR4+ cells in the presence and absence of small molecule entry inhibitors as assessed using the temperature shift assay.

Fully Infectious HIV-1 Replication Assay Using Primary Human PBMCs:

The antiviral activity of promising test compounds identified from the single-round infection assay is verified using infectious HIV-1 derived from infectious molecular clones (IMCs) and by assessing virus replication in PBMCs. Viral stocks of three primary subtype A isolates, three primary subtype B isolates, three primary subtype C isolates, three primary subtype D, and three primary EA isolates are produced by transfection of IMCs and used to infect PBMCs. Supernatants of these cells are assessed for the amount of virus by reverse transcriptase assay. Equivalent amounts of virus are incubated with human PBMCs in the presence of increasing amounts of test compound. HIV-1 replication is then followed by periodic measurement of viral reverse transcriptase in culture supernatants (Zhao, et al., 2011, J. Biol. Chem. 286:28370-28381). FIG. 10 illustrates investigation of the therapeutic spectrum of compound SC26 using the PBMC HIV-1 infection assay.

Effectiveness of Compounds on Cell-Cell Fusion and Cell-Cell Transmission:

The effect of the novel entry inhibitors on the Env-mediated cell-cell fusion and cell-cell transmission of virus is analyzed using the novel inducible luciferase system (cell-cell fusion) and the DC-SIGN capture assay (cell-cell transmission); Herschhorn, et al., Plos one, 2011, 6:e26731, and Janas & Wu, 2009, "HIV-1 interactions with cells: From viral binding to cell-cell transmission". Curr. Prot. Cell Biol., Chapter 26, Unit 26-25.

Mechanism of Action of the Novel Entry Inhibitors

HIV-1, unlike pH-dependent viruses, uses receptor engagement to elicit the conformational changes in the viral envelope glycoproteins required for fusion (Li, et al., 2013, Antimicr. Agents Chemother. 17: 4172-4180; Adada, et al., 2013, Biochim. Biophys. Acta 5:727-737. The receptor used by HIV-1 is CD4 (Brown, 2013, J. Pharm. Sci. 102, 1742-1751). CD4 engagement induces significant conformational changes in gp120, and these changes in gp120 allow chemokine receptor binding and also result in the formation and/or exposure of the HR1 coiled coil on gp41. The effects of gp120 binding to CD4, in conjunction with binding to the chemokine receptor, initiate the conformational transitions required for membrane fusion. Therefore, both intra- and intermolecular interactions coordinate to facilitate the transduction of receptor-binding signals between the components of the Env complex and ultimately result in fusion. As such, compounds that bind HIV-1 gp120 and inhibit viral entry, such as the compounds of the present invention, may in certain embodiments block CD4 binding, chemokine receptor binding, conformational changes required for membrane fusion; or may in certain embodiments alter the nature of the gp120-gp41 interaction/association. For this specific purpose, established and developed assays are used to investigate the effect of the novel entry inhibitors on each of these aspects of HIV-1 envelope glycoprotein function.

Determine Whether Test Compounds Cause Gp120 Shedding:

Small molecules targeting the Env complex, such as the NBD-556 analogues, cause shedding of the gp120 protein rendering the virion noninfectious (Haim, et al., 2009, PLoS Pathogens 5, e1000360). In certain embodiments, the compounds of the invention cause gp120 shedding and this is how they stop entry into host cells. As such, the effects of the compounds on shedding of gp120 from the virus are determined by evaluation of the amount of particle-associated gp120 using a gp120 capture ELISA (Hammonds, et al., 2003, Virol. 314:636-649).

Figure 12:
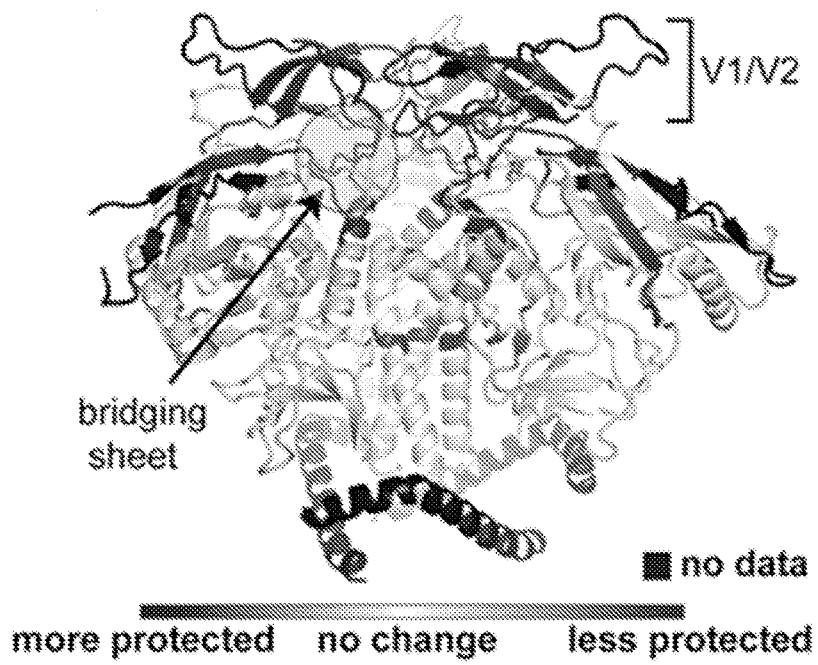
FIG. 12 is an image illustrating structural alteration of soluble Env trimmers when binding with NBD-556 (top) and BMS-378806 (bottom).
Figure 12:
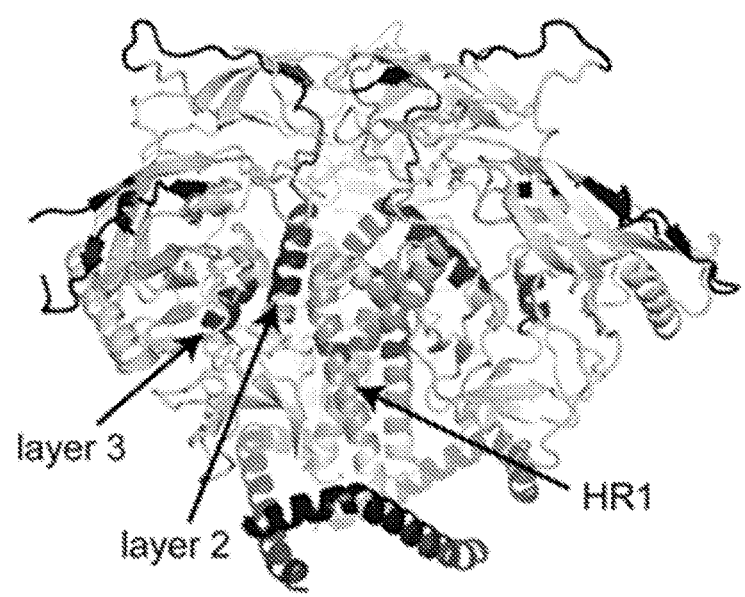

Establish Whether Test Compounds Inhibit CD4-Independent Virus:

To investigate whether the compounds of the invention disrupt the interaction of Env with CD4, CD4-independent viruses are used. While most HIV-1 viruses are dependent on the CD4 receptor for entry into cells, viruses that can infect CD4-negative cells have been derived by virus passage on CD4-negative, coreceptor-positive cells in tissue culture (Edwards, et al., 2001, J. Virol. 75:5230-5239; Haim, et al., 2011, PLoS pathogens 7, e1002101; Kolchinsky, et al., 2001, J. Virol. 75:3435-3443; Kolchinsky, et al., 2001, J. Virol. 75:2041-2050; Kolchinsky, et al., 1999, J. Virol. 73:8120-8126; LaBranche, et al., 1999, J. Virol. 73:10310-10319). Entry of such viruses into host cells is mediated by increased exposure of the co-receptor binding site through changes in the site itself or in the protein loops that in CD4-dependent viruses mask this region until bound to CD4. In certain embodiments, the compounds of the invention act solely by affecting the Env-CD4 interaction, and thus do not inhibit the entry of CD4-independent viruses. The HIV-$1_{ADA}$ S190R/N197S mutant virus is capable of entering cells that are devoid of CD4 but that express the coreceptor CCR5 (Kolchinsky, et al., 1999, J. Virol. 73:8120-8126). Therefore, the effect of this virus on the entry of CD4-negative cells is assessed. Moreover, the Env plasmids from other CD4 independent HIV-1 strains is provided. Assessing activity against such viruses help determine whether the compounds function solely by disrupting the CD4-gp120 interaction.

Determine Whether the Novel Entry Inhibitors Block Viral Attachment to the Host Cell:

In certain embodiments, the compounds of the invention function by blocking attachment of the virus to the host cell by either blocking the Env-CD4 and/or the Env-coreceptor interaction.

Temperature Shift Assay:

The entry process can be divided into two temperature-dependent stages, with receptor and coreceptor binding occurring over the temperature range 0-37° C., while the fusion process only occurs at temperatures above 25° C. (Frey, et al., 1995, J. Virol. 69:1462-1472). Based upon differential ranges in temperatures at which binding and fusion/entry occur, a novel assay was developed to detect viral attachment in the presence or absence of inhibitors. Recombinant single-round infective HIV-1 virions are incubated with permissive cells at 4° C. for 2 hours to only allow the initial receptor/coreceptor engagement. Unattached virions, and the compound, are then removed by washing the cells with cold media followed by centrifugation at 1200 rpm for 4 min at 4° C. Cells are replenished with fresh media and transferred to 37° C. After 48 hour of incubation, the level of infection is measured by a luciferase activity as in the standard single-round infection assay. Using this methodology, differences in the levels of virion binding to cells in the presence of the compounds can be determined, as it can be expected that only virions that remain bound are able to enter and infect the cells. based on this assay, compound SC12 does not appear to block viral attachment. Conversely, the small molecule CD4-mimetic NBD-556, which is known to disrupt the gp120-CD4 interaction, reduces the level of infection to 40% of vehicle (DMSO) alone (FIG. 11). Therefore, this assay can be utilized to assess whether variations of the compounds of the invention do or do not block viral attachment to the cells. Moreover, this analysis may be extended to encompass viruses that utilize CCR5 for entry.

Direct Visualization of Cellular Attachment Using GFP-Vpr-Containing HIV-1 Virions:

As a complimentary assay, the attachment of HIV-1 to permissive cells in the presence or absence of the compounds described herein is directly visualized (Stauber, et al., 1999, Biochem. Biophys. Res. Comm. 258:695-702).

Effects of Compounds on Ligand Binding and Conformational Transition with the Env Complex:

The Env complex is extremely conformationally flexible and undergoes specific rearrangements upon binding to its receptors. Binding of CD4 to a soluble Env trimer conveys two different conformational signals—opening and priming (Guttman, et al., 2014, Structure 22:974-984). Opening of the Env complex involves the repositioning of the V1/V2 and V3 loops from their interprotomer interactions within the trimer and formation and exposure of the bridging sheet. Priming involves rearrangements within the inner domain layers 2 and 3 causing allosteric changes in the fusion peptide proximal region (FPPR), HR1, and depending upon the isolate small changes in HR2. These allosteric effects of CD4 binding on gp41 are thought to "prime" the gp41 for subsequent larger scale rearrangements upon coreceptor binding.

The binding of NBD-556 or BMS-378806 to soluble Env trimers elicits specific conformational changes. As such, in certain embodiments, binding of the compounds of the invention elicit rearrangements in the Env upon interaction, exposing or burying regions of the complex and influencing its interaction with its receptors. A series of in vitro assays were developed to monitor these potential inhibitor-induced alterations to Env structure.

Effect of Compounds on sCD4-Gp120/Env Interactions:

In certain embodiments, the interaction of compounds of the invention influence the interaction of gp120/Env with the cellular receptor CD4, either positively or negatively. These potential effects are assessed in two different assays. First, soluble (s)CD4 inhibition is assessed by a slight modification to that reported by Cocklin et al (Cocklin, et al., 2007, J. Virol. 81:3645-3648). Wild-type gp120/Env is immobilized to the surface of a sensorchip. sCD4 at a given concentration is incubated with increasing amounts of compound and inhibition or enhancement is determined by a decrease or increase, respectively, in the response of the surface compared with no compound (sCD4 alone). Second, the glutaraldehyde cross-linking assays are modified (Yuan, et al., 2006, J. Virol. 80:6725-6737, Kwon, et al., 2012, Proc. Natl. Acad. Sci. USA. Cell surface-expressed Env trimers are cross-linked in the presence of the compounds. The ability of these trimers to bind sCD4 is compared with the binding ability of those trimers fixed in the absence of the compound. The D368A mutant of gp120/Env (CD4-binding defective) is used as a control.

Effect of Compounds on Coreceptor Binding Site Activation/Inhibition:

The binding of NBD-556 to gp120/Env causes rearrangements that expose the coreceptor site (Schon, et al., 2006, Biochemistry 45:10973-10980). Conversely, binding of the peptide 12pl causes an inaccessibility of this region (Ferrer, et al., 1999, J. Virol. 73:5795-5802; Biorn, et al., 2004, Biochemistry 43:1928-1938).

Another assay that allows the degree of "activation" (or conversely, inhibition) by a particular compound to be assessed has been developed. This assay relies on the finding that immobilized gp120 can undergo conformational rearrangements. A gp120/Env surface is exposed first to the compound of interest, then an immediate injection of the coreceptor surrogate antibody 17b or 412d. Comparison with the response of the surface to antibody alone is used as a means to determine inhibitory or enhancing effects of the compound. This assay provides an indication of whether or not the compound inhibits the gp120-CCR5 interaction. The effect of the compounds on the interaction of the sulfated N-terminal peptide of CCR5 with gp120/Env is assessed in a similar fashion (Brower, et al., 2009, Biochemistry 48:779-785). In addition, the assay can be reversed, immobilizing antibodies 17b and/or 412d on the sensor surface and passing across gp120 over these surface in the presence or absence of the test compounds as described previously (Gift, et al., 2011, Biochemistry 50:2756-2768; Gopi, et al., 2009, J. Mol. Recognit. 22:169-174; Gopi, et al., 2008, J. Med. Chem. 51: 2638-2647; Martin-Garcia, et al., 2005, J. Virol. 79:6703-6713).

Evaluating any Compound-Induced Allosteric Changes in Gp41:

As mentioned previously, interaction of CD4 with the soluble SOSIP Env trimers not only causes changes in gp120, but also changes in the accessibility of regions of gp41. Moreover, Guttman and colleagues (Guttman, et al., 2014, *Structure*, 22:974-984), demonstrated that unlike NBD-556, interaction of the Env with BMS-378806 caused perturbations in gp41 (FIG. 12). The potential of the novel compounds described herein to affect gp41 will be assessed using an SPR-based assay, immobilizing the soluble Env trimer on the surface of the sensor chip, exposing it to compounds/proteins and monitoring the interaction of gp41-directed ligands, such as T-20, and gp41 directed Abs, such as 2F5.

Effect of Compounds on Viral Fusion:

Although much is known about the gp120 structural transitions upon ligand binding, relatively little is known about the transmission of these events and the alterations to gp41 that occur. As such, the Env complex can be thought of as being analogous to a series of interacting cogs, with discrete movements and conformational events, some known and some unknown, that ultimately result in fusion and entry. Therefore, in certain embodiments the compounds of the invention disrupt hitherto unknown events in the fusion process, acting like the proverbial spanner, disallowing downstream conformational alterations in the Env complex needed to complete fusion. Therefore, the ability of compounds to disrupt the overall process of fusion using the BlaM-Vpr system is assessed (Cavrois, 2002, J. Virol. 79:6703-6713).

Develop and Evaluate Test Compound Resistant Viruses and Map Changes that Confer this Resistance.

The generation of HIV-1 variants in tissue culture systems that escape from the compounds' inhibitory effects may provide insights into the compound binding/mechanism-of-action that complement the studies described elsewhere herein. Compounds SC26, SC38, SC15, and SC45 are used in these studies. The study of the development and molecular basis of resistance to the entry inhibitors employs the well-characterized NL4-3 isolate replicating in Jurkat cells. After which, this analysis is extended to use two primary HIV-1 isolates, namely JR-FL and YU-2. Both the JR-FL and YU-2 proviruses were cloned directly from brain samples of HIV-1-infected individuals and therefore neither were ever subjected to the potential selection imposed by passage of the virus in tissue culture. JR-FL and YU-2 are both relatively resistant to neutralization by soluble CD4 and antibodies directed against the HIV-1 envelope glycoproteins (tier 2 isolates), CCR5-using (macrophage-tropic) virus. Therefore they are representative of the clinically most abundant viruses. The use of NL4-3, along with two primary R5-tropic viruses allows some assessment of the generality of results obtained. For simplicity, only the HIV-$1_{NL-43}$ experiments are presented; the experiments with JR-FL and YU-2 are performed in an identical manner but using a CCR5 expressing cell line.

A standard dose escalation method is used to select for drug-resistant HIV-1 (Waheed, et al., 2007, Proc. ACAD. Sci. USA 104: 8467-8471; Adamson, et al., 2006, J. Virol. 80:10957-10971; Waheed, et al., 2006, J. Biol. Chem. 281: 28699-28711). This method is based on the sequential passage of virus in the presence of increasing concentrations of the selecting compound in which the first passage consists of (1) the acute infection of cells with HIV-1 in the presence of test compound at twice the $IC_{50}$ of the compound; (2) collection of supernatant virus from the culture at various time points after infection; and (3) determination of the day of peak virus expression based on supernatant HIV-1 reverse transcriptase activity. The virus is serially passaged in this manner, using the virus from the day of peak virus expression to generate a new acute infection of cells and increasing the concentration of test compound approximately two-fold with each passage until drug resistance is identified or compound cytotoxicity becomes a limiting factor. Genotypic changes are monitored by sequencing the Env-coding region of the virus from each passage. Upon completion of the final passage (e.g., when sequencing results have identified a virus variant in the population with mutations that likely emerged owing to drug pressure and when this variant has become the predominant virus in the population; designated NL4-$3^R$), susceptibility testing will be performed in order to determine the resistance phenotype (i.e., fold-resistance) associated with the passaged virus.

The relevance of predicted amino acid changes in the NL4-$3^R$ Env glycoproteins to test compound resistance is determined. Each of the amplified env segments is cloned into a plasmid that efficiently expresses the HIV-1 Env glycoproteins in transfected 293T cells. The NL4-$3^R$ Env glycoproteins is tested for the ability to complement the entry of an env-defective provirus into human cells. For NL4-$3^R$ env clones encoding functional Env glycoproteins, this assay can be used to test sensitivity of the virus to test compounds. Moreover, generation of resistance to the entry inhibitor BMS-488043 correlates with increased sensitivity to neutralizing antibodies (Zhou, et al., 2010, Virology 402: 256-261). Therefore, the sensitivity of the resistant mutant Envs to a panel of neutralizing antibodies comprised of VRC01, VRC-CH31, HJ16, IgG1b12, PG9, PG16, CH01, PGT128, 2G12, 2F5 and 4E10 is assessed (deCamp, et al., 2014, J. Virol. 88:2489-2507). Sensitivity to CD4 neutralization is also assessed. These assays also provide insight into the degree of attenuation of Env glycoprotein function, if any, is associated with the development of test compound resistance.

Sequence comparison of the NL4-$3^R$ env clones that allow relative resistance to test compounds in this assay might identify predicted amino acid changes in the Env glycoproteins common to all resistance-associated clones. Examination of the location of altered amino acids in available gp120 structural models (Kwong, et al., 2000, Structure 8:1329-1339; Huang, et al., 2005, Science 310:1025-1028; Pancera, et al., 2010, Proc. Natl. Acad. Sci. USA 107:1166-1171) may provide clues regarding the likely importance of some of the changes, given understanding of the mechanism of compound inhibition derived from the described above. Through site-directed mutagenesis, these consensus changes, individually or in combination, can be introduced into the NL4-3 env gene. The changes detected in resistant virus are re-introduced (in various combinations, assuming multiple changes are observed) into the full-length clones and then tested in previously described assays (single-cycle infectivity, replication, etc.). Moreover, the resistant viruses are ran through the mechanism-of-action assays to see if whatever conformational/functional changes are imposed by the compounds in the context of the wild-type (compound-sensitive) clones are no longer observed with the resistant virus.

Structural Studies of the Entry Inhibitors in Complex with Env Constructs:

HIV-1 Env exists physiologically on the surface of the virus as trimers. Several strategies have been attempted to mimic this natural arrangement in a soluble version amenable to biophysical studies. Oligomeric gp140 polyproteins have been generated both by mutating the gp120-gp41 protease cleavage site and by expressing a wild-type polyprotein under conditions that do not foster cleavage (Earl, et al., 1994, J. Virol. 68:3015-3026; Stamatatos, et al., 2000, AIDS res. Human Retrovir. 16:981-994; Zhang, et al., 2001, J. Biol. Chem. 276:39577-39585; Srivastava, et al., 2002, J.

Virol. 76:2835-2847; Jeffs, et al., 2004, Vaccine 22:1032-1046). Trimeric forms of uncleaved gp140 have been additionally stabilized by the introduction of either heterologous trimerization domains or gp41-gp41 disulfide bonds (Yang, et al., 2000, J. Virol. 74:4746-4754; Yang, et al., 2000, J. Virol. 74:5716-5725; Pancera, et al, 2005, J. Virol. 79:9954-9969; Yang, et al., 2002, J. Virol. 76:4634-4642; Center, et al., 2004, J. Virol. 78:2265-2276). Despite some utility, none of these protein constructs adequately mimic the native Env trimer, predominantly due to the fact that they are uncleaved. This may be addressed by designing and producing recombinant, proteolytically processed SOSIP gp140 proteins that incorporate three modifications to the native Env sequence: (1) truncation at the gp41 ectodomain, (2) incorporation of a gp120-gp41 intersubunit disulfide bond, and (3) introduction of a point mutation in gp41 to enhance trimer stability (Binley, et al., 2000, J. Virol. 74:627-643; Sanders, et al., 2002, J. Virol. 76: 8875-8889). Screening of Envs from genetically distinct isolates, as well as looking at additional modifications to those Envs, for their stability/utility in the SOSIP format led to the identification of the BG505 SOSIP gp140 trimer. The development of the BG505 SOSIP trimer has allowed researchers a first glimpse of a structural picture of the organization of soluble, cleaved HIV-1 trimers (Wu, et al., 2006, J. Virol. 80:835-844). The BG505 SOSIP trimers are amenable to X-ray crystallography, cryo-EM, and negative-stain single-particle electron microscopy (Murin, et al, 2014, J. Virol. 88:10177-10188; Lyumkis, et al., 2013, *Science,* 342:1484-1490; Julien, 2013, *Science,* 342: 1477-1483). To date, the SOSIP trimers are the most physiologically relevant soluble Env constructs available.

Figure 13:
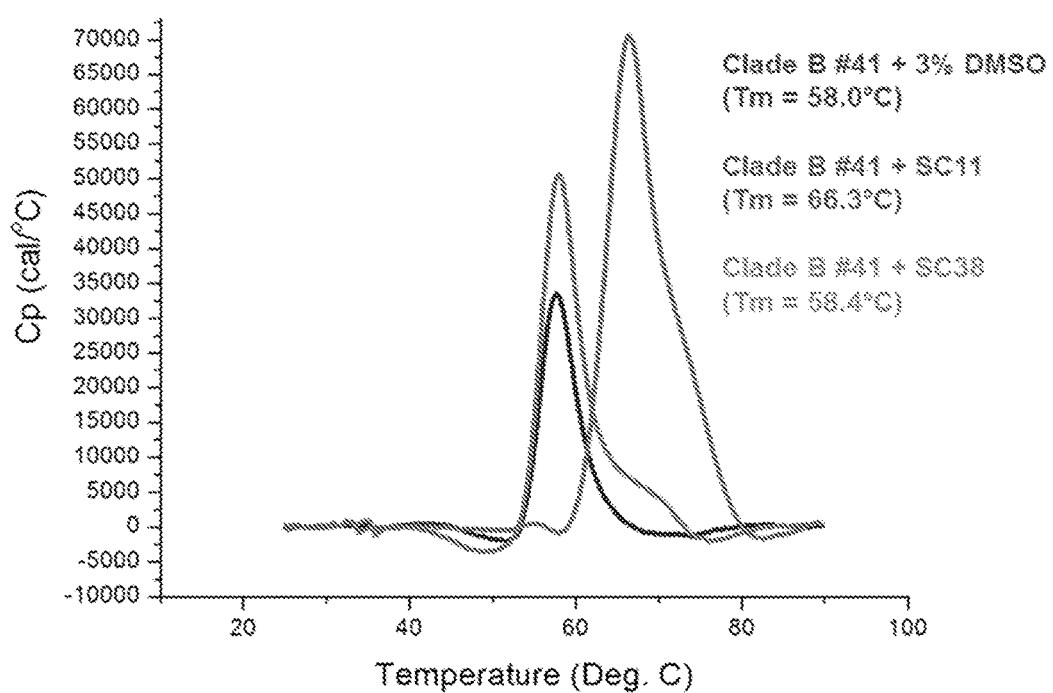
FIG. 13 is a graph illustrating Heat capacity versus temperature profiles of the Clade B #41 SOSIP trimer in the presence of compounds SC11 and SC38.

The array of purified SOSIP trimers are used to probe the conformations and the structures of soluble trimers liganded to the compounds of the invention. Compound-SOSIP trimer combinations are first screened for utility in the structural studies using a combination of SPR, ITC and DSC. The combination of methodologies defines the kinetics and affinity of a particular compound towards a given SOSIP trimer, as well as assess whether the compound imparts any increase (or decrease) in trimer stability. Compound-trimer combinations that display high affinity and structural stabilization of the trimer, are prioritized for X-ray crystallographic studies in order to obtain a high-resolution structure of the complex. FIG. 13 shows that complexing the clade B SOSIP trimer designated #41 increases the stability of the trimer construct significantly. The potential for gross conformational changes upon compound binding by the trimers is also assessed by cryo-EM and negative-stain single-particle electron microscopy. This novel methodological funnel (SPR, ITC, DSC) is believed to channel compounds into further structural studies (x-ray crystallography, cryo-EM, negative-stain single-particle electron microscopy), so that the mechanism of action and the binding site of the compounds described herein will be further explored. Moreover, in certain embodiments, the compounds of the invention allow the determination of the structure of the Env trimer at increased resolution, which significantly aids both inhibitor and vaccine design strategies.

Anti-HIV Efficacy Evaluation in Human Peripheral Blood Mononuclear Cells

HIV-1 infection of human PBMC was performed as described herein. Briefly, fresh PBMCs, seronegative for HIV and hepatitis B virus, were isolated from blood samples of the screened donors (Biological Specialty Corp., Colmar, Pa.) by using lymphocyte separation medium (density, 1.078±0.002 g/mL; Cellgro; Mediatech, Inc., Manassas, Va.) by following the manufacturer's instructions. Cells were stimulated by incubation in 4 µg/mL phytohemagglutinin (PHA; Sigma, St. Louis, Mo.) for 48 to 72 h. Mitogenic stimulation was maintained by the addition of 20 U/mL recombinant human interleukin-2 (rhIL-2; R&D Systems, Inc., Minneapolis, Minn.) to the culture medium. PHA-stimulated PBMCs from at least two donors were pooled, diluted in fresh medium, and added to 96-well plates at $5 \times 10^4$ cells/well.

Cells were infected (final multiplicity of infection of ~0.1) in the presence of nine different concentrations of compound (triplicate wells/concentration) and incubated for 7 days. To determine the level of virus inhibition, cell-free supernatant samples were collected for analysis of reverse transcriptase activity. Following removal of supernatant samples, compound cytotoxicity was measured by the addition of 3-(4,5-dimethylthiazol-2-yl)-5-(3-carboxymethoxy phenyl)-2-(4-sulfophenyl)-2H-tetrazolium (MTS; CellTiter 96 reagent; Promega) by following the manufacturer's instructions.

Bioactive Conformation Hypotheses Prediction Using FieldTemplater (Forge)

Due to the unavailability of structural information for BMS-626529 in its target-bound state, FieldTemplater (Forge) (Cresset, UK) was used to determine the most likely 3D conformation(s) adopted in binding to the target, using BMS-626529 (Nowicka-Sans et al., 2012, Antimicrob. Agents Chemother. 56:3498), BMS-488043 (Yang et al., 2010, J. Pharm. Sci. 99:2135; Wang et al., 2009, J. Med. Chem. 52:7778; Hanna et al., 2011, Antimicrob. Agents Chemother. 55:722) and BMS-378806 (Lin et al., 2003, PNAS USA100:11013; Yang et al., 2010, J. Pharm. Sci. 99:2135). Without wishing to be limited by any theory, bioactive conformations of molecules that bind to the same active site would be expected to display a similar shape, distribution of charge and hydrophobicities.

In the FieldTemplate experiment (conducted within Forge (Cresset-Ltd., New Cambridge House, Bassingboum Road, Litlington, Cambridgeshire, UK SG8 0SS)), each of the three compounds was conformationally hunted using Cresset's Xedex conformational search method (embedded within Forge). The field point pattern for each conformation of each template molecule was calculated and used to cross-compare to each other in pharmacophoric property space, without dependence on chemical structure. The calculation of field points and their use in comparing molecules was described in Cheeseright et. al., 2007, Expert Op. Drug Disc. 2:131, and the description is included in FIG. 6. These field point patterns are generated from the whole molecule, and not reliant on local or isolated features like hydrogen bonds, or aromatic moieties, thus providing a more concise, high content representation of the molecule's pharmacophoric features.

Using field point patterns, the conformations of the three BMS molecules were exhaustively compared in a pair-wise fashion until field point patterns common to all three molecules were identified. The resulting templates (i.e., binding mode hypotheses) each consist of one conformation of each of the three molecules (trios). Without wishing to be limited by any theory, the trios reported by the experiment are likely to include the correct alignment and bioactive conformation.

The trios from the FieldTemplater experiment using the BMS compounds were visually inspected and one conformation of BMS-626529 was selected as the query molecule for the Blaze (Cresset, UK) virtual screening experiment, taken from the top scoring template.

Blaze Virtual Screening Using BMS-626529 Template

The 3D field point pattern for the proposed bioactive conformation of BMS-626529 selected from the FieldTemplater experiment was used to query a database of approximately 6 million commercially available compounds (Blaze Database) using Blaze (Cresset, UK). Each of these 6 million compounds was previously conformationally populated using Cresset's conformational hunter, XedeX (http://www dot cresset-group dot com/products/xedtools/#overview) which employs Cresset's XED forcefield (Vinter et al., 1996, J. Comp-Aided Mol. Design 10:417). In addition to conformational hunting, each conformation has its three-dimensional field point pattern calculated and stored with the structure.

The Blaze virtual screening procedure is comprised of the following steps:
(1) Identification of an active ligand and its 3D bioactive conformation (single conformation). This structure is known as the search molecule.
(2) The field point pattern for this conformation of the compound of interest is produced, and it is that arrangement of field points in 3 dimensions that provides the Blaze Query.
(3) The Blaze Query is compared to the field point pattern of every conformation of all of the molecules in the Blaze Database.
(4) The results are provided and contain a similarity score (based on 50% shape/50% fields) for each molecule, a 3D alignment of the best scoring conformation, and a 2D representation.

The Blaze experiment resulted in the rank ordering of the top 1,000 commercially available compounds whose field point patterns had similarities to that of BMS-626529 in the proposed bioactive conformation. Based on visual inspection of fields and combined shape-field similarity scores (50:50), fifty compounds were chosen and purchased for biological testing using the single-round infection assay (Biorn et al., 2004, Biochemistry 43:1928).

Spark Bioisosteric Group Replacement

The use of Cresset's field point technology has been employed for field-based scaffold hopping and bioisosteric replacement since 2005 (Low et al., 2005, J. Med. Chem 48:6790; Ertl et al., 2012, J. Comp.-Aided Mol. Design 26:1207; Schuffenhauer et al., 2012, Wires Comput Mol Sci 2:842). These experiments were conducted using Spark (Cresset, UK).

To summarize the method, a section a molecule in its bioactive conformation (not necessary, but 3D binding structure is desirable) is selected and designated for replacement. When that moiety is clipped away, replacement candidates from Spark's fragment databases are fit into the molecule and scored (more details are provided below).

Spark's fragment databases are provided with the software and consist of fragments generated from commercially available screening compounds, ChEMBL (Gaulton et al., 2012, Nucl. Acids Res. 40:D1100), and VeHICLE (Pitt et al., 2009, J. Med. Chem. 52:2952) databases.

Fragments are generated by the method outlined in the Spark user manual (Cresset-Ltd., New Cambridge House, Bassingboum Road, Litlington, Cambridgeshire, UK SG8 0SS), which entails breaking all "breakable" bonds in a molecule, then reconnecting sets of pieces to form bigger fragments. Fragments, by default, may contain up to 15 heavy atoms and 5 rotatable bonds, with a molecular weight maximum of 250. Each fragment has up to 30 conformations generated and stored, with field point patterns calculated for each conformation. Along with field point patterns, the relative orientations and positions of fragment attachment points.

In the course of the Spark experiment, a portion of the molecule to be replaced is selected; the number of bonds that were broken along with the distances and angles between broken bonds are recorded. The first pass through the Spark fragment databases involves finding fragments which have the same number of attachment points, and approximately the same geometry ('bite size' and 'bite angle'). Each one of these first-pass fragments are fit into the original molecule; fields and field points are calculated for the resulting molecules. The resulting molecules are minimized using the XED forcefield, then the full field and shape of the result molecule is scored against the full field and shape of starting molecule (or other designated reference molecule, or combination thereof). By default, 50% shape and 50% fields.

Example 1: Synthesis of SC04

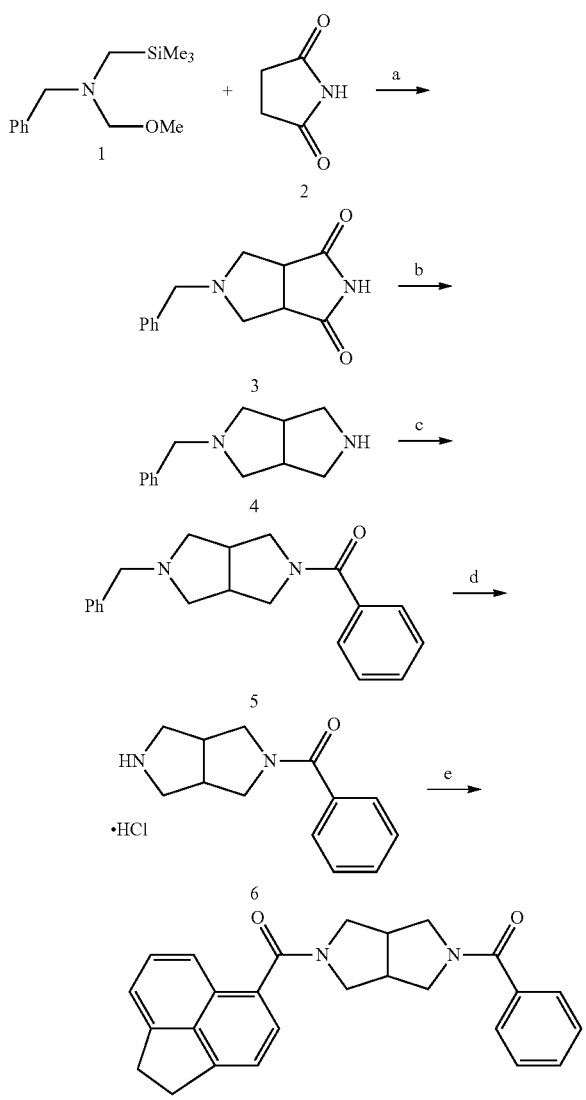

SC04
<sup>a</sup>Reagent and conditions: (a) TFA, CH$_2$Cl$_2$, (b) LAH, THF. (c) PhCOCl, Et$_3$N, CH$_2$Cl$_2$, (d) H2, Pd/C, MeOH. (e) Acenaphlene-5-carboxylic acid, EDC, Et$_3$N, CH$_2$Cl$_2$.

Trifluoroacetic acid (TFA, 1.48 g, 0.013 mol) was added to a cold (0° C.) solution of compound 2 12.6 g, 0.13 mol)

in dichloromethane (250 mL) under nitrogen. A solution of compound 1 (31 g, 0.13 mol) in dichloromethane (200 mL) was added drop-wise over 45 min. After the addition was complete, the mixture was warmed slowly to ambient temperature and stirred for 16 h. The mixture was concentrated and the resulting residue was dissolved in dichloromethane (200 mL) and washed with saturated aqueous sodium bicarbonate (2×100 mL). The aqueous layer was separated and extracted with dichloromethane (2×150 mL). The combined dichloromethane extracts were washed with brine (150 mL), dried over anhydrous magnesium sulphate, filtered and concentrated to give 30 g (75% yield) of compound 3 as a light yellow solid.

The crude compound 3 (30 g, 0.13 mol) was dissolved in dry tetrahydrofuran (THF) (500 mL) under nitrogen atmosphere, and then lithium aluminium hydride (14.8 g, 0.39 mol) was slowly added at 0° C. over 30 min. The resulting mixture was stirred at ambient temperature for 30 min and then warmed to reflux for 7 h. The mixture was then cooled to 0° C. and quenched by the slow addition of an excess of H$_2$O/THF solution (1/10). The mixture was warmed to ambient temperature and stirred for 1 h. The solids were filtered and the residue was washed with ethyl acetate (3×150 mL). The combined filtrates were concentrated to give 27 g of a crude material. Purification of the crude compound 4 was successfully performed by column chromatography with EtOAc/hexene (3/1+10% TEA) as an eluent. 19.2 g (73 percent yield) of the pure material were obtained.

A solution of benzoyl chloride (6.6 g, 0.047 mol) in DCM (100 mL) was being added dropwise to a stirred mixture of compound 4 (9.5 g, 0.047 mol) and Et$_3$N (20 g, 0.15 mol) in DCM (150 mL) at room temperature during 30 min. After the addition was complete, the reaction mixture was stirred at room temperature for 5 h and then washed with water (2×100 mL), 1 N aq. HCl (2×50 mL), water (2×50 mL), saturated aq. NaHCO$_3$ (2×75 mL), and brine (2×50 mL). After drying over MgSO$_4$, the solvent was evaporated under reduced pressure to give the compound 5 (13.3 g, 0.043 mol, 93 percent yield) as a yellow oil.

Compound 5 (10.3 g, 0.033 mol) was added to the suspension of 10% Pd/C (1.5 g) in anhydrous methanol (250 mL). This mixture was hydrogenated at 20 atm and RT for 10 h. The catalyst was filtered off through a pad of Celite, which was then washed with anhydrous methanol (200 mL). The solvent was evaporated under reduced pressure to afford the crude product 6 as yellow oil. Obtained material were dissolved in 0.5 N aq. HCl (50 mL), treated with charcoal, and filtered. The filtrate was evaporated to dryness to give 7 g (0.027 mol, 83 percent yield) of compound 6*HCl as a white solid.

Acenaphthene-5-carboxylic acid (0.3 g, 1.5 mmol) was added to a mixture of compound 6*HCl (0.38 g, 1.5 mmol) and TEA (0.41 g, 4 mmol) in CH$_2$Cl$_2$ (25 mL) at the room temperature. Then 1-Ethyl-3-(3-dimethylaminopropyl)carbodiimide (0.3 g, 1.6 mmol) was added and the mixture was stirred at the room temperature for 16 h. The organic phase was then washed with water (2×200 mL), 1 N aq. HCl (2×150 mL), water (2×200 mL), saturated aq. NaHCO$_3$ (2×200 mL), and brine (2×150 mL). After drying over MgSO$_4$, the solvent was evaporated under reduced pressure to give the crude compound 7 (0.52 g) in a form of a yellow oil. The crude material was purified three times by column chromatography with DCM/MeOH (10/2) as an eluent. Final purification was performed by preparative HPLC to provide 40 mg (0.6 mmol, 8 percent yield) of the pure compound 7 as a light yellow solid.

Example 2: Synthesis of SC07

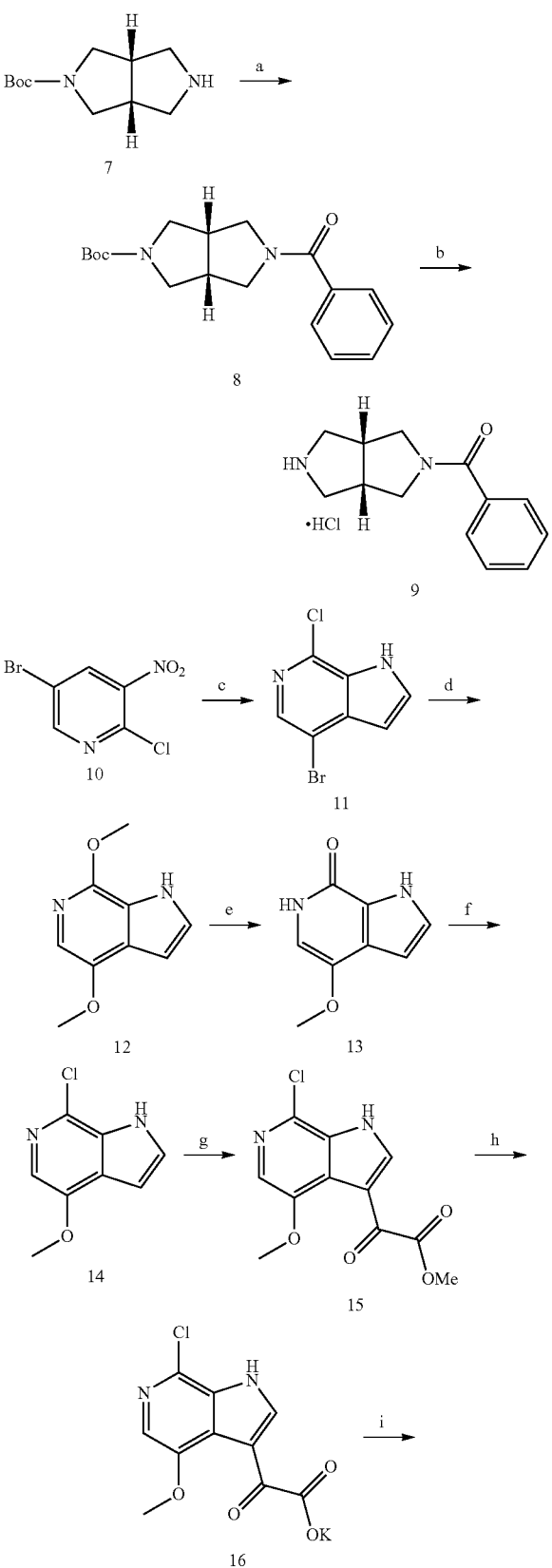

-continued

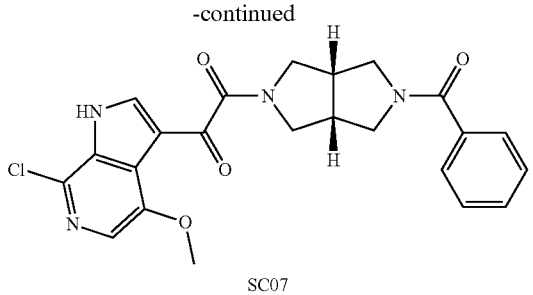

SC07

*Reagent and conditions: (a) PhCOCl, Et₃N, CH₂Cl₂, 0° C. to rt. (b) HCl (4N), Et₂O. (c) vinylmagnesium bromide THF. -78° C. (d) 1) MeOK, toluene, reflux; 2) Cu (cat.), toluene, reflux, (e) HCl, NMP—H₂O, 100° C. (f) POCl₃, 100° C. (g) ClCOCO₂Me, AlCl₃, CH₂Cl₂, 0° C. to rt. (h) K₂CO₃, MeOH. (i) 9, EDCl, DIEA, DMF.

To a solution of compound 7 (212.3 mg; 1 mmol) in DCM (30 ml) was added TEA (325 mg; 3.2 mmol). The resulted solution was cooled to 0° C. and a solution of benzyl chloride (140 mg; 1 mmol) in DCM (5 ml) was added dropwise. The reaction mixture was stirred at room temperature for 2 hr, and then water (100 ml) with NaHCO₃ sat. (10 ml) were added. Organic layer was separated, washed with water and dried over Na₂SO₄. DCM was evaporated to afford compound 8 (160 mg; 50%) as yellow oil. To a solution of compound 8 (1.1 g; 3.5 mmol) in dry Et₂O (5 ml) under argon was added 4N HCl in Et₂O (5 ml). The mixture was stirred for 3 h and the formed precipitate was filtered, washed with Et₂O and stored into a desiccator to give compound 9 (0.67 g, 89%) as a white powder.

To a solution of compound 10 (250 mg; 1.05 mmol) in dry THF (10 ml) under argon at −78° C. was added dropwise a 1.42 M solution of vinylmagnesium bromide in THF (6 ml, 8.4 mmol; prepared by dilution of 1.7 M solution of in THF (50 ml) with THF (12 ml)). The reaction mixture was stirred at the same temperature for another 1.5 h and then it was quenched by addition of NH₄Cl sat. (30 ml). The THF-layer was separated and the aqueous layer was extracted with EtOAc (2×10 ml). Combined organic layers (THF with EtOAc extracts) were dried over Na₂SO₄ and concentrated to afford 270 mg of yellow oily material which was treated with DCM (10 ml). Light-yellow solid was filtered and dried in oven (45° C.) to give compound 11 (70 mg, 29%).

To a solution of compound 11 (3.8 g; 16.4 mmol), celite (6.16 g) in dry toluene (60 ml) was added a solution of potassium (6.39 g; 164 mmol) in MeOH (50 ml). The reaction mixture was heated at reflux (with Dean-Stark trap) for 12 h, then it was cooled to ambient temperature and mixture of toluene and methanol (1/1, 50 ml) was added. Then the reaction mixture was heated again and when the temperature was 60° C., CuI (3.43 g; 18 mmol) was added. The mixture was held at 115° C. for 1.5 h while collecting a mixture of MeOH and toluene. The mixture was cooled to ambient temperature and water (60 ml) was added. A precipitate formed was filtered off and washed with EtOAc (100 ml), then aqueous layer was extracted with EtOAc (50 ml). Combined EtOAc-layers were dried over Na₂SO₄ and concentrated to afford compound 12 (2.4 g, 82%) as light-yellow solid. To a solution of compound 12 (0.8 g; 4.5 mmol) in N-methylpyrrolidone (5 ml), water (0.5 ml) and hydrochloric acid (5-6 drops) were added. The mixture was stirred at 100° C. for 6 h. The mixture was cooled to room temperature and water (100 ml) was added. Then NaHCO₃ sat. (20 ml) was added, the product was extracted with EtOAc (5×20 ml). Combined extracts were dried over Na₂SO₄ and concentrated to afford compound 13 (0.6 g, 81%) as pink solid. A solution of compound 13 (1.8 g; 11 mmol) in POCl₃ (20 ml) was stirred at 100° C. for 12 h. Then POCl₃ was evaporated under reduced pressure. To a residue ice water (100 ml) and then NaHCO₃ sat. (25 ml) were added, the product was extracted with EtOAc (3×35 ml). Combined extracts were dried over Na₂SO₄ and concentrated to afford compound 14 (0.8 g, 40%) as light-yellow solid. To a 0° C. suspension of ethyl 2-chloro-2-oxoacetate (222.7 mg; 1.63 mmol) and AlCl₃ (237 mg; 1.78 mmol) in DCM (5 ml) was added dropwise a suspension of compound 14 (165 mg; 0.92 mmol) and AlCl₃ (122 mg; 0.92 mmol) in DCM (5 ml). The reaction mixture was stirred at room temperature for 2 h. Then the mixture was cooled again and water (50 ml) with NaHCO₃ sat. (10 ml) were added maintaining the temperature 0° C. Organic layer was separated, dried over Na₂SO₄ and concentrated. Crude product was purified by column chromatography (EtOAc/hexane 1:1) to afford compound 15 (50 mg, 20%) as yellow crystals. Compound 15 (350 mg; 1.24 mmol) was dissolved in aqueous methanol (1/1, 14 ml) and K₂CO₃ (0.34 g; 2.48 mmol) was added to the solution. The mixture was stirred at room temperature for 8 h. The solvent was removed under vacuo to afford crude compound 16 (361 mg) as white powder which used for the next step without further purification. A solution of compound 16 (361 mg; 1.23 mmol), EDCI (353 mg; 1.85 mmol) and DIPEA (635 mg; 4.92 mmol) in dry DMF (10 ml) was stirred for 1 h. Then compound 9 (311 mg; 1.23 mmol) was added and the reaction mixture was stirred at 20° C. for another 18 h. Then water (100 ml) with NaHCO₃ sat. (10 ml) were added. Target compound was extracted with DCM (3×30 ml). Combined extracts were dried over Na₂SO₄ and concentrated. Crude material was purified by column chromatography (EtOAc/MeOH 9:1) to afford SC07 (28 mg, 4.6%) as a yellow powder.

Example 3: Synthesis of SC08

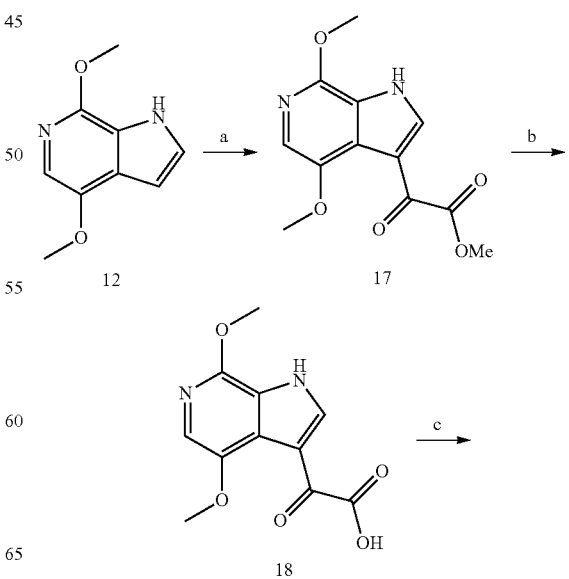

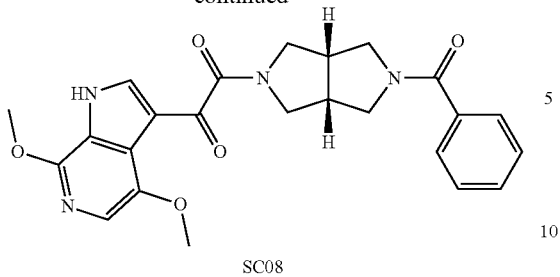

SC08

*Reagent and conditions:
(a) ClCOCO₂Me, AlCl₃, CH₂Cl₂, 0° C. to rt.
(b) K₂CO₃, MeOH.
(c) 9, EDCl, DiEA, DMF.

A solution of compound 12 (300 mg; 1.69 mmol) and AlCl₃ (230 mg; 1.75 mmol) in DCM (10 ml) was added dropwise to a 0° C. suspension of ethyl 2-chloro-2-oxoacetate (600 mg; 4.3 mmol) and AlCl₃ (600 mg; 4.6 mmol) in DCM (10 ml). The reaction mixture was stirred at room temperature for 18 h. Then the mixture was cooled again and water (50 ml) with NaHCO₃ sat. (25 ml) were added maintaining the temperature 0° C. Organic layer was separated, dried over Na₂SO₄ and concentrated. Crude product was purified by column chromatography (EtOAc/hexane 1:2) to afford compound 17 (144 mg, 30%) as a yellow powder. K₂CO₃ (0.839 g; 6.08 mmol) was added to a solution of compound 17 (845 mg; 3.04 mmol) in aqueous methanol (1/1; 14 ml). The mixture was stirred at room temperature for 8 h. A precipitate obtained was filtered and washed with MeOH to give compound 18 (500 mg, 57%) as a white powder. A solution of compound 18 (288 mg; 1 mmol), EDCI (287 mg; 1.5 mmol) and DIPEA (516 mg; 4 mmol) in dry DMF (10 ml) was stirred for 1 h. Then compound 9 (252 mg; 1 mmol) was added and the reaction mixture was stirred at 20° C. for another 18 h. Then water (100 ml) with NaHCO₃ sat. (10 ml) were added. Target compound was extracted with DCM (3×30 ml). Combined extracts were dried over Na₂SO₄ and concentrated. Crude material was purified by column chromatography (EtOAc/MeOH 9:1) to afford SC08 (190 mg, 42%) as a pale green solid.

Example 4: Synthesis of SC11

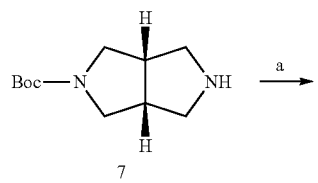

7

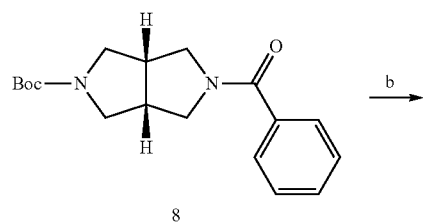

8

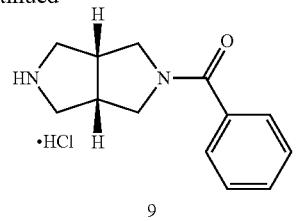

9

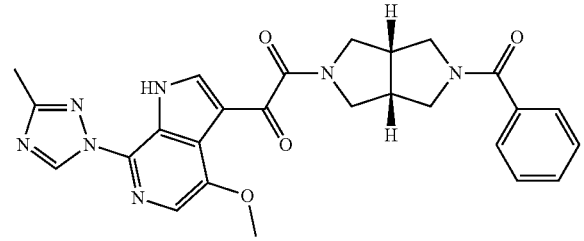

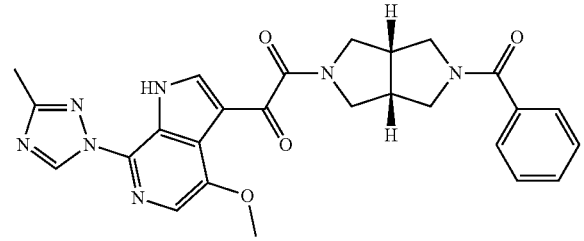

SC11

*Reagent and conditions: (a) PhCO₂H, HBTU, Et₃N, CH₂Cl₂, rt. (b) HCl (4N), dioxane,
(c) 1) HCl (4N), dioxane; 2) NMP—H₂O, 90° C. (d) POCl₃, 95° C.
(d) 3-methyl-1H-1,2,4-triazole, 143° C. (e) ClCOCO₂Me, AlCl₃, CH₂Cl₂, rt.
(g) NaOH, MeOH—H₂O. (h) 9, DEPBT, DIEA, DMF.

To a stirred solution of benzoic acid (116 mg, 0.94 mmol) in DCM (3 mL) were added compound 7 (200 mg, 0.94 mmol), TEA (0.4 mL, 2.82 mmol) and HBTU (536 mg, 1.39 mmol). The resulting mixture was stirred at r.t. overnight before quenched with sat. NaHCO₃. The layers were separated and the aqueous layer was extracted with DCM (10 mL×3). The combined organic layers was dried over Na₂SO₄, filtered and concentrated. The residue was purified by flash chromatography (silica gel, 0~50% ethyl acetate in petroleum ether with 0.5% TEA) to provide compound 8 (164 mg, 55%) as a yellow solid. Compound 9 (303 mg, 100%) was obtained as a yellow oil by treating compound 8 (345 mg, 1.09 mmol) with 4N HCl/Dioxane (3 mL).

To a solution of compound 12 (0.8 g; 4.5 mmol) in N-methylpyrrolidone (5 ml), water (0.5 ml) and hydrochloric acid (5-6 drops) were added. The mixture was stirred at 100° C. for 6 h. The mixture was cooled to room temperature and water (100 ml) was added. Then NaHCO₃ sat. (20 ml) was added, the product was extracted with EtOAc (5×20 ml). Combined extracts were dried over Na₂SO₄ and concentrated to afford compound 13 (0.6 g, 81%) as pink solid. A solution of compound 13 (1.8 g; 11 mmol) in POCl₃ (20 ml) was stirred at 100° C. for 12 h. Then POCl₃ was evaporated under reduced pressure. To a residue ice water (100 ml) and then NaHCO₃ sat. (25 ml) were added, the product was extracted with EtOAc (3×35 ml). Combined extracts were dried over Na₂SO₄ and concentrated to afford compound 14 (0.8 g, 40%) as light-yellow solid At 143° C., to molten 3-methyl-1H-1,2,4-triazole (744 mg, 8.95 mmol) under N₂ atmosphere, was added compound 14 (392 mg, 1.79 mmol). After stirring for 20 hrs, the reaction mixture was cooled down to r.t. and partitioned between H₂O (20 mL) and EA (20 mL). The layers were separated and the aqueous layer was extracted with EA (20 mL×3). The combined organic layers was dried over Na₂SO₄, filtered and concentrated. The residue was purified by prep. HPLC (C18, 10% to 89% acetonitrile in water (0.1% formic acid)) to compound 19 (182 mg, 44%) as a white solid. To a stirred solution of AlCl₃ (1.588 g, 11.9 mmol) in DCM (10 mL) was added methyl 2-chloro-2-oxoacetate (389 mg, 3.18 mmol) and the resulting mixture was stirred at r.t. until it became a clear solution before introduction of compound 19 (182 mg, 0.79 mmol, in 1 mL DCM). The stirring was continued at r.t. overnight. After completion of the reaction, the mixture was quenched with sat. NaHCO₃ and extracted with DCM (10 mL×3). The combined organic layers were washed with brine, dried over Na₂SO₄ and concentrated. The residue was purified by flash chromatography (silica gel, 0~90% ethyl acetate in petroleum ether) to provide compound 20 (58 mg, 23%) as a yellow oil. To a stirred solution of compound 20 (58 mg, 0.18 mmol) in MeOH/H₂O (1 mL/2 mL) was added NaOH (15 mg, 0.37 mmol). After stirring at r.t. for 15 min, the reaction mixture was neutralized with 1N HCl, concentrated and lyophilized to provide compound 21 (73 mg, 95%, mixed with NaCl) as a green solid.

Compound 21 (55 mg, 0.18 mmol) in DMF and compound 9 (59 mg, 0.27 mmol) were added to DIPEA (0.28 mL, 1.63 mmol) and DEPBT (325 mg, 1.09 mmol). After stirring at r.t. overnight, the reaction mixture was concentrated to remove DMF under the reduced pressure. The residue was partitioned between with EA (10 mL) and sat. NaHCO₃(10 mL). The layers were separated and the aqueous layer was extracted with EA (10 mL×2). The combined organic layers was dried over Na₂SO₄, filtered and concentrated. The crude product was purified by preparative HPLC to give compound SC11 (22 mg, 24%).

Example 5: Synthesis of SC26

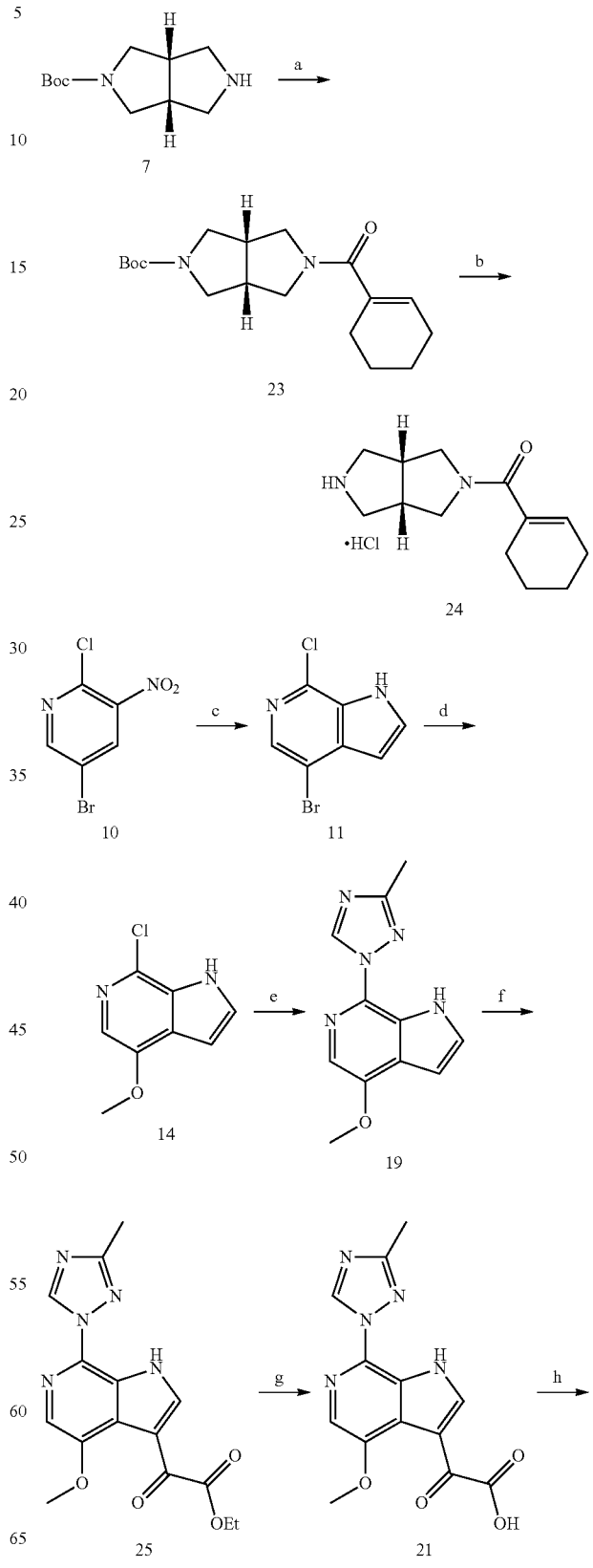

-continued

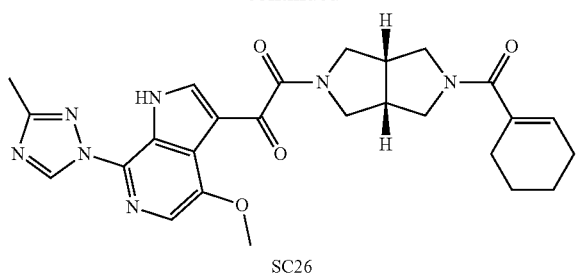

SC26

<sup>a</sup>Reagent and conditions:
(a) cyclohexene-1-carboxylic acid, HATU, DIEA, DMF, rt.
(b) HCl, EtOAc,
(c) vinylmagnesium bromide THF, -78° C. to -40° C.,
(d) NaOMe, CuI, MeOH, microwave, 110° C.,
(e) 3- methyl-1H-1,2,4-triazole, copper powder, KOHm, 107-175° C.,
(f) ClCOCO$_2$Et, EtMgBr, py, THF, -45°C. -10° C.,
(g) NaOH, MeOH—H$_2$O.
(h) 24, HATU, DIEA, DMF.

To a solution of cyclohexene-1-carboxylic acid (0.15 g, 1.19 mmol) in DMF (5 mL) was added compound 7 (0.21 g, 0.99 mmol), HATU (0.45 g, 1.19 mmol, 1.2 eq.) and DIEA (0.26 g, 1.98 mmol). Then the mixture was stirred at 25° C. for 16 hrs. The crude product was purified by pre-HPLC to give tert-butyl compound 23 (0.21 g, 0.67 mmol, 67%). HCl/AcOEt (20 mL) was added compound 23 (0.21 g, 0.67 mmol), the mixture was stirred at 25° C. for 2 hrs, TLC showed the S.M was consumed completely. The mixture was concentrated to give compound 24 (0.15 g, 0.58 mmol) as crude product.

To a solution of compound 21 (0.03 g, 0.99 mmol) in DMF (2 mL) was added compound 24 (0.026 g, 0.12 mmol), HATU (0.045 g, 0.12 mmol) and DIEA (0.026 g, 0.2 mmol). Then the mixture was stirred at 25° C. for 16 hrs. The crude product was purified by pre-HPLC to give SC26 (15 mg, 30%).

Example 6: Synthesis of SC14

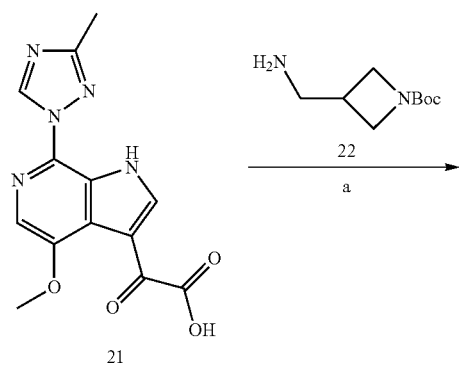

-continued

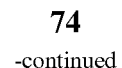

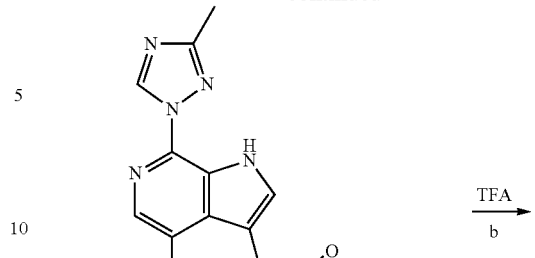

23

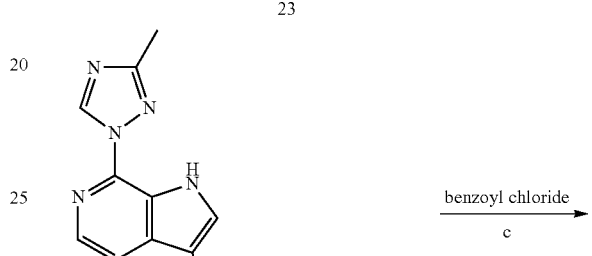

24

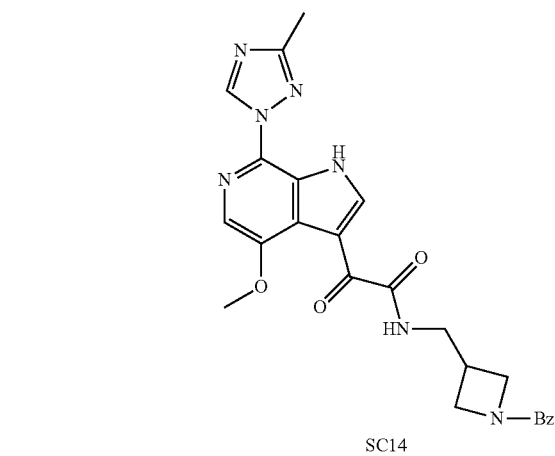

SC14

(a) HATU, DIEA, DMF; (b) TFA, DCM; (c) DIEA, DCM

The solution of compound 21 (0.1 g, 0.33 mmol) in DMF (3 mL) was added DIEA (0.086 g, 0.66 mmol), compound 22 (0.074 g, 0.4 mmol) and HATU (0.15 g, 0.4 mmol). The mixture was stirred at 25° C. for 2 hrs and purified by pre-HPLC to give compound 23 (0.089 g, 57%). TFA (1 mL) in DCM (10 mL) was added to compound 23 (0.089 g, 0.19 mmol). The mixture was stirred at 25° C. for 3 hrs and the mixture was concentrated to give compound 24 (0.13 g, crude). To the solution of compound 24 (0.13 g, 0.35 mmol) in DCM (2 mL) was added DIEA (0.09 g, 0.66 mmol), and benzoyl chloride (0.049 g, 0.35 mmol) was added dropwise to the above solution at 0° C. The mixture was stirred at 25° C. for 2 hrs and purified by pre-HPLC to give compound SC14 (0.031 g, 19%).

Example 7: Synthesis of SC15

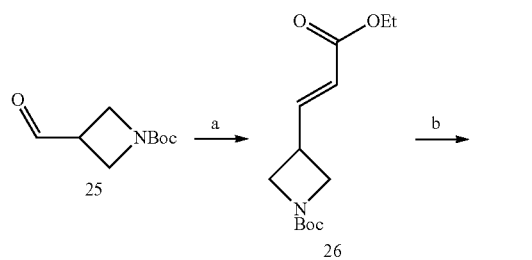

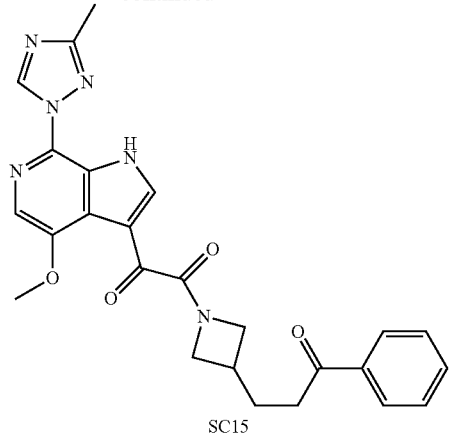

SC15

(a) ethyl-2-(diethoxyphosphoryl) acetate, NaH, THF, 0° C.; (b) H₂, Pd/C, EtOac; (c) LiOH, MeOH, H₂O; (d), N,O-dimethylhydroxylamine hydrochloride, HATU, DIEA, DMF; (e) phenyl magnesium bromide, THF, 0° C.; (f) TFA, DCM; (g) HATU, DIEA, DMF

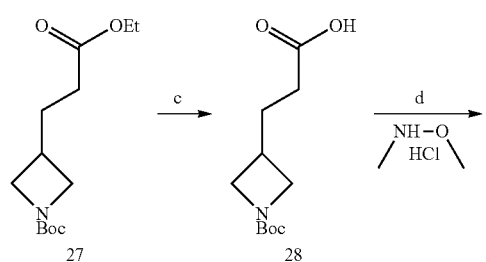

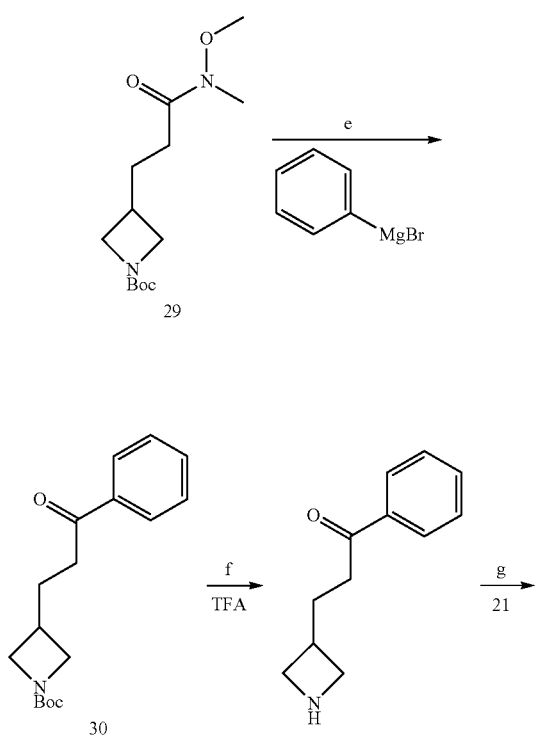

To a solution of ethyl-2-(diethoxyphosphoryl) acetate (1.45 g, 6.5 mmol) in THF (30 mL) was added NaH (0.26 g, 10.8 mmol) at 0° C. The suspension was stirred at 0° C. for 5 min. Then compound 25 (1 g, 5.4 mmol) was added to the above mixture, the mixture was stirred at 0° C. for 10 min, TLC showed the starting material was consumed completely. The mixture was quenched with saturated aqueous NH₄Cl solution and extracted with EtOAc (3×30 mL) and the combined organic layer washed with brine and concentrated. The crude product was purified by silica gel column chromatography to obtain compound 26 (0.6 g, 43%). A mixture of compound 26 (0.6 g, 2.3 mmol), Pd/C (0.05 g) in EtOAc (50 mL) was degassed and flushed with H₂ for three times, then the system was kept at a H₂ pressure of 20 Psi, and stirred at 25° C. for 5 hrs.

The reaction mixture was filtered, and the filtrate was evaporated to give compound 27 (0.56 g, 95%). To a solution of compound 27 (0.56 g, 2.18 mmol) in MeOH (15 mL) was added LiOH (0.16 g, 4.36 mmol) and H₂O (2 mL). The mixture was stirred at 25° C. for 6 hrs, and then saturated citric acid was added to pH=6. The mixture was extracted with EtOAc (3×30 mL) and the combined organic layer was washed with brine and concentrated. The crude product was purified by silica gel column chromatography to obtain compound 28 (0.48 g, 96%). To the solution of compound 28 (0.48 g, 2.06 mmol) in DMF (5 mL) was added DIEA (0.53 g, 4.12 mmol), N,O-dimethylhydroxylamine hydrochloride (0.24 g, 2.47 mmol) and HATU (0.94 g, 2.47 mmol). The mixture was stirred at 25° C. for 2 hrs and purified by pre-HPLC to give compound 29 (0.52 g, 93%).

A solution of compound 29 (0.52 g, 1.91 mmol) in THF (20 mL) was cooled to 0° C., phenylmagnesium bromide (0.69 g, 3.82 mmol) was added dropwise to the above mixture below 0° C., after addition, the mixture was stirred at 0° C. for 2 hrs. The mixture was quenched with saturated aqueous NH₄Cl solution and extracted with EtOAc (3×30 mL) and the combined organic layer washed with brine and concentrated. The crude product was purified by silica gel column chromatography to obtain compound 30 (0.52 g, 94%).

TFA (2 mL) in DCM (20 mL) was added to compound 30 (0.52 g, 1.79 mmol). The mixture was stirred at 25° C. for 3 hrs and the mixture was concentrated to give compound 31

(0.7 g, crude). To the solution of compound 31 (0.068 g, 0.36 mmol) in DMF (3 mL) was added DIEA (0.074 g, 0.6 mmol), compound 21 (0.09 g, 0.3 mmol) and HATU (0.14 g, 0.36 mmol). The mixture was stirred at 25° C. for 2 hrs and purified by pre-HPLC to give compound SC15 (0.034 g, 24%).

Example 8: Synthesis of SC16

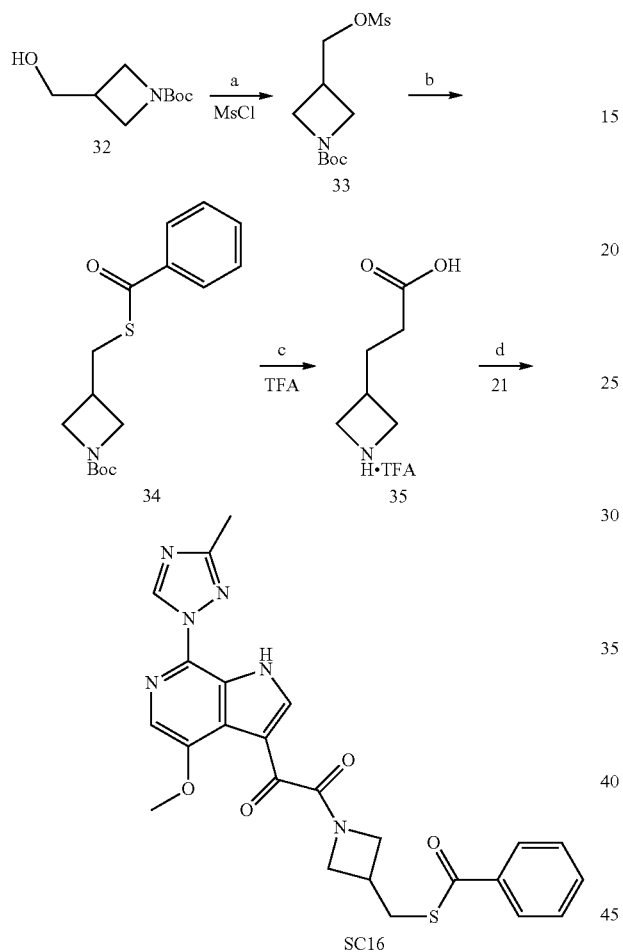

SC16
(a) MsCl, NMM, DCM, 0-25° C.; (b) benzothioic S-acid, DMF, 80° C.; (c) TFA, DCM; (d) HATU, DIEA, DMF To a solution of compound 32 (2 g, 10 mmol) in DCM (30 mL) was added NMM (2 g, 20 mmol). The mixture was cooled to 0° C., MsCl (1.37 g, 12 mmol) was added dropwise, after addition, the mixture was stirred at 25° C. for 16 hrs. To the solvent was added $H_2O$ and the system was extracted with DCM. The DCM phase was evaporated and the residue was purified by silica gel column chromatography to obtain compound 33 (1.8 g, 68%).

To a solution of compound 33 (1.8 g, 6.79 mmol) in DMF (10 mL) was added $K_2CO_3$ (1.87 g, 14 mmol) and benzothioic S-acid (1.12 g, 8.15 mmol). The mixture was heated to 80° C. for 2 hrs. To the mixture was added water, and the system was extracted with EtOAc. The EtOAc phase was washed with $H_2O$ and brine, concentrated to give crude product which was purified by silica gel column chromatography to obtain compound 34 (2 g, 96%).

TFA (3 mL) in DCM (20 mL) was added to compound 34 (2 g, 6.5 mmol). The mixture was stirred at 25° C. for 3 hrs and the mixture was concentrated to give compound 35 (2.3 g, crude). To the solution of compound 35 (0.83 g, 0.4 mmol) in DMF (3 mL) was added DIEA (0.085 g, 0.66 mmol), compound 21 (0.1 g, 0.33 mmol) and HATU (0.15 g, 0.4 mmol). The mixture was stirred at 25° C. for 2 hrs and purified by pre-HPLC to give compound SC16 (0.032 g, 20%).

Example 9: Synthesis of SC18

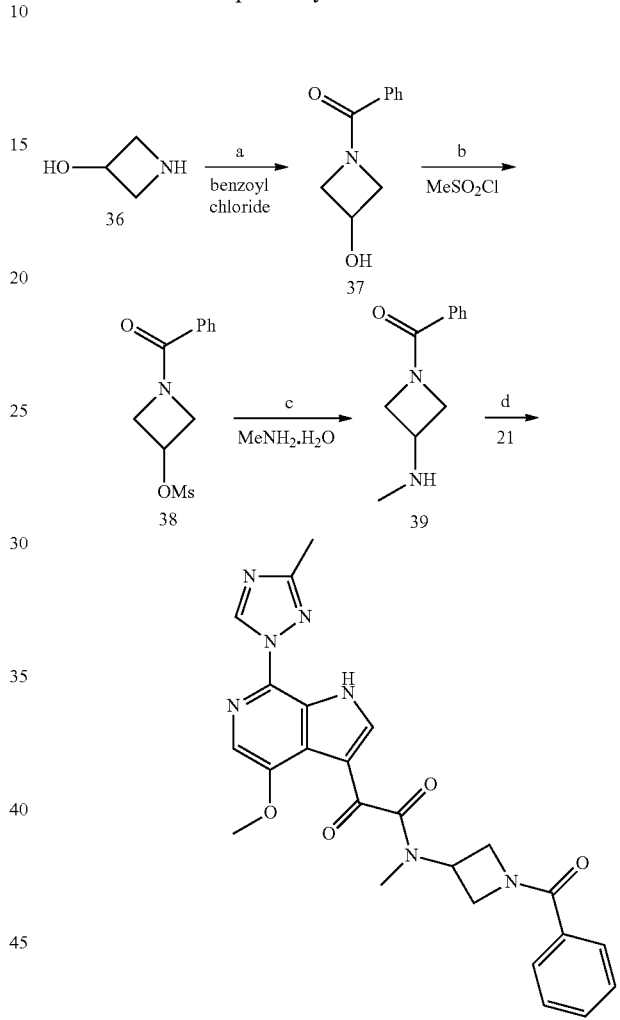

SC18
(a) $K_2CO_3$, THF—$H_2O$; (b) $Et_3N$, THF; (c) IPA, 130° C.; (d) HATU, DIEA, DMF

Compound 36 (2 g, 18 mmol) was dissolved in 30 mL of THF-water (2:1) and cooled to 0° C. $K_2CO_3$ (6.06 g, 43 mmol) was added, followed by a solution of benzoyl chloride (2.823 g, 19.8 mmol) in 5 mL of dry THF, added dropwise. The reaction mixture was stirred at room temperature for 2 hours and poured into 100 mL of a 5% solution of $NaHCO_3$. The mixture was extracted with DCM (2×30 mL) and the organic layer was dried with $Na_2SO_4$ and concentrated to obtain compound 37 (1.2 g, 40%) as colorless crystals.

A solution of compound 37 (1 g, 5.4 mmol) was dissolved in 10 mL of THF and triethylamine (0.877 mL, 8.5 mmol) was added. The mixture was cooled to 0° C. and mesyl chloride (0.909 g, 7.7 mmol) was added dropwise. The reaction mixture was stirred for 1 hour at room temperature and poured into 100 ml of water. The mixture was extracted with DCM (3×30 mL), the combined organic layers were washed with 20 mL of brain, dried over $Na_2SO_4$ and concentrated to obtain compound 38 (1.2 g, 80%) as white crystals.

To a solution of compound 38 (1.2 g, 4.8 mmol) in 10 mL of IPA was added methylamine (7.5 g of 40% aqueous solution) and the mixture was stirred and heated in a sealed tube for 48 hours at 130° C. The reaction mixture was poured into 100 mL water and extracted with DCM (5×20 mL). The combined extracts were dried over $Na_2SO_4$ and concentrated. Crude material was purified by column chromatography (DCM:MeOH 98:2, then 97:3 as eluent) to obtain compound 39 (370 mg, 40%) as colorless oil.

A solution of compound 21 (69 mg, 0.23 mmol), HATU (261 mg, 0.68 mmol) and DIEA (118 mg, 0.91 mmol) in dry DMF (10 ml) was stirred for 1 h. Then compound 26 (87 mg, 0.45 mmol) was added. The reaction mixture was stirred at 20° C. for 18 h. Then water (100 ml) with $NaHCO_3$ sat. (10 ml) were added, and the organic layer was extracted with EtOAc (3×30 ml). Combined extracts were dried over $Na_2SO_4$ and concentrated. Crude material was purified by column chromatography (DCM:MeOH 98:2 as eluent) to give compound SC18 (27 mg, 25%) as a pale yellow solid.

Example 10

As a first step in the present investigation, field-based 3D similarity experiments using Blaze (Cresset, UK) and a high-content field-based pharmacophore template derived from BMS-626529 were employed to find novel scaffolds that function as entry inhibitors. To perform a Blaze virtual screening protocol, an active ligand in either its 3D bioactive conformation bound to its target should be identified; in the absence of crystal structure, it may be calculated by pharmacophore modeling.

Figure 6A:
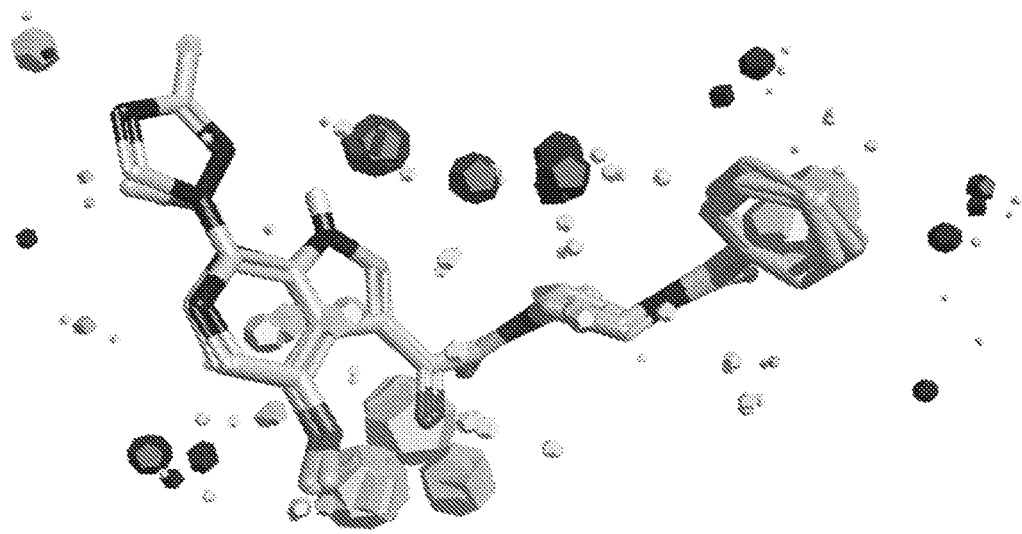
FIGS. 6A-6B, illustrates aspects of molecular modeling.
Figure 6B:
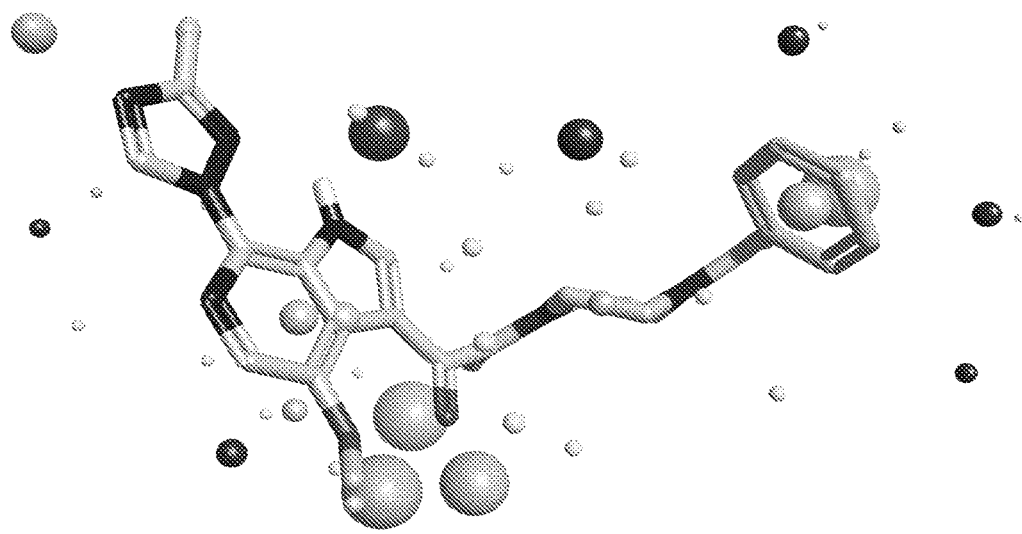

As no structural information is currently available for BMS-626529 in its target-bound state, FieldTemplater (Forge) (Cresset, UK) was used to determine a hypothesis for the 3D conformation adopted in binding to the target, templating with compounds BMS-488043 and BMS-378806. This FieldTemplater derived hypothesis for the bioactive conformation was then annotated with its calculated field points, resulting in a 3D field point pattern. The field point pattern provides a condensed representation of the compound's shape, electrostatics, and hydrophobicity; should two diverse structures have conformations with similar field point patterns, they are experienced by the receptor in a similar fashion. The field point alignment for the three selected templating molecules is shown in FIG. 6.

Figure 7:
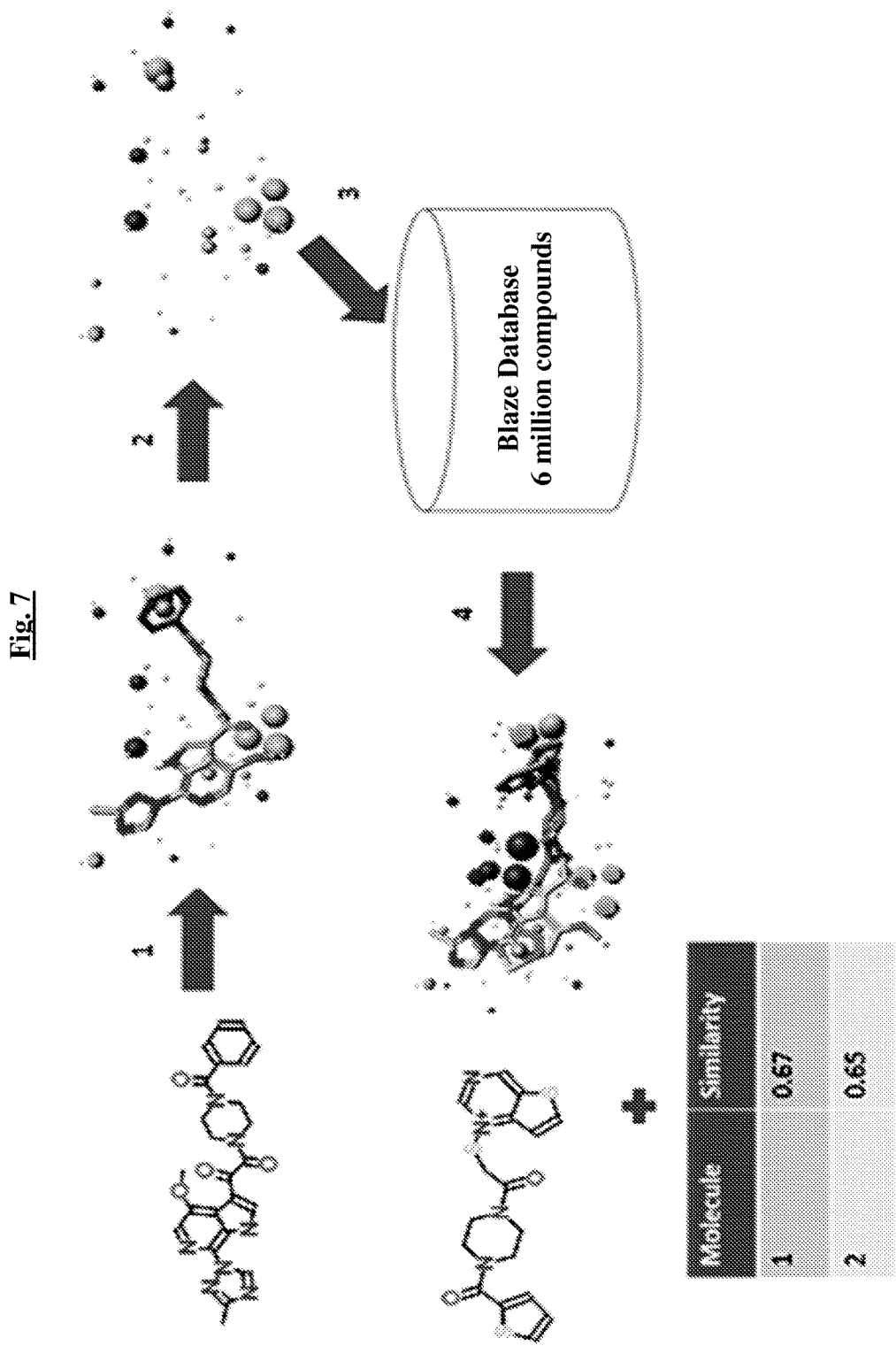
FIG. 7 is a schematic representation of the steps involved in a Blaze virtual screen experiment. (1) An active molecule is selected and converted to a relevant bioactive conformation; (2) field points are added to this search ligand in the specified conformation to produce the Blaze pharmacophore seed; (3) the Blaze Search Query consists of the field point pattern of the pharmacophore seed, and is used to search the Blaze database by alignment of every structure using field points; (4) top scoring compounds are retrieved as 3D alignments to the search query, along with their score (molecular similarity based on 50% shape, 50% fields).

The field point pattern for the hypothesized binding mode of BMS-626529 was subsequently used to query a database of approximately 6 million commercially available compounds using Blaze (Cresset, UK). The steps involved in the Blaze virtual screening procedure is shown schematically in FIG. 7. The Blaze procedure resulted in the rank ordering of the top 1,000 commercially available compounds whose 3D arrangements of field points had similarities to that of BMS-626529. Fifty compounds were selected for biological testing using the single-round infection assay.

Those compounds found to be active and specific, as judged by their activity against HIV-1YU-2 Env pseudotyped and AMLV Env pseudotyped HIV-1 virus, illustrated in Table 3. Five compounds with specific anti-HIV-1 activity were identified using this approach with half-maximal inhibitory concentrations ($IC_{50}$) in the range 13-150 μM. Compound SC03 was found to be the most potent, inhibiting HIV-1YU-2 with an $IC_{50}$ value of 13.1±1.7 μM.

In certain embodiments, the compounds of the invention, despite showing a degree of chemical diversity, all share a piperazine core. Studies were thus run to determine whether or not the piperazine may be replaced with a chemically distinct moiety, such as a dipyrrolidine group, in compound SC03. In silico bioisostere replacement experiments using Spark (Cresset, UK) of the potential ability of this group to substitute for the piperazine in SC03 indicated that it may be a viable replacement. This conclusion was based upon the value of the calculated Bioisostere factor (BIF %), a scaled score, which indicates how much better or worse the replacement is compared to simply capping the attachment point(s) with hydrogen(s)—capping with hydrogens is assigned a BIF % of zero. Positive BIF % values indicate good bioisosteres; negative values correspond to replacements where the geometry of the original molecule is reproduced, however, the fragment is not a good mimic of the replaced part. In the present case, a BIF % of 57 was obtained.

Substitution of the piperazine core in SC03 with 2-methyloctahydropyrrolo[3,4-c]pyrrole yielded compound SC04 ([5-(1,2-dihydro acenaphthylene-5-carbonyl)-1,3,3a,4,6,6a-hexahydropyrrolo[3,4-c]pyrrol-2-yl]-phenyl-methanone), a novel compound that retains the properties of SC03, albeit with lower potency ($IC_{50}$ HIV-1YU-2=70±6 μM; $IC_{50}$ HIV-1JR-CSF=100±30 μM;).

Having identified a new core scaffold, compound SC04 was redesigned to improve potency and to remove any potential toxophores. The head region of SC04, like compound SC03, is an acenaphthene group. In certain embodiments, this head region of the molecule greatly influences the potency of compounds in the piperazine class. Subsequently, in order to improve the potency of SC04, 453 compounds that displayed similarity to BMS-488043 were downloaded from PubChem and fragmented, and t iterative Spark experiments were employed, searching for fragments that could function as bioisosteres of the acenaphthene moiety but with greater potential for hydrogen bonding interactions. This resulted in the identification of two head groups, 7-chloro-4-methoxy-1H-pyrrolo[2,3-c]pyridine and 4,7-dimethoxy-1H-pyrrolo[2,3-c]pyridine, with BIF % values to acenaphthene of 57 and 64, respectively. Two compounds bearing these head groups were synthesized, compounds SC07 and SC08, and assessed in the single round infection assay. Due to the relative decreased sensitivity of HIV-1JR-CSF to SC04, as compared to HIV-1YU-2, this isolate was used for potency optimization. Both compounds were specific to HIV-1 (no inhibition of AMLV-pseudotyped HIV-1) and inhibited HIV-1JR-CSF pseudotyped HIV-1 virus with $IC_{50}$ values of 0.98±0.06 μM and 0.09±0.01 μM, for SC07 and SC08, respectively.

SC11 was synthesized and tested for specificity and activity against HIV-1JR-CSF using the single round infection assay. SC11 displayed greatly enhanced potency as compared to SC08, retaining HIV-1 specificity and inhibiting HIV-1JR-CSF with an $IC_{50}$ value of 0.0008±0.0004 μM.

Figure 8:
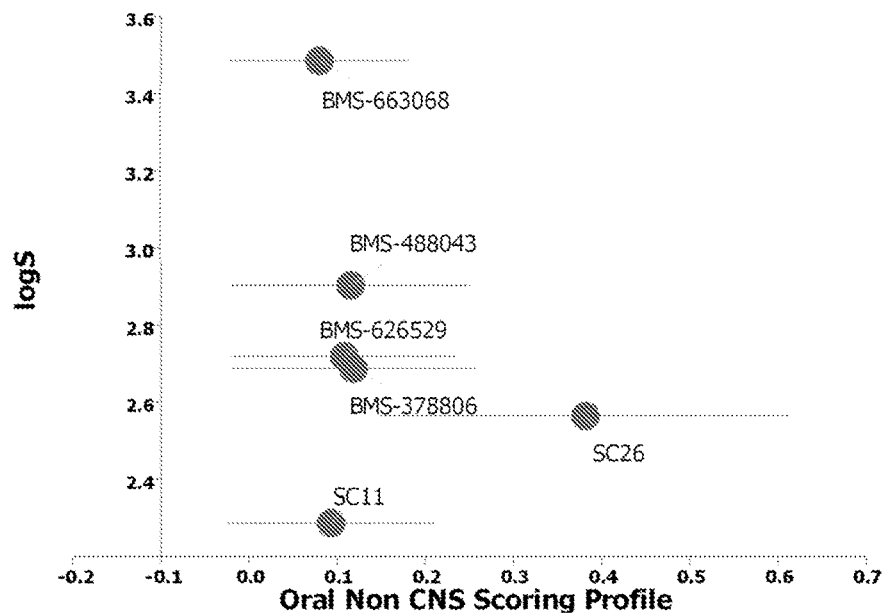
FIG. 8 is a graph illustrating the StarDrop (Optibrium Ltd., UK) derived log S versus the score from a multi-metric oral non-CNS profile for the BMS and SC compounds.

With the synthesis of SC11, it was demonstrated that the dipyrrolidine core can support nanomolar potency compounds that prevent HIV-1 entry. Next, the predicted ADME properties of this compound were analyzed and compared to the BMS piperazine-based entry inhibitors. A combination of computationally guided bioisosteric replacement using Spark v10, focusing on the terminal phenyl group of SC11, and in silico prediction of drug-like metrics of the results as implemented in StarDrop v5 (Optibrium Ltd., UK), were used. This yielded a simple replacement, phenyl to cyclohexene, with a high BIF % score along with improved predicted drug-like properties over both SC11 and the piperazine-based entry inhibitors (FIG. 8). This compound, compound SC26, was synthesized and subjected to specificity and potency analysis using the single round infection assay. Gratifyingly, this compound exhibited IC50 values of 2.0±0.1 nM and 0.6±0.01 nM against HIV-1$_{JR\text{-}CSF}$ and HIV-1$_{HxBc2}$, respectively.

Having demonstrated good potency against two isolates in the single round infection assay as well as specificity to HIV-1, the potency of SC26 was quantified against the fully infectious virus. Moreover, this assay was performed using healthy, primary cells to gain further insight into potential toxicities of the compound towards natural target cells. Additionally, as a key issue in the development of novel HIV drugs is their ability to inhibit the replication of genetically diverse isolates (especially isolates from the most globally prevalent subtypes A, B, C, and D), it was chosen to assess the potency of SC26 to inhibit the replication of isolates from subtypes A, B, C, and D in primary human peripheral blood mononuclear cells (PBMCs). Concomitantly, toxicity of SC26 to the PBMCs was assessed using an MTT assay. The results of these analyses are summarized in Table 5. As can be observed from the IC$_{50}$ values, the potency of SC26 against different isolates ranges quite dramatically, most likely reflecting differences in the binding site between subtypes. Moreover, SC26 had no effect on the replication of an HIV-2 isolate, mirroring the specificity analyses using the AMLV pseudoptyped recombinant HIV-1 virus, and further demonstrating specificity to HIV-1.

In summary, a novel scaffold for the HIV-1 Env-directed entry inhibitors was identified using field based computational methods and multiparameter optimization. The most potent in the new class of dipyrrolodine-scaffolded entry inhibitors displayed potency comparable to the BMS piperazine-based entry inhibitors, but was characterized by an improved predicted ADME profile. The new dipyrrolidine scaffold displayed varying degrees of potency against HIV-1 isolates from different subtypes, most probably reflecting isolate specific differences in the binding site on Env. Taken as a whole, these results extend the chemotypes for this class of HIV-1 inhibitor and validate the use of multiparameter optimization using high-content 3D field based models, bioisosteric replacement, and consideration of drug-like metrics in drug-design.

Example 11: Single Round Infection Assay

All compounds were evaluated in the single round infection assay. Single-round infectious envelope-pseudotyped luciferase reporter viruses were produced in 293T cells co-transfected by calcium phosphate precipitation with the envelope deficient HIV-1 NL-4-3 vector (pNL-4-3-LucR$^+$ E$^-$; a gift of N. R. Landau, The Salk Institute for Biological Studies), which carries the luciferase reporter gene; and either the HIV-1 envelope-expressing vectors of interest or the envelope from amphotrophic murine leakemia virus (as a specificity control). After 6 hours of incubation at 37° C., the DNA-containing medium was removed, cells were washed and fresh medium containing sodium butyrate was added. Supernatants containing the envelope-pseudotyped viruses were collected 2 days later, clarified, aliquoted and stored at −80° C. until use. Pseudotype stocks were quantified by p24$^{gag}$ content (NEN, Brussels, Belgium).

To functionally test for the ability of the compounds to inhibit viral entry/infection, compounds were diluted in regular medium and added to target cells (U87-C4-CCR5 or U87-CD4-CXCR4) at 2-fold the final desired concentration. An equal volume of similar amounts of envelope-pseudotyped luciferase viruses (normalized by p24$^{gag}$) diluted in regular medium, was immediately added to the cells for infection. After 6 hours of incubation at 37° C., the virus-containing medium was removed and fresh medium was added. Two to three days after infection, the cells were washed with PBS and lysed with luciferase assay buffer (60 µl/well; Promega, Madison, Wis.). Luciferase activity was determined by adding 50 µl of freshly prepared luciferase assay substrate (Promega) to an equal volume of lysate in solid white microplates and measuring the intensity of chemiluminescence in a microplate luminometer. All experiments were performed at least in triplicate. Results are expressed as relative infection with respect to untreated (100%).

Selected compounds of the invention were evaluated in a single round infection assay. Table 3 illustrates results of the assay. As illustrated in Tables 2-3, each of these compounds were specific to HIV-1 but exhibited a range of potencies from 2 nM to 2 µM. Without wishing to be limited by any theory, placement of the azetidine group towards the azaindole head group allows for potencies in the nanomolar range. This orientation may influence the particular range of conformations of the compounds, altering their ability to engage in high energy interactions within the binding site.

Example 12

The aqueous solubility (log S) and the oral non-CNS profile score for Compound SC12 (also known as 1-(4-methoxy-7-(3-methyl-1H-1,2,4-triazol-1-yl)-1H-pyrrolo[2,3-c]pyridin-3-yl)-2-(1-phenyl-3a,4,6,6a-tetrahydropyrrolo[3,4-c]pyrazol-5(1H)-yl)ethane-1,2-dione, or a salt thereof) was determined using StarDrop Build 5.2 (Optibrium Ltd., Cambridge, UK).

Reference compounds included compounds such as BMS-663068, BMS-626529, BMS-488043, BMS-377806, and raltegravir (FIG. 1).

Figure 2:
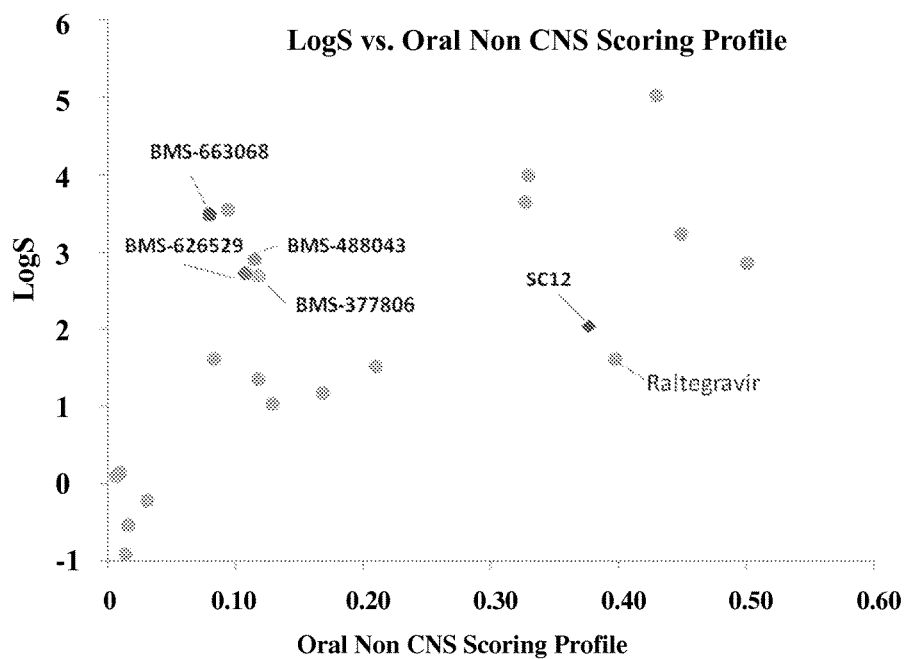
FIG. 2 is a graph illustrating the aqueous solubility versus oral non-central nervous system ("non-CNS") profile score for selected compounds.
Figure 3:
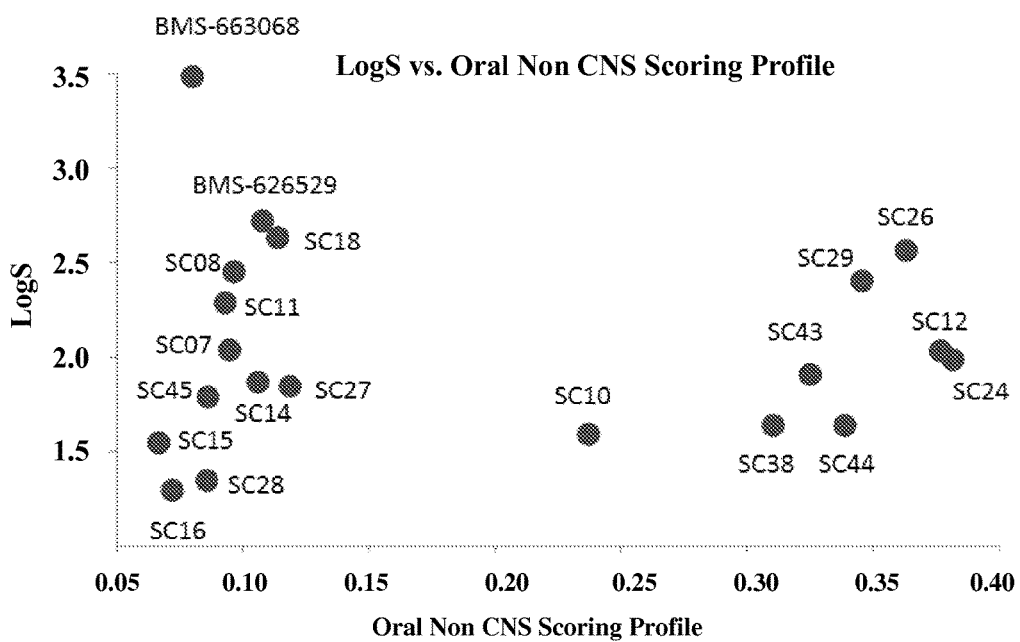
FIG. 3 is a graph illustrating the aqueous solubility versus oral non-central nervous system ("non-CNS") profile score for selected compounds.
Figure 4:
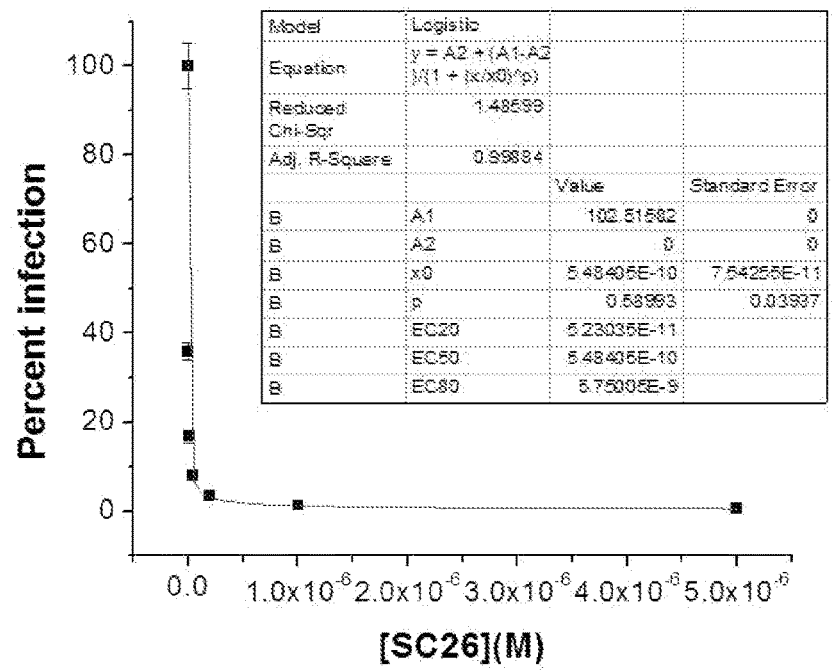
FIG. 4 is a graph illustrating the potency of SC26 against the HIV-1 isolate HxBc2.
Figure 5:
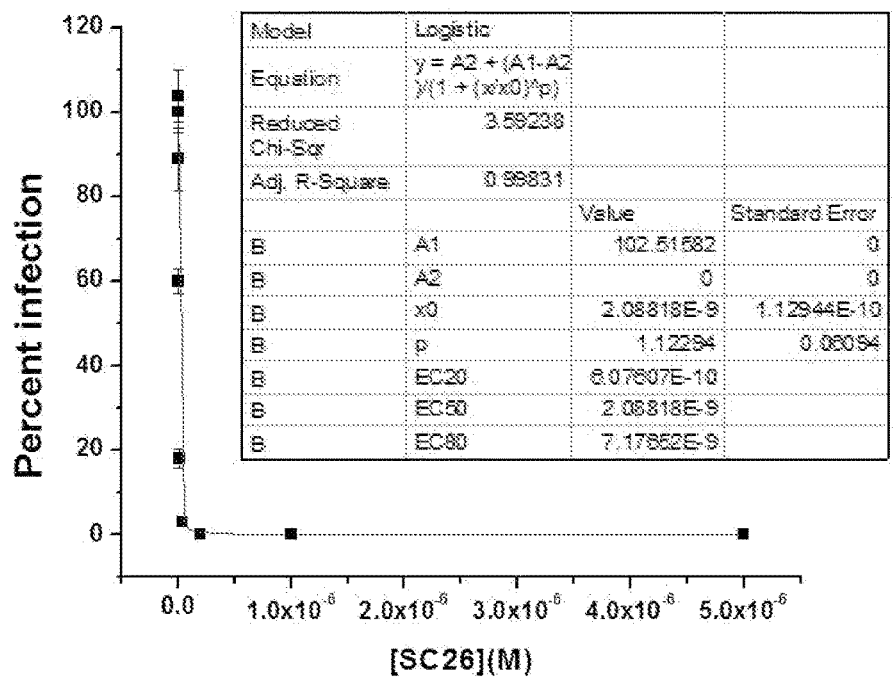
FIG. 5 is a graph illustrating the potency of SC26 against the HIV-1 isolate JR-CSF.

As illustrated in FIG. 2, Compound SC12 showed a better predicted oral non-CNS score than the reference compounds, including prodrug BMS-663068. The score for SC12 was similar to that of raltegravir (an integrase inhibitor used in the clinic). Compound SC13 (1-(4-methoxy-7-(3-methyl-1H-1,2,4-triazol-1-yl)-1H-pyrrolo[2,3-c]pyridin-3-yl)-2-(2-oxo-1-phenyl-2,3,4,6-tetrahydropyrrolo[3,4-d]imidazol-5(1H)-yl)ethane-1,2-dione) also showed a high predicted oral non-CNS score.

Table 4 illustrates the potency of Compound SC12 against selected HIV-1 isolates using the single round infection assay.

TABLE 2

Single Round Infection Assay
(Screening Results; numbering applies only to Table 2)

| Compound | Structure | IC$_{50}$ YU-2 (µM) | IC$_{50}$ AMLV (µM) |
|---|---|---|---|
| 1 | 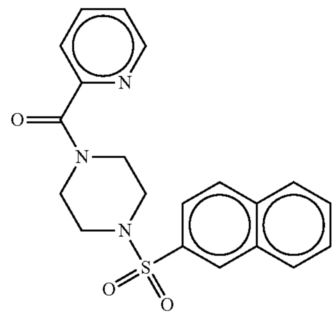 | >300 | >300 |
| 2 | 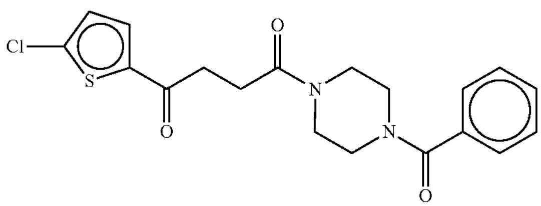 | >300 | >300 |
| 3 | 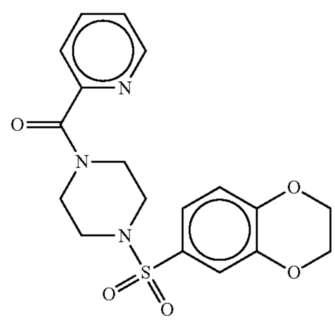 | >300 | >300 |
| 4 | 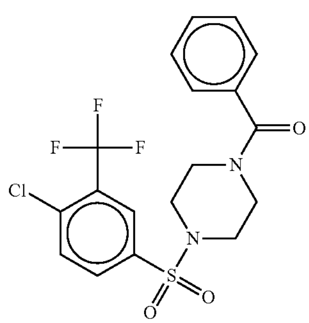 | >300 | >300 |
| 5 | 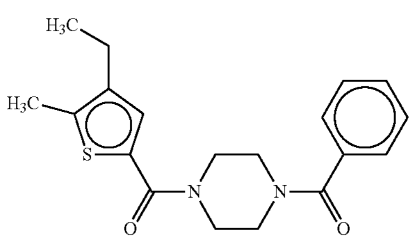 | >300 | >300 |

TABLE 2-continued

Single Round Infection Assay
(Screening Results; numbering applies only to Table 2)

| Compound | Structure | IC$_{50}$ YU-2 (μM) | IC$_{50}$ AMLV (μM) |
|---|---|---|---|
| 6 | 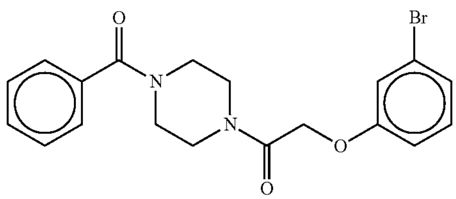 | >300 | >300 |
| 7 | 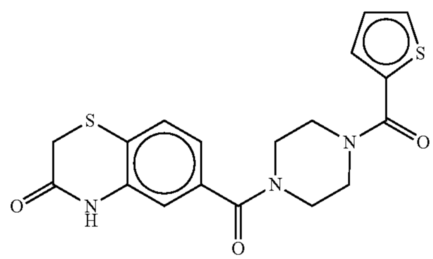 | >300 | >300 |
| 8 | 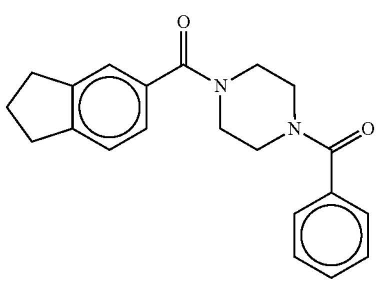 | >300 | >300 |
| 9 | 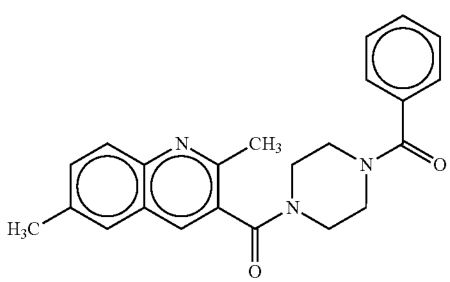 | >300 | >300 |
| 10 | 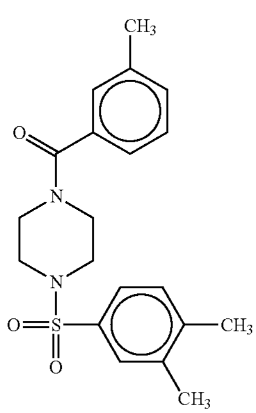 | >300 | >300 |

TABLE 2-continued

Single Round Infection Assay
(Screening Results; numbering applies only to Table 2)

| Compound | Structure | IC$_{50}$ YU-2 (μM) | IC$_{50}$ AMLV (μM) |
|---|---|---|---|
| 11 | 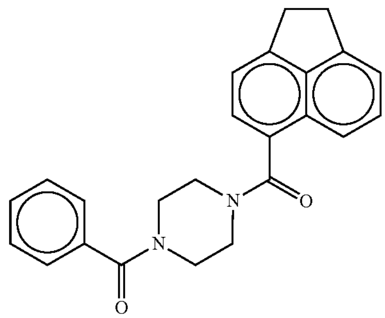 | 15.7 | >300 |
| 12 | 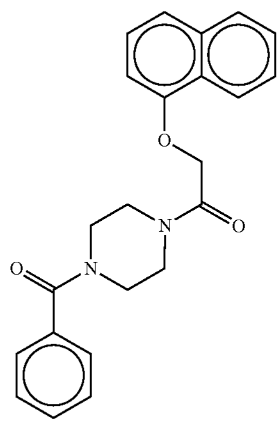 | 53.3 ± 3.7 | >300 |
| 13 | 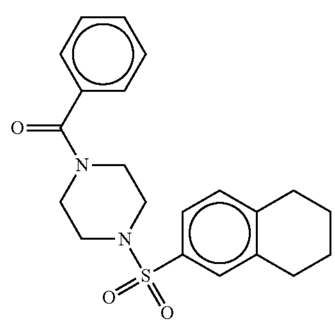 | 116.6 | 196.8 |
| 14 | 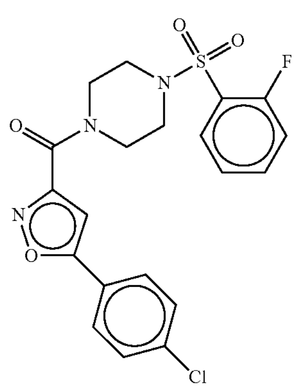 | >300 | >300 |

TABLE 2-continued

Single Round Infection Assay
(Screening Results; numbering applies only to Table 2)

| Compound | Structure | IC$_{50}$ YU-2 (μM) | IC$_{50}$ AMLV (μM) |
|---|---|---|---|
| 15 | 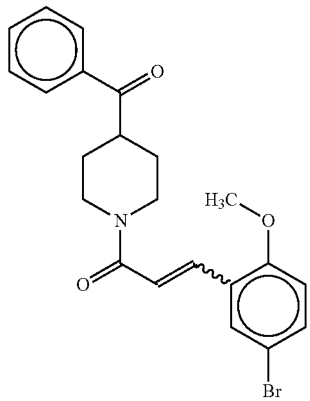 | 156.3 | 210.5 |
| 16 | 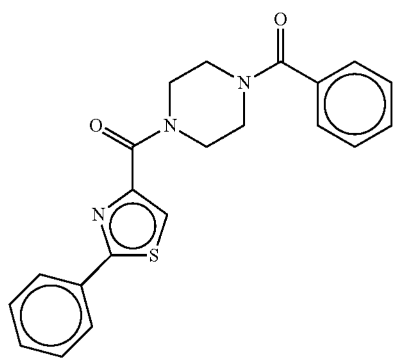 | >300 | >300 |
| 17 | 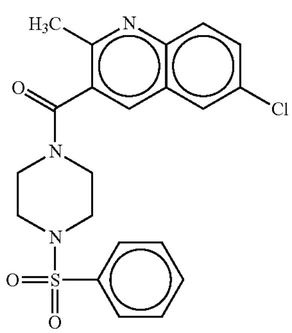 | 193.2 | 237.9 |
| 18 | 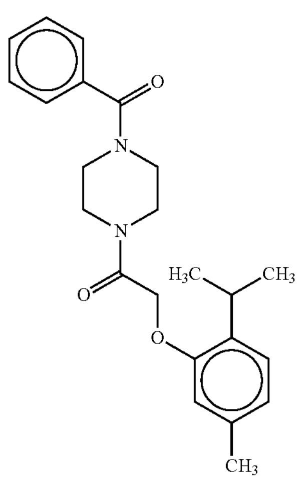 | >300 | >300 |

TABLE 2-continued

Single Round Infection Assay
(Screening Results; numbering applies only to Table 2)

| Compound | Structure | IC$_{50}$ YU-2 (µM) | IC$_{50}$ AMLV (µM) |
|---|---|---|---|
| 19 | 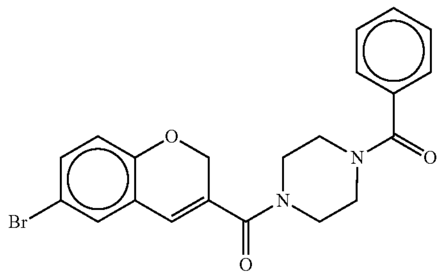 | >300 | >300 |
| 20 | 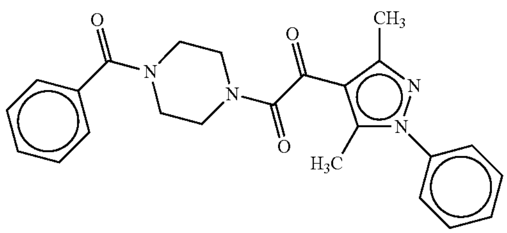 | >300 | >300 |
| 21 | 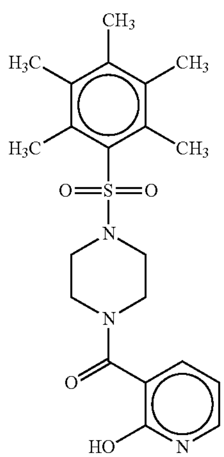 | >300 | >300 |
| 22 | 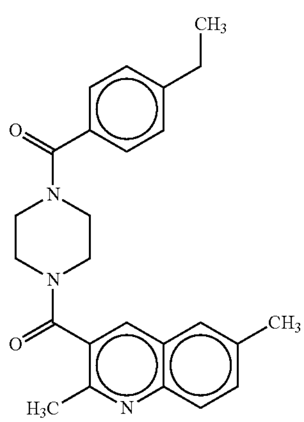 | >300 | >300 |

TABLE 2-continued
Single Round Infection Assay
(Screening Results; numbering applies only to Table 2)
| Compound | Structure | IC$_{50}$ YU-2 (μM) | IC$_{50}$ AMLV (μM) |
|---|---|---|---|
| 23 | 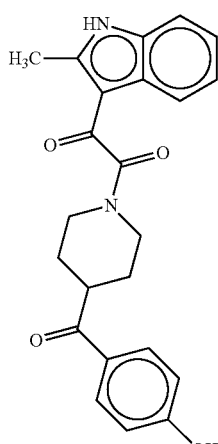 | >300 | >300 |
| 24 | 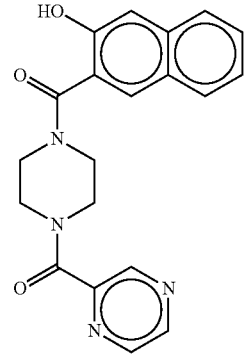 | >300 | >300 |
| 25 | 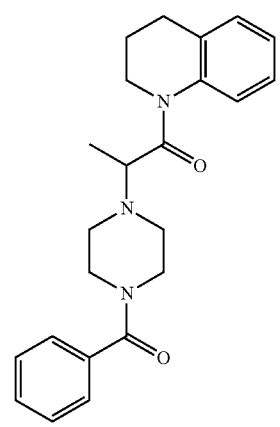 [SMILES: CC(C(=O)N1CCCc2ccccc21)N1CCN(C(=O)c2ccccc2)CC1] | >50 | >50 |

TABLE 2-continued

Single Round Infection Assay
(Screening Results; numbering applies only to Table 2)

| Compound | Structure | IC$_{50}$ YU-2 (μM) | IC$_{50}$ AMLV (μM) |
|---|---|---|---|
| 26 | 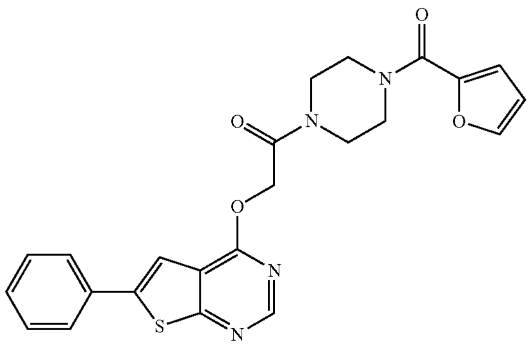 [SMILES: O=C(COc1ncnc2sc(-c3ccccc3)cc12)N1CCN(C(=O)c2ccco2)CC1] | >50 | >50 |
| 27 | 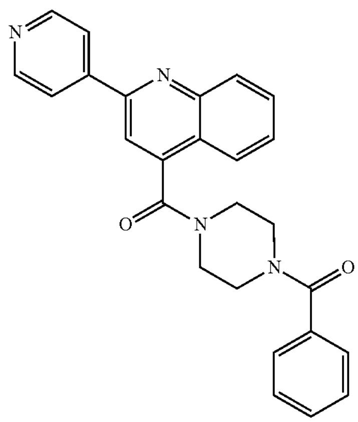 [SMILES: O=C(c1ccccc1)N1CCN(C(=O)c2cc(-c3ccncc3)nc3ccccc23)CC1] | >50 | >50 |
| 28 | 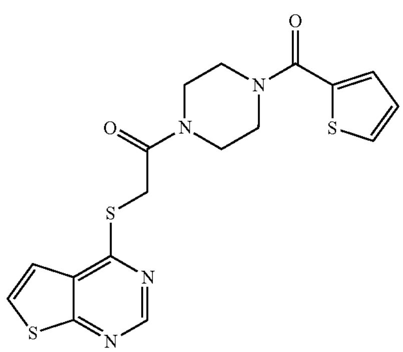 [SMILES: O=C(CSc1ncnc2sccc12)N1CCN(C(=O)c2cccs2)CC1] | 1.6 ± 0.4 | >50 |
| 29 | 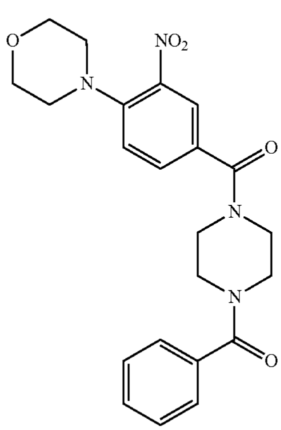 [SMILES: O=C(c1ccccc1)N1CCN(C(=O)c2ccc(N3CCOCC3)c([N+](=O)[O-])c2)CC1] | >50 | >50 |

TABLE 2-continued

Single Round Infection Assay
(Screening Results; numbering applies only to Table 2)

| Compound | Structure | IC$_{50}$ YU-2 (µM) | IC$_{50}$ AMLV (µM) |
|---|---|---|---|
| 30 | 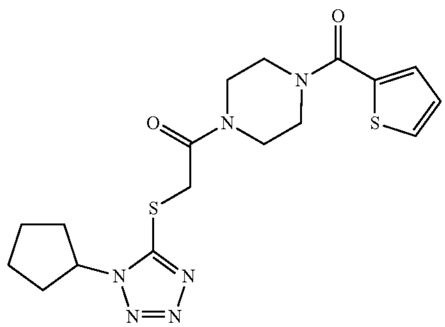 [SMILES: O=C(CSc1nnnn1C1CCCC1)N1CCN(C(=O)c2cccs2)CC1] | >50 | >50 |
| 31 | 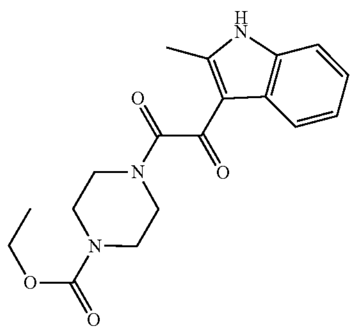 [SMILES: CCOC(=O)N1CCN(C(=O)C(=O)c2c(C)[nH]c3ccccc23)CC1] | >50 | >50 |
| 32 | 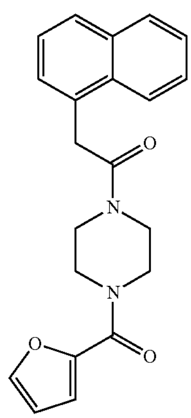 [SMILES: O=C(Cc1cccc2ccccc12)N1CCN(C(=O)c2ccco2)CC1] | 22.8 | >50 |
| 33 | 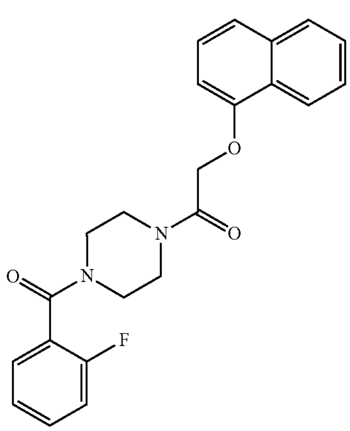 [SMILES: O=C(COc1cccc2ccccc12)N1CCN(C(=O)c2ccccc2F)CC1] | >50 | >50 |

TABLE 2-continued
Single Round Infection Assay
(Screening Results; numbering applies only to Table 2)
| Compound | Structure | IC$_{50}$ YU-2 (µM) | IC$_{50}$ AMLV (µM) |
|---|---|---|---|
| 34 | 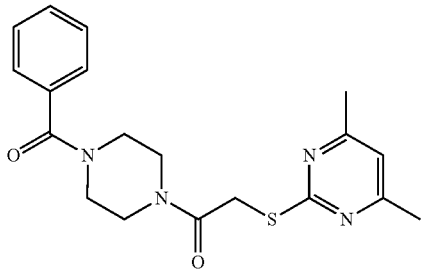 [SMILES: Cc1cc(C)nc(SCC(=O)N2CCN(C(=O)c3ccccc3)CC2)n1] | 19.4 | >50 |
| 35 | 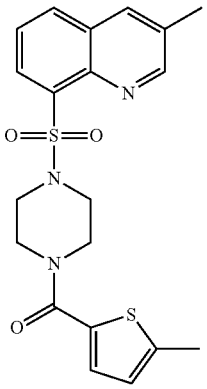 [SMILES: Cc1cnc2c(S(=O)(=O)N3CCN(C(=O)c4ccc(C)s4)CC3)cccc2c1] | >50 | >50 |
| 36 | 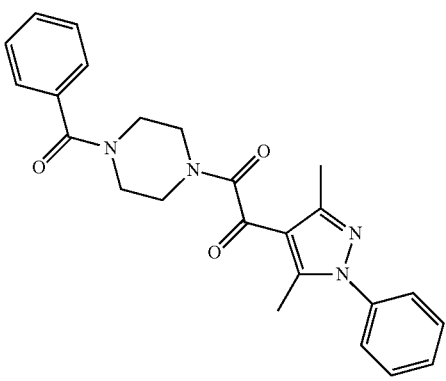 [SMILES: Cc1nn(-c2ccccc2)c(C)c1C(=O)C(=O)N1CCN(C(=O)c2ccccc2)CC1] | >50 | >50 |
| 37 | 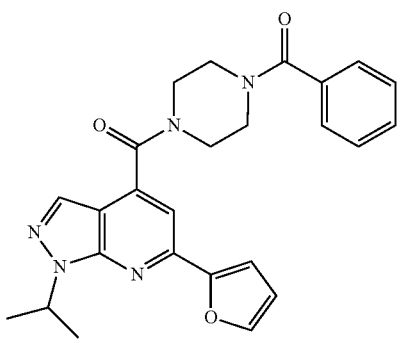 [SMILES: CC(C)n1ncc2c(C(=O)N3CCN(C(=O)c4ccccc4)CC3)cc(-c3ccco3)nc21] | >50 | >50 |

TABLE 2-continued

Single Round Infection Assay
(Screening Results; numbering applies only to Table 2)

| Compound | Structure | IC$_{50}$ YU-2 (µM) | IC$_{50}$ AMLV (µM) |
|---|---|---|---|
| 38 | 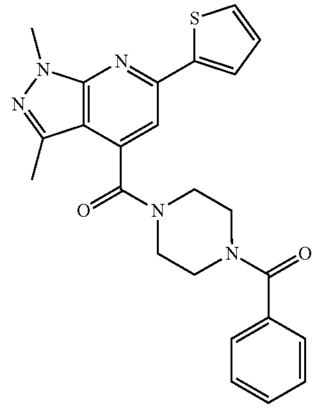 [SMILES: Cc1nn(C)c2nc(-c3cccs3)cc(C(=O)N3CCN(C(=O)c4ccccc4)CC3)c12] | >50 | >50 |
| 39 | 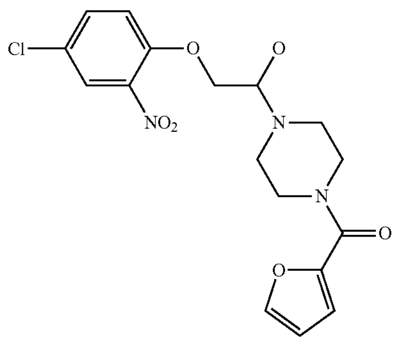 [SMILES: O=C(c1ccco1)N1CCN(C(O)COc2ccc(Cl)cc2[N+](=O)[O-])CC1] | >50 | >50 |
| 40 | 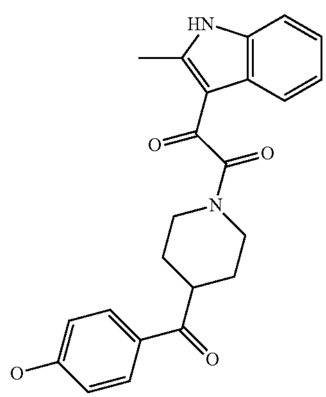 [SMILES: Cc1[nH]c2ccccc2c1C(=O)C(=O)N1CCC(C(=O)c2ccc(O)cc2)CC1] | >50 | >50 |
| 41 | 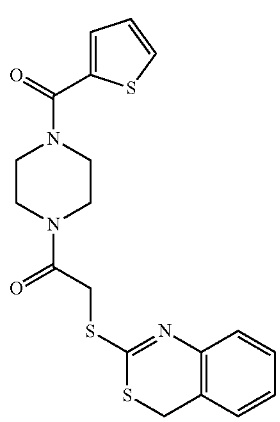 [SMILES: O=C(CSC1=Nc2ccccc2CS1)N1CCN(C(=O)c2cccs2)CC1] | >50 | >50 |

TABLE 2-continued

Single Round Infection Assay
(Screening Results; numbering applies only to Table 2)

| Compound | Structure | IC$_{50}$ YU-2 (µM) | IC$_{50}$ AMLV (µM) |
|---|---|---|---|
| 42 | 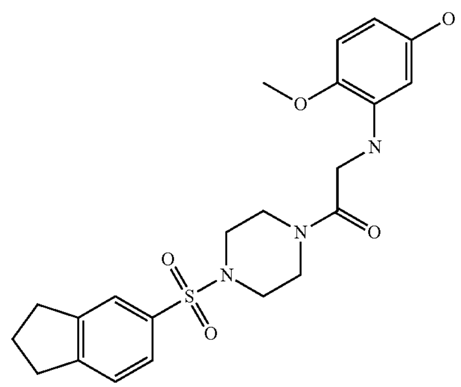 [SMILES: COc1ccc(O)cc1NCC(=O)N1CCN(S(=O)(=O)c2ccc3c(c2)CCC3)CC1] | >50 | >50 |
| 43 | 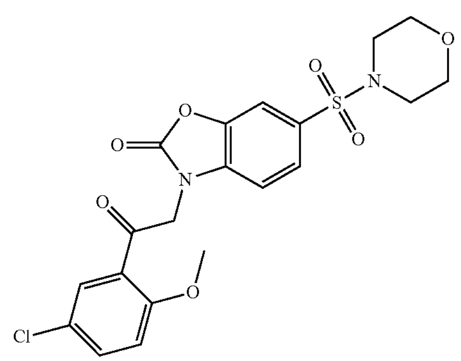 [SMILES: COc1ccc(Cl)cc1C(=O)Cn1c(=O)oc2cc(S(=O)(=O)N3CCOCC3)ccc21] | >50 | >50 |
| 44 | 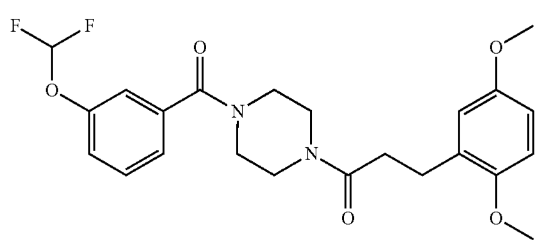 [SMILES: COc1ccc(OC)c(CCC(=O)N2CCN(C(=O)c3cccc(OC(F)F)c3)CC2)c1] | >50 | >50 |
| 45 | 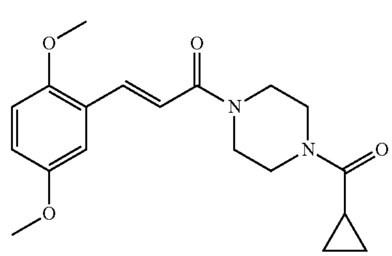 [SMILES: COc1ccc(OC)c(/C=C/C(=O)N2CCN(C(=O)C3CC3)CC2)c1] | >50 | >50 |

TABLE 2-continued
Single Round Infection Assay
(Screening Results; numbering applies only to Table 2)
| Compound | Structure | IC$_{50}$ YU-2 (μM) | IC$_{50}$ AMLV (μM) |
|---|---|---|---|
| 46 | 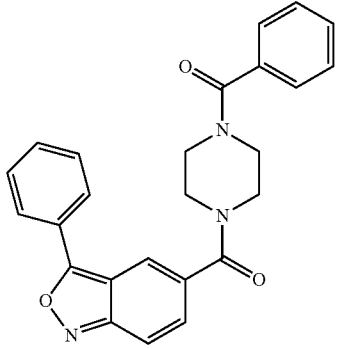 [SMILES: O=C(c1ccccc1)N1CCN(C(=O)c2ccc3noc(-c4ccccc4)c3c2)CC1] | >50 | >50 |
| 47 | 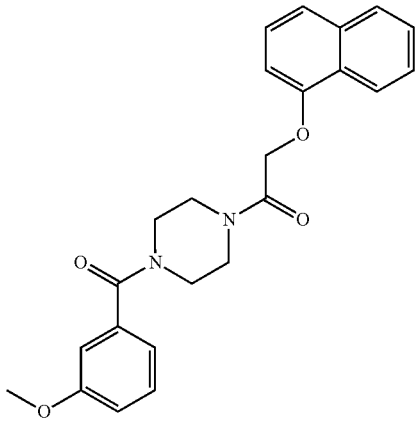 [SMILES: COc1cccc(C(=O)N2CCN(C(=O)COc3cccc4ccccc34)CC2)c1] | >50 | >50 |
| 48 | 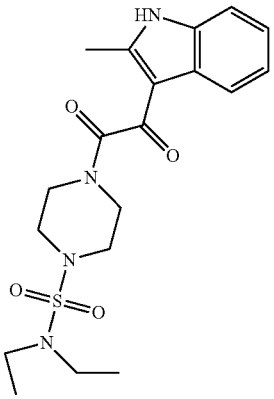 [SMILES: CCN(CC)S(=O)(=O)N1CCN(C(=O)C(=O)c2c(C)[nH]c3ccccc23)CC1] | >50 | >50 |

TABLE 2-continued
Single Round Infection Assay
(Screening Results; numbering applies only to Table 2)
| Compound | Structure | IC$_{50}$ YU-2 (µM) | IC$_{50}$ AMLV (µM) |
|---|---|---|---|
| 49 | 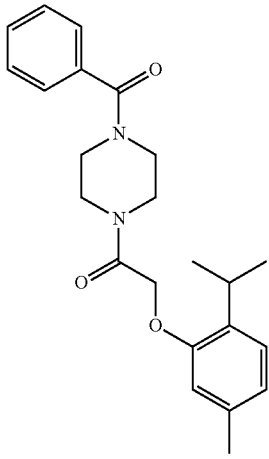 [SMILES: Cc1ccc(C(C)C)c(OCC(=O)N2CCN(C(=O)c3ccccc3)CC2)c1] | >50 | >50 |
| 50 | 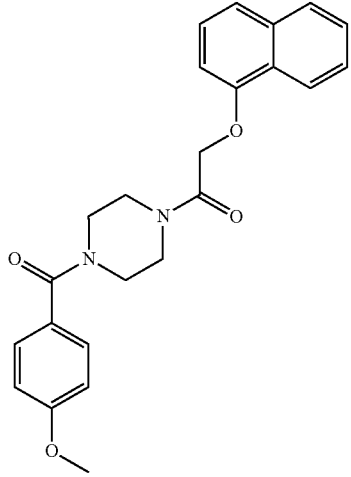 [SMILES: COc1ccc(C(=O)N2CCN(C(=O)COc3cccc4ccccc34)CC2)cc1] | >50 | >50 |
TABLE 3
Single Round Infection Assay
| Compound Number | Structure | IC$_{50}$ JR-CSF (µM) | IC$_{50}$ HxBc2 (µM) | IC$_{50}$ AMLV (µM) |
|---|---|---|---|---|
| SC03 | 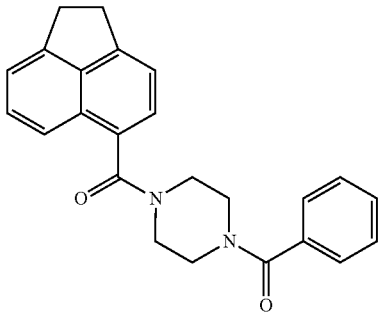 [SMILES: O=C(c1ccccc1)N1CCN(C(=O)c2ccc3c4c(cccc24)CC3)CC1] | 0.42 ± 0.28 | N.D. | N.A. |

TABLE 3-continued

Single Round Infection Assay

| Compound Number | Structure | IC$_{50}$ JR-CSF (μM) | IC$_{50}$ HxBc2 (μM) | IC$_{50}$ AMLV (μM) |
| --- | --- | --- | --- | --- |
| SC04 | 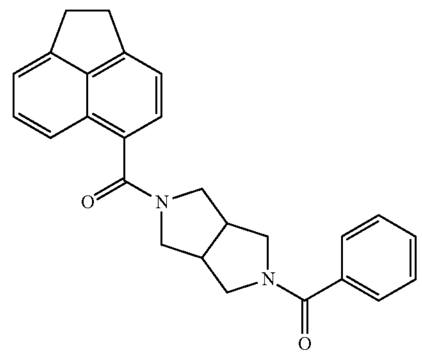 [SMILES: O=C(c1ccccc1)N1CC2CN(C(=O)c3ccc4c5c(cccc35)CC4)CC2C1] | 100 ± 30 | N.D. | N.A. |
| SC07 | 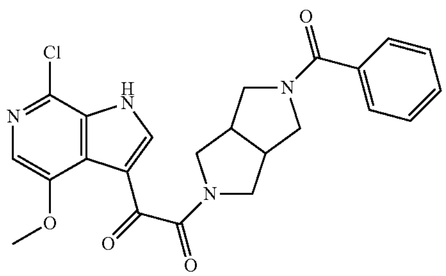 [SMILES: COc1cnc(Cl)c2[nH]cc(C(=O)C(=O)N3CC4CN(C(=O)c5ccccc5)CC4C3)c12] | 0.98 ± 0.06 | 16.8 ± 6.2 | N.A. |
| SC08 | 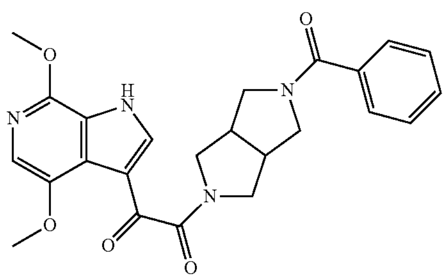 [SMILES: COc1ncc(OC)c2c(C(=O)C(=O)N3CC4CN(C(=O)c5ccccc5)CC4C3)c[nH]c12] | 0.09 ± 0.01 | 0.19 ± 0.08 | N.A. |
| SC10 | 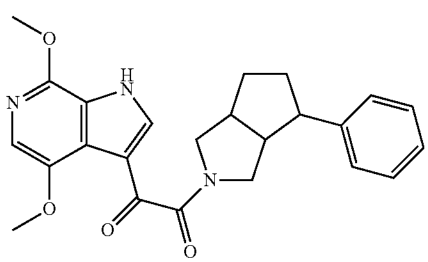 [SMILES: COc1ncc(OC)c2c(C(=O)C(=O)N3CC4CCC(c5ccccc5)C4C3)c[nH]c12] | 0.42 ± 0.11 | 4.81 ± 4.1 | N.A. |
| SC11 | 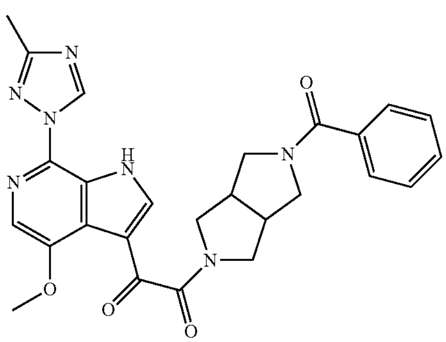 [SMILES: COc1cnc(-n2cnc(C)n2)c2[nH]cc(C(=O)C(=O)N3CC4CN(C(=O)c5ccccc5)CC4C3)c12] | 0.0008 ± 0.0004 | 0.001 ± 0.0001 | N.A. |

TABLE 3-continued

| | Single Round Infection Assay | | | |
|---|---|---|---|---|
| Compound Number | Structure | IC$_{50}$ JR-CSF (μM) | IC$_{50}$ HxBc2 (μM) | IC$_{50}$ AMLV (μM) |
| SC12 | | 0.008 ± 0.002 | 0.08 ± 0.02 | N.A. |
| SC14 | | 2.5 ± 0.4 | 1.2 ± 0.4 | N.A. |
| SC15 | | 0.002 ± 0.0001 | 0.003 ± 0.0005 | N.A. |
| SC16 | | 0.1 ± 0.02 | 0.15 ± 0.03 | N.A. |

TABLE 3-continued

Single Round Infection Assay

| Compound Number | Structure | IC$_{50}$ JR-CSF (μM) | IC$_{50}$ HxBc2 (μM) | IC$_{50}$ AMLV (μM) |
|---|---|---|---|---|
| SC18 | 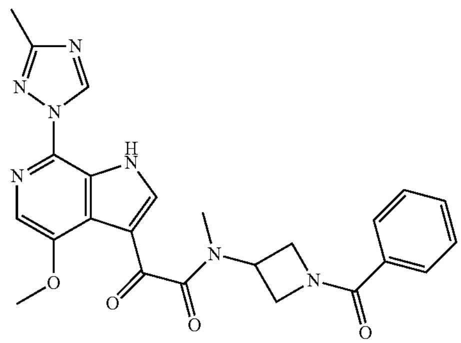 [SMILES: COc1cnc(-n2cnc(C)n2)c2[nH]cc(C(=O)C(=O)N(C)C3CN(C(=O)c4ccccc4)C3)c12] | 1.3 ± 0.2 | 102 ± 160 | N.A. |
| SC24 | 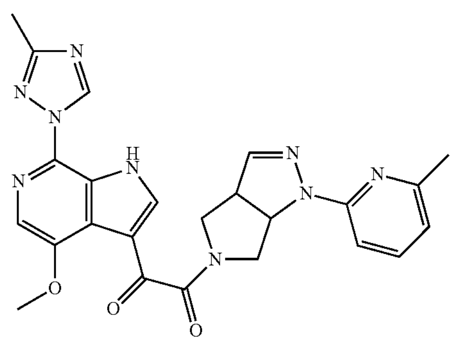 | 0.7 ± 0.4 | N.D. | N.A. |
| SC26 | 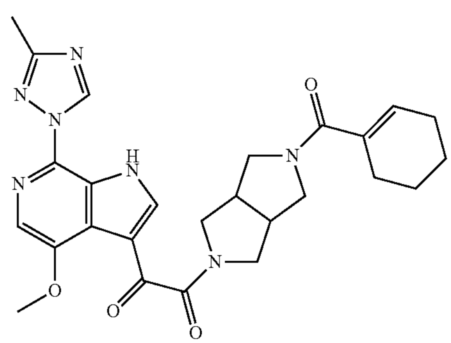 [SMILES: COc1cnc(-n2cnc(C)n2)c2[nH]cc(C(=O)C(=O)N3CC4CN(C(=O)C5=CCCCC5)CC4C3)c12] | 0.002 ± 0.0001 | 0.0006 ± 0.00008 | N.A. |
| SC27 | 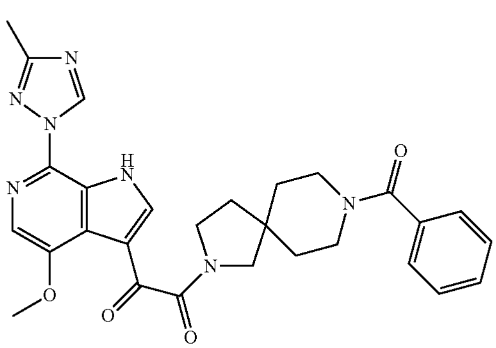 [SMILES: COc1cnc(-n2cnc(C)n2)c2[nH]cc(C(=O)C(=O)N3CCC4(CCN(C(=O)c5ccccc5)CC4)C3)c12] | | | |

TABLE 3-continued

Single Round Infection Assay

| Compound Number | Structure | IC₅₀ JR-CSF (μM) | IC₅₀ HxBc2 (μM) | IC₅₀ AMLV (μM) |
|---|---|---|---|---|
| SC28 | 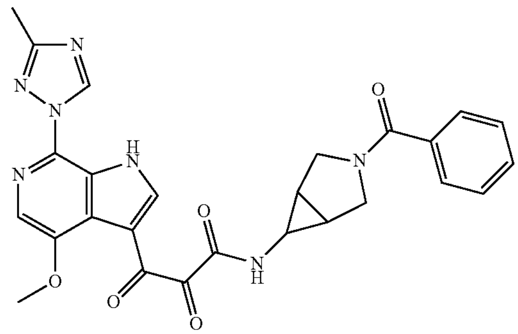 [SMILES: COc1cnc(-n2cnc(C)n2)c2[nH]cc(C(=O)C(=O)C(=O)NC3C4CN(C(=O)c5ccccc5)CC43)c12] | | | |
| SC29 | 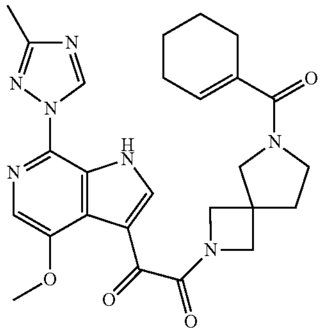 [SMILES: COc1cnc(-n2cnc(C)n2)c2[nH]cc(C(=O)C(=O)N3CC4(CCN(C(=O)C5=CCCCC5)C4)C3)c12] | | | |
| SC38 | 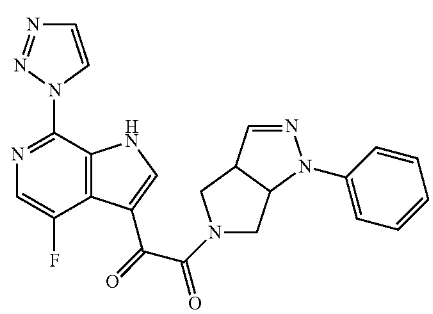 [SMILES: O=C(C(=O)N1CC2C=NN(c3ccccc3)C2C1)c1c[nH]c2c(-n3ccnn3)ncc(F)c12] | N.D. | 0.008 ± 0.003 | N.A. |
| SC39 | 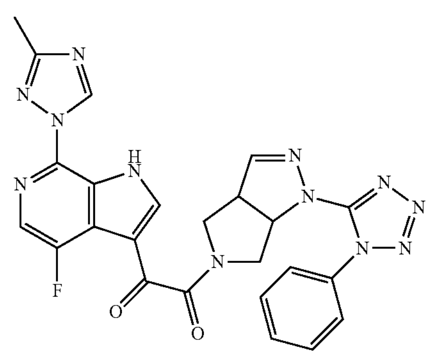 [SMILES: Cc1ncn(-c2ncc(F)c3c(C(=O)C(=O)N4CC5C=NN(c6nnnn6-c6ccccc6)C5C4)c[nH]c23)n1] | N.D. | 35.3 ± 9.3 | N.A. |

TABLE 3-continued

Single Round Infection Assay

| Compound Number | Structure | IC$_{50}$ JR-CSF (μM) | IC$_{50}$ HxBc2 (μM) | IC$_{50}$ AMLV (μM) |
|---|---|---|---|---|
| SC43 | 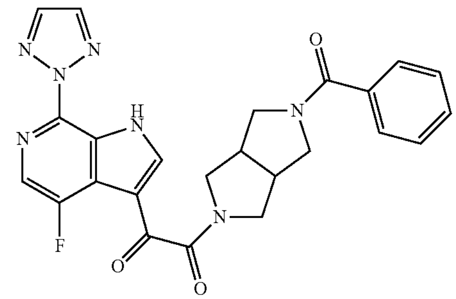 [SMILES: O=C(C(=O)N1CC2CN(C(=O)c3ccccc3)CC2C1)c1c[nH]c2c(-n3nccn3)ncc(F)c12] | N.D. | N.A. | N.A. |
| SC44 | 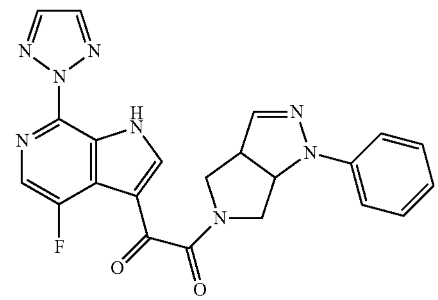 [SMILES: O=C(C(=O)N1CC2C=NN(c3ccccc3)C2C1)c1c[nH]c2c(-n3nccn3)ncc(F)c12] | N.D. | N.A. | N.A. |
| SC45 | 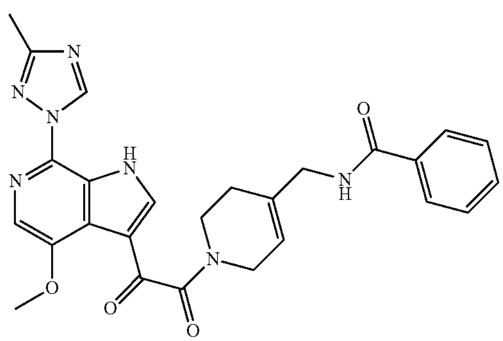 [SMILES: COc1cnc(-n2cnc(C)n2)c2[nH]cc(C(=O)C(=O)N3CC=C(CNC(=O)c4ccccc4)CC3)c12] | 0.15 ± 0.009 | 0.1 ± 0.03 | N.A. |

N.D. = not determined
N.A. = not active

TABLE 4

SC12's potency against selected HIV-1 isolates (single round infection assay)

| Isolate | Tropism | IC$_{50}$ (nM) |
|---|---|---|
| HxBc2 | X4 | 24.0 ± 3.0 |
| JR-CSF | R5 | 13.0 ± 3.0 |
| BaL | R5 | 3500 ± 300 |
| AC10.0.29 | R5 | 488 ± 47 |
| JR-FL | R5 | 106 ± 52 |

TABLE 5

Therapeutic spectrum of SC26 against highly prevalent HIV-1 subtypes and HIV-2. NA = not applicable.

| Virus Isolate | Subtype | IC$_{50}$ (μM) | TC$_{50}$ (μM) | Antiviral index (TC$_{50}$/IC$_{50}$) |
|---|---|---|---|---|
| 92UG037 | A | 25.2 ± 6.9 | >100 | >3.97 |
| 91US004 | B | 0.195 ± 0.012 | | >513 |
| 94US_3393IN | B | 0.0006 ± 0.0005 | | >166,666 |
| 98US_MSC5016 | C | 3.9 ± 0.8 | | >25.6 |
| 99UG_A07412M1 | D | 0.49 ± 0.06 | | >204 |
| HIV-2 CDC310319 | NA | >100 | | NA |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I), or a salt or solvate thereof:

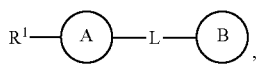

wherein:
R¹ is

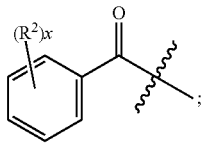

ring A is

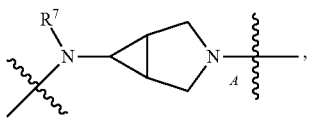

wherein the atom labeled with A is linked to ring R¹;
linker L is selected from the group consisting of:

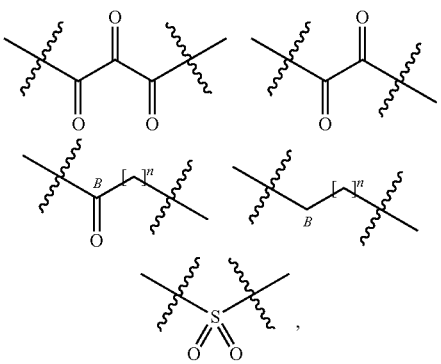

wherein the atom labeled with B is linked to ring B;
ring B is selected from the group consisting of:

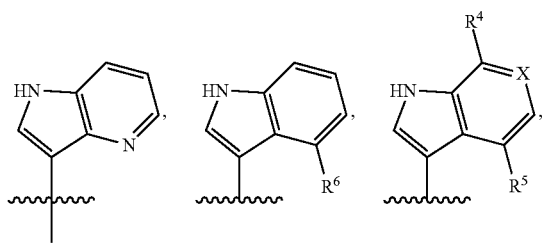

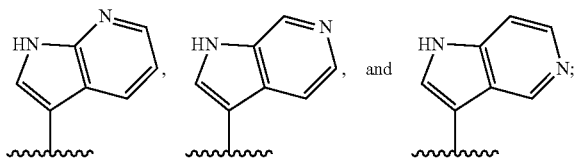

each occurrence of $R^2$ is independently selected from the group consisting of —$(C_1$-$C_6)$alkyl, —$(C_1$-$C_6)$fluoroalkyl, —F, —Cl, —Br, —I, and —$OR^7$;

$R^4$ is 1,2,4-triazolyl optionally substituted with $(C_1$-$C_6)$ alkyl;

$R^5$ is selected from the group consisting of H, —$(C_1$-$C_6)$ alkyl, —$(C_1$-$C_6)$fluoroalkyl, and —$OR^7$;

$R^6$ is H or F;

each occurrence of $R^7$ is independently selected from the group consisting of H and —$(C_1$-$C_6)$alkyl;

X is CH or N;

x is an integer from 0-5; and each occurrence of n is independently 0 or 1.

2. The compound of claim 1, wherein $R^1$ is

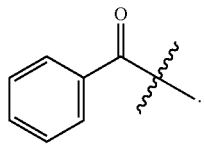 [SMILES: *C(=O)c1ccccc1]

3. The compound of claim 1, wherein the compound is N-(3-benzoyl-3-azabicyclo[3.1.0]hexan-6-yl)-3-(4-methoxy-7-(3-methyl-1H-1,2,4-triazol-1-yl)-1H-pyrrolo[2,3-c]pyridin-3-yl)-2,3-dioxopropanamide (SC28), or a salt, N-oxide or solvate thereof.

4. A pharmaceutical composition comprising at least one compound of claim 1 and at least one pharmaceutically acceptable carrier.

5. The composition of claim 4, further comprising at least one additional therapeutic agent useful for treating an HIV infection.

6. The composition of claim 5, wherein the at least one additional therapeutic agent comprises at least one selected from the group consisting of a HIV drug combination, entry and fusion inhibitor, integrase inhibitor, non-nucleoside reverse transcriptase inhibitor, nucleoside reverse transcriptase inhibitor, and protease inhibitor.

7. A method of treating an HIV-1 infection in a subject in need thereof, the method comprising administering to the subject a therapeutically effective amount of at least one compound of formula (I):

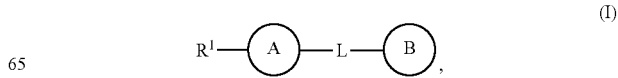

wherein:
R¹ is

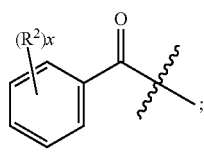

;

ring A is

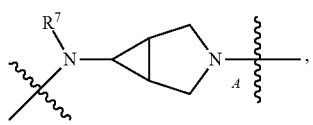

, wherein the atom labeled with A is linked to ring R¹; linker L is selected from the group consisting of:

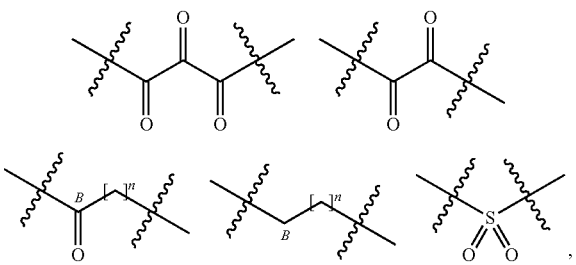

wherein the atom labeled with B is linked to ring B; ring B is selected from the group consisting of:

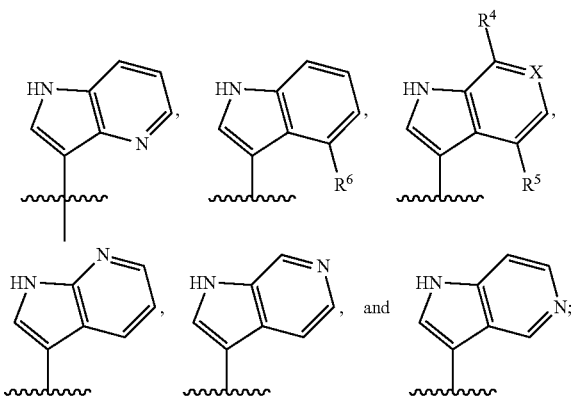

each occurrence of R² is independently selected from the group consisting of —($C_1$-$C_6$)alkyl, —($C_1$-$C_6$)fluoroalkyl, —F, —Cl, —Br, —I, and —OR⁷;

R⁴ is 1,2,4-triazolyl optionally substituted with ($C_1$-$C_6$) alkyl;

R⁵ is selected from the group consisting of H, —($C_1$-$C_6$) alkyl, —($C_1$-$C_6$)fluoroalkyl, and —OR⁷;

R⁶ is H or F;

each occurrence of R⁷ is independently selected from the group consisting of H and —($C_1$-$C_6$)alkyl;

X is CH or N;

x is an integer from 0-5; and each occurrence of n is independently 0 or 1;

a salt, solvate, or N-oxide thereof, and any combinations thereof.

8. The method of claim 7, wherein R¹ is

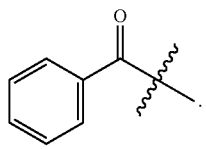 [SMILES: *C(=O)c1ccccc1]

.

9. The method of claim 7, wherein the compound is N-(3-benzoyl-3-azabicyclo[3.1.0]hexan-6-yl)-3-(4-methoxy-7-(3-methyl-1H-1,2,4-triazol-1-yl)-1H-pyrrolo[2,3-c]pyridin-3-yl)-2,3-dioxopropanamide (SC28); or a salt, N-oxide or solvate thereof.

10. The method of claim 7, wherein the method further comprises administering to the subject at least one additional therapeutic agent useful for treating HIV infection.

11. The method of claim 10, wherein the at least one additional therapeutic agent comprises at least one selected from the group consisting of a HIV drug combination, entry and fusion inhibitor, integrase inhibitor, non-nucleoside reverse transcriptase inhibitor, nucleoside reverse transcriptase inhibitor, and protease inhibitor.

12. The method of claim 10, wherein the compound and the at least one additional therapeutic agent are co-administered to the subject.

13. The method of claim 12, wherein the compound and the at least one additional therapeutic agent are coformulated.

14. The method of claim 7, wherein the subject is a mammal.

15. The method of claim 14, wherein the mammal is human.

* * * * *